United States Patent
Rooney et al.

(10) Patent No.: US 11,155,784 B2
(45) Date of Patent: *Oct. 26, 2021

(54) PROCESS OF EXPANDING T CELLS

(71) Applicants: Baylor College of Medicine, Houston, TX (US); Cell Medica Limited, London (GB)

(72) Inventors: Cliona M Rooney, Houston, TX (US); Rainer Ludwig Knaus, London (GB)

(73) Assignees: Baylor College of Medicine, Houston, TX (US); Cell Medica Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/116,023

(22) Filed: Aug. 29, 2018

(65) Prior Publication Data

US 2019/0270966 A1 Sep. 5, 2019

Related U.S. Application Data

(63) Continuation of application No. 14/364,592, filed as application No. PCT/GB2012/050896 on Apr. 23, 2012, now Pat. No. 10,351,824.

(60) Provisional application No. 61/569,577, filed on Dec. 12, 2011.

(51) Int. Cl.
*C12N 5/0783* (2010.01)
*A61K 35/15* (2015.01)
*A61K 35/17* (2015.01)
*A61P 37/04* (2006.01)
*A61K 35/12* (2015.01)
*A61K 39/00* (2006.01)

(52) U.S. Cl.
CPC ............ *C12N 5/0638* (2013.01); *A61K 35/15* (2013.01); *A61K 35/17* (2013.01); *A61P 37/04* (2018.01); *A61K 39/00* (2013.01); *A61K 2035/124* (2013.01); *C12N 2501/2304* (2013.01); *C12N 2501/2307* (2013.01); *C12N 2501/2315* (2013.01); *C12N 2501/51* (2013.01); *C12N 2502/1121* (2013.01)

(58) Field of Classification Search
None
See application file for complete search history.

(56) References Cited

U.S. PATENT DOCUMENTS

| | | |
|---|---|---|
| 5,869,453 A | 2/1999 | Moss et al. |
| 5,962,318 A | 10/1999 | Rooney et al. |
| 6,040,177 A | 3/2000 | Riddell et al. |
| 6,143,865 A | 11/2000 | Middeldorp |
| 6,274,378 B1 | 8/2001 | Steinman et al. |
| 6,455,299 B1 | 9/2002 | Steinman et al. |
| 6,528,307 B1 | 3/2003 | Herlyn |
| 6,699,477 B2 | 3/2004 | Khanna et al. |
| 6,713,053 B1 | 3/2004 | Bach et al. |
| 6,723,695 B1 | 4/2004 | Burrows et al. |
| 6,821,778 B1 | 11/2004 | Engleman et al. |
| 6,828,147 B1 | 12/2004 | Santoli et al. |
| 7,005,131 B1 | 2/2006 | Steinman et al. |
| 7,638,325 B2 | 12/2009 | June et al. |
| 7,745,140 B2 | 6/2010 | June et al. |
| 7,811,581 B2 | 10/2010 | Middeldorp |
| 7,846,446 B2 | 12/2010 | Cannon et al. |
| 7,994,096 B2 | 8/2011 | Kern et al. |
| 8,138,314 B2 | 3/2012 | Exley et al. |
| 8,481,051 B2 | 7/2013 | Kuzushima et al. |
| 8,546,137 B2 | 10/2013 | Cannon et al. |
| 8,722,401 B2 | 5/2014 | Groux et al. |
| 8,741,642 B2 | 6/2014 | Manjili et al. |
| 2002/0119121 A1 | 8/2002 | Vitiello et al. |
| 2002/0155108 A1 | 10/2002 | Barbera-Guillem |
| 2003/0148982 A1 | 8/2003 | Brenner et al. |
| 2003/0153073 A1 | 8/2003 | Rogers et al. |
| 2004/0096457 A1 | 5/2004 | Huber et al. |
| 2004/0106159 A1 | 6/2004 | Kern et al. |
| 2005/0221481 A1 | 10/2005 | Migliaccio et al. |
| 2006/0204509 A1 | 9/2006 | Harty et al. |
| 2007/0048329 A1 | 3/2007 | Khanna et al. |
| 2009/0098090 A1 | 4/2009 | Hart et al. |
| 2009/0305408 A1 | 12/2009 | Chang |
| 2010/0035282 A1 | 2/2010 | Bonini et al. |
| 2010/0254958 A1 | 10/2010 | Letsch et al. |
| 2011/0059133 A1 | 3/2011 | Adhikary et al. |
| 2011/0136228 A1 | 6/2011 | Vera et al. |
| 2011/0182870 A1 | 7/2011 | Leen et al. |
| 2011/0236363 A1 | 9/2011 | Chang et al. |
| 2012/0100180 A1 | 4/2012 | Gao et al. |
| 2012/0244132 A1 | 9/2012 | Stauss et al. |
| 2013/0045491 A1 | 2/2013 | Unutmaz |
| 2013/0058909 A1 | 3/2013 | Szabolcs |
| 2013/0102075 A1 | 4/2013 | Vera et al. |
| 2013/0115617 A1 | 5/2013 | Wilson |
| 2013/0129713 A1 | 5/2013 | Rescigno et al. |
| 2013/0217122 A1 | 8/2013 | Kaplan |
| 2014/0212398 A1 | 7/2014 | Reisner et al. |
| 2015/0010519 A1 | 1/2015 | Leen et al. |
| 2015/0175966 A1 | 6/2015 | Vera et al. |
| 2015/0337262 A1 | 11/2015 | Ethell |

FOREIGN PATENT DOCUMENTS

| | | |
|---|---|---|
| WO | 1994002156 | 2/1994 |
| WO | 1994002156 A1 | 2/1994 |

(Continued)

OTHER PUBLICATIONS

Ando et al., "Towards Phase 2/3 Trials for Epstein-Barr Virus (EBV)-Associated Malignancies," Blood (ASH Annual Meeting Abstracts) 118, Abstract 4043, 1 p., 2011.

(Continued)

*Primary Examiner* — Michail A Belyavskyi
(74) *Attorney, Agent, or Firm* — Norton Rose Fulbright US LLP

(57) ABSTRACT

The present disclosure relates to a novel process for expanding T cells, such as autologous T cells, cell populations therefrom, pharmaceutical compositions comprising the said cell populations and use of the cells and compositions for treatment, particular the treatment or prophylaxis of virus infection and/or cancer, for example in immune compromised or immune competent human patients.

21 Claims, 17 Drawing Sheets

Specification includes a Sequence Listing.

(56) References Cited

FOREIGN PATENT DOCUMENTS

| WO | 1995027722 | 10/1995 |
| WO | 1995027722 A1 | 10/1995 |
| WO | 1998033888 | 8/1998 |
| WO | 1998033888 A1 | 8/1998 |
| WO | 2008025992 | 3/2008 |
| WO | 2008025992 A2 | 3/2008 |
| WO | 2011024482 | 3/2011 |
| WO | 2011024482 A1 | 3/2011 |

OTHER PUBLICATIONS

Ando Jun et al "Towards Phase 2/3 Trials for Epstein-Barr Virus (EBV)-Associated Malignancies", Blood, vol. 118, No. 21, Nov. 2011, p. 1727.

Britten et al., "The use of HLA-A*0201-transfected K562 as standard antigen-presenting cells for CD8+ T lymphocytes in IFN-? ELISPOT assays," J. Immunol. Methods 259, 95-110, 2002.

Burkett et al, IL-15R expression on CD8+ T cells is dispensable for T cell memory, PNAS Apr. 15, 2003, vol. 100, No. 8.

Cornish et al, Differential regulation of T-cell growth by IL-2 and IL-15, Blood, Jul. 15, 2006, vol. 108, No. 2.

Decaussin et al., "Expression of BARF1 Gene encoded by Epstein-Ban Virus in Nasopharyngeal Carcinoma Biopsies," cancer Res. 60, 5584-88, 2000.

Foster et al., "Autologous Designer Antigen-presenting Cells by Gene Modification of T Lymphocytes Blasts With IL-7 and IL-12," J. Immunother. 30, 506-16, 2007.

Gerdemann et al: "Cytotoxic T lymphocytes simultaneously targeting multiple tumor-associated antigens to treat EBV negative lymphoma", MolecularTherapy: The Journal of the American Society of Gene Therapy, vol. 19, No. 12, Sep. 13, 2011, pp. 2258-2268.

Gerdemann et al: "Generation of Multivirus-specific T Cells to Prevent/treat Viral Infections after Allogeneic Hematopoietic Stem Cell Transplant", Journal of Visualized Experiments, No. 51, May 27, 2011.

Gerdemann et al: "Rapidly Generated Multivirus-specific Cytotoxic T Lymphocytes for the Prophylaxis and Treatment of Viral Infections", Molecular Therapy, vol. 20, No. 8, Jul. 17, 2012.

Huye et al., "Combing mTor Inhibitors With Rapamycin-resistant T Cells: A Two-pronged Approach to Tumor Elimination," Mol. Ther. 19, 2239-48, 2011.

International Search Report dated Aug. 10, 2012 in PCT/GB2012/050896.

Jeras et al., "Induction/Engineering, Detection, Selection, and Expansion of Clinical-Grade Human Antigen-Specific CD8+ Cytotoxic T Cell Clones for Adoptive Immunotherapy," Journal of Biomedicine and Biotechnology, vol. 2010, Article ID 705215,2010, 15 pages.

Lapteva & Vera, "Optimization Manufacture of Virus- and Tumor-Specific T Cells," Stem Cells International 2011, Article ID 434392, 8 pages.

Lee et al, HLA A2.1-restricted Cytotoxic T cells Recognizing a Range of Epstein-Barr Virus Isolates through a Defined Epitope in Latent Membrane Protein LMP2, Journal of Virology, Dec. 1993, p. 7428-7435.

Liu et al, IL-15 mimics T cell receptor crosslinking in the induction of cellular proliferation, gene expression and cytotoxicity in CD8+ memory T cells, PNAS Apr. 30, 2002, vol. 99, No. 9.

Merlo et al., "The interplay between Epstein-Barr virus and the immune system: a rationale for adoptive cell therapy of EBV-related disorders," Haematologica 95, 1769-77, 2010.

Merrick et al., "Autologous versus allogeneic peptide-pulsed dendritic cells for anti-tumour vaccination: expression of allogeneic MHC supports activation of antigen specific T cells but impairs early naive cytotoxic priming and anti-tumou therapy," Cancer Immunol. Immunother. 57, 897-906, 2008.

Montes et al, Optimum in vitro expansion of human antigen-specific CD8+ T cells for adoptive transfer therapy, Clinical and Experimental Immunology Jul. 12, 2005, 142: 292-302.

Ngo, "Towards Phase 2/3 Trials for Epstein-Barr Virus (EBV)-Associated Malignancies," 2011 Graduate Student Symposium of the Graduate School of Biomedical Sciences at Baylor College of Medicine, p. 231, 2011.

Redchenko & Rickinson, "Accessing Epstein-Barr Virus-Specific T-Cell Memory with Peptide-Loaded Dendritic Cells," J. Virol. 73, 334-42, 1999.

Rudolf et al., "Potent costimulation of human CD8 T cells by anti-4-1BB and anti-CD28 on synthetic artificial antigen presenting cells," Cancer Immunol. Immunother. 57, 175-83, Epub 2007.

Suhoski et al., "Engineering artificial antigen-presenting cells to express a diverse array of co-stimulatory molecules," Mol. Ther. 15, 981-88, 2007.

Tan et al, A re-evaluation of the frequency of CD8+ T cells specific for EBV in healthy virus carriers, Journal of Immunology 1999; 162: 1827-1835.

Taylor et al., "Mechanisms of immune suppression by interleukin-10 and transforming growth factor-.beta.: the role of T regulatory cells," Immunology 117, 433-42, 2006.

Turtle & Riddell, "Artificial antigen presenting cells for use in adoptive immunotherapy," Cancer J. 16, 374-81, 2010.

Vera et al, Accelerated Production of Antigen-specific T cells for Preclinical and Clinical Applications Using Gas Permeable Rapid Expansion Cultureware (G-Rex), J Immunother 2010; 33: 305-315.

Decaussin et al., "Expression of BARF1 Gene encoded by Epstein-Barr Virus in Nasopharyngeal Carcinoma Biopsies," cancer Res. 60, 5584-88, 2000.

Fujiwara et al., "Identification and in vitro expansion of CD4+ and CD8+ T cells specific for human neutrophil elastase", Blood, 103(8), pp. 3076-3083, Apr. 15, 2004 (Apr. 15, 2004).

Kim et al., "The ABCs of artificial antigen presentation", Nature Biotechnology, 22(4), pp. 403-410, Apr. 2004 (Apr. 2004).

Quintarelli et al., "Cytotoxic T lymphocytes directed to the preferentially expressed antigen of melanoma (PRAME) target chronic myeloid leukemia", Blood, 112(5), pp. 1876-1885, Sep. 1, 2008 (Sep. 1, 2008).

FIGURE 1    The prior art process for generating EVB specific T cells
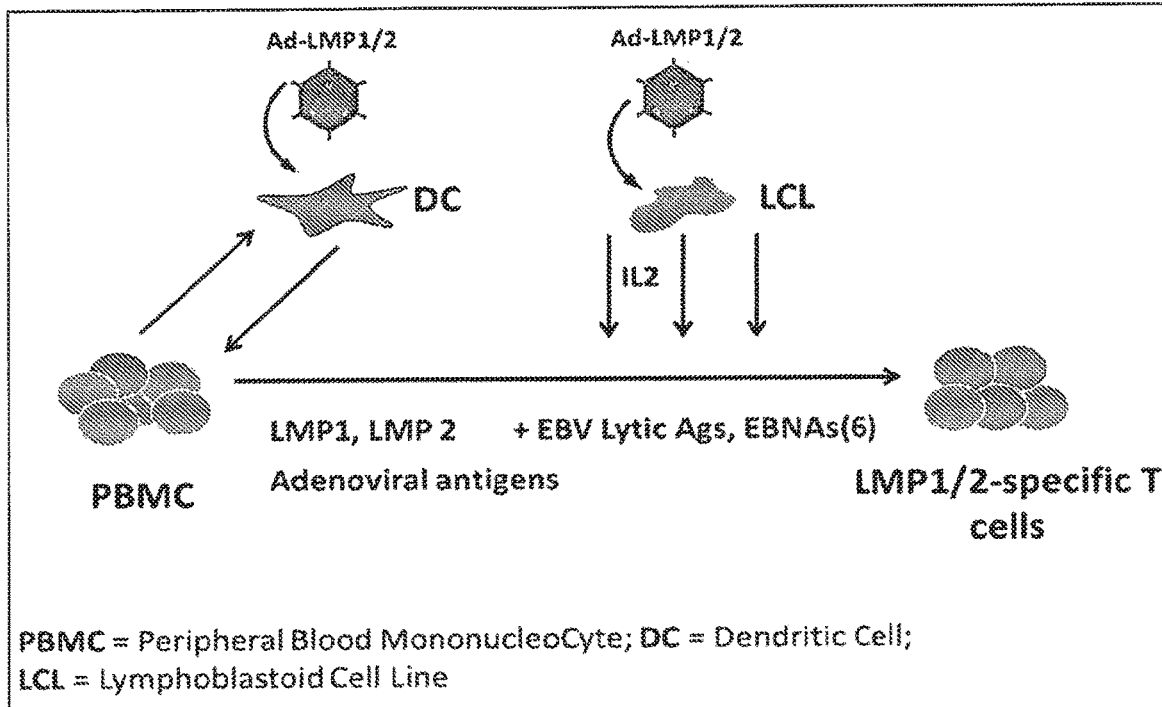
FIGURE 2    Diagram of the alternative methods demonstrated in this application of novel superior protocols for the generation of EBV specific T cells.
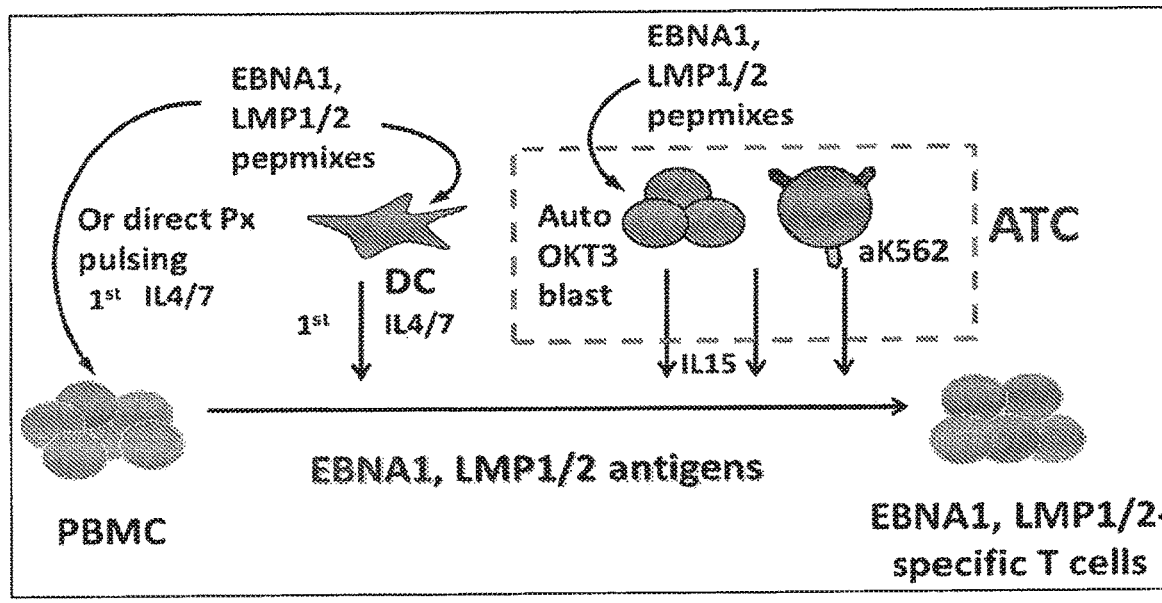

FIGURE 3A    Diagram showing the combination of T-APC (activated T cells) and aK562 that is employed as the second stimulation in the invention.
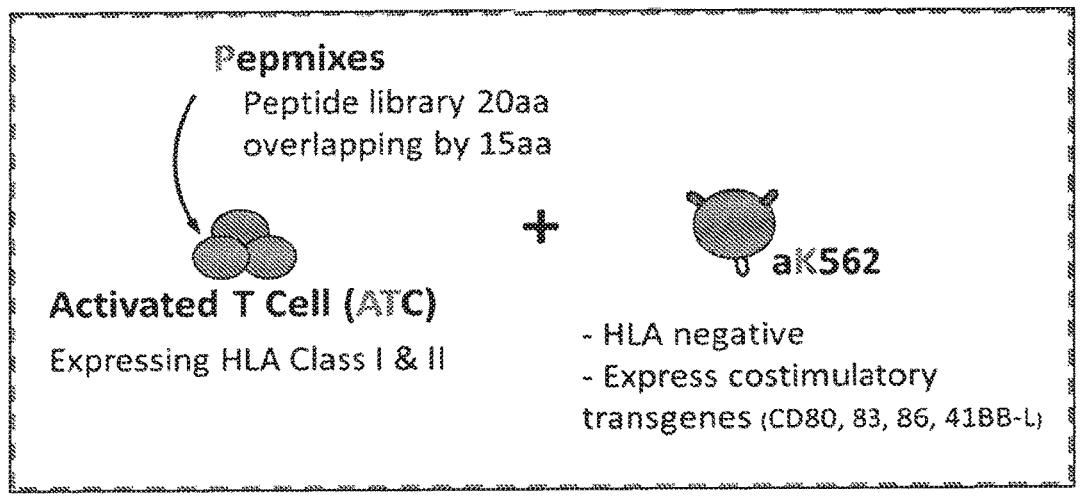
FIGURE 3B    The expansion of specific T cells using aK562 and T-APC showing the different ratios used in step b) of the invention.
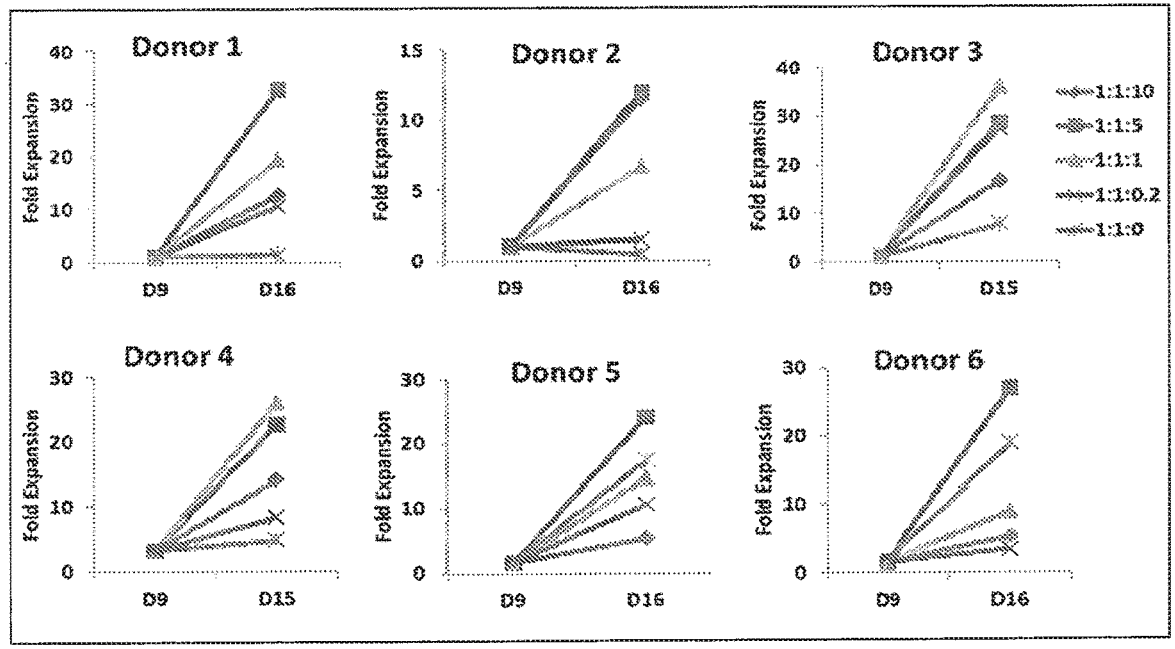

FIGURE 3C   The optimal CTL (T cell) to T-APC (OKT3 Blast) to aK562 ratio for T cell expansion in step b) of the invention.
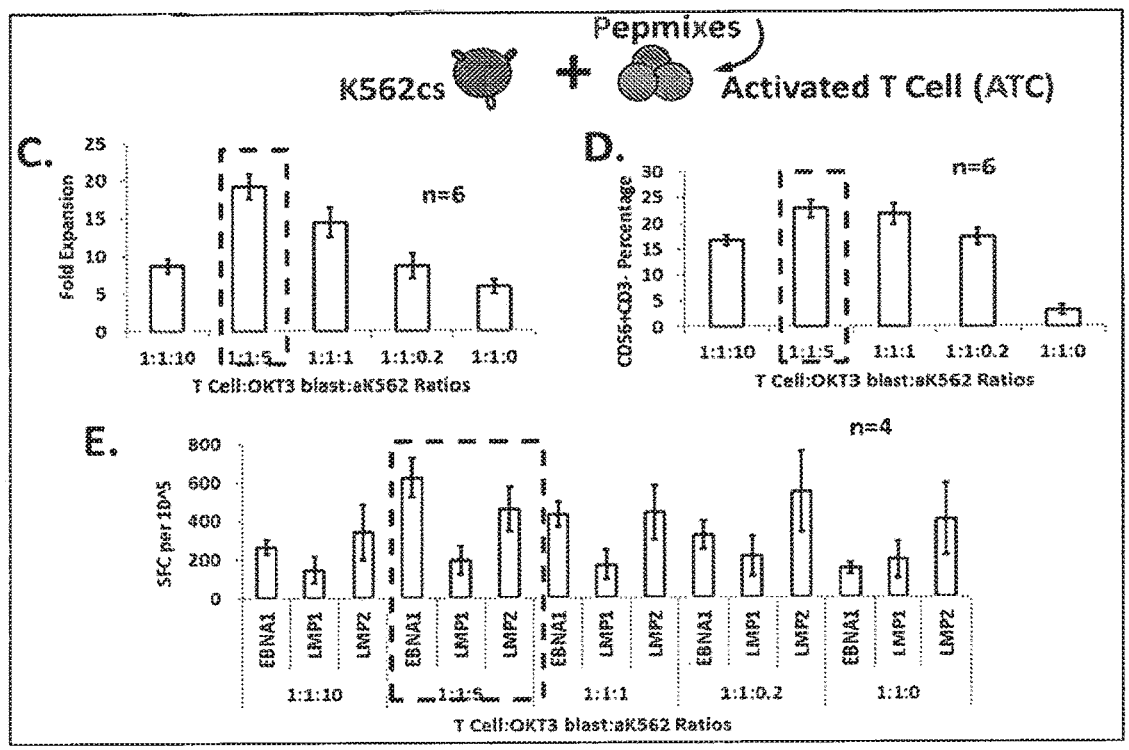
FIGURE 3D   A more detailed analysis of individual donors from figure 3B (E) showing specific IFNg production by expanded CTLs from 2 donors.
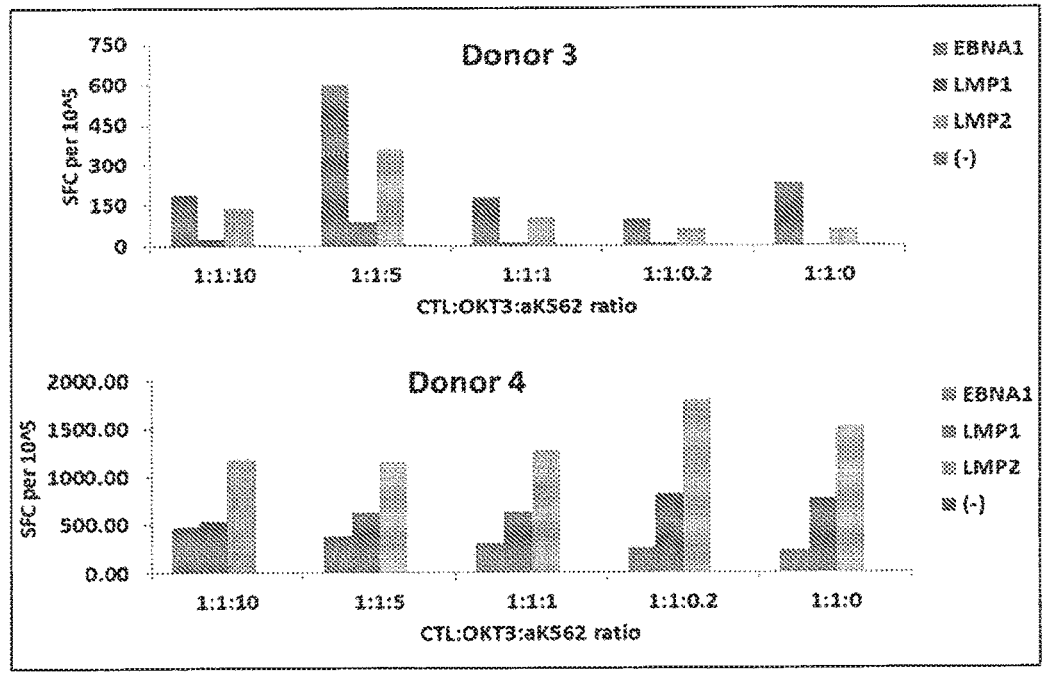

FIGURE 3E    T-APC CAN Act As Antigen Presenting Cells for Class I and II
A.
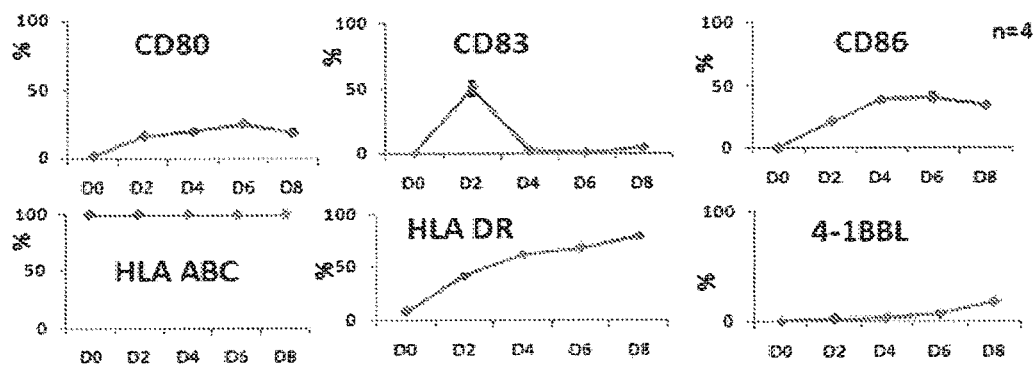
B. aK562cs express high levels of co-stimulatory molecules but no MHC
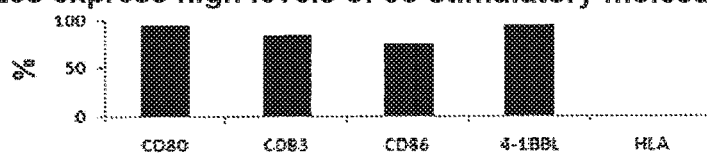
FIGURE 4A    A Schematic representation of the main stimulation steps used in the prior art process and the various embodiments of the invention.
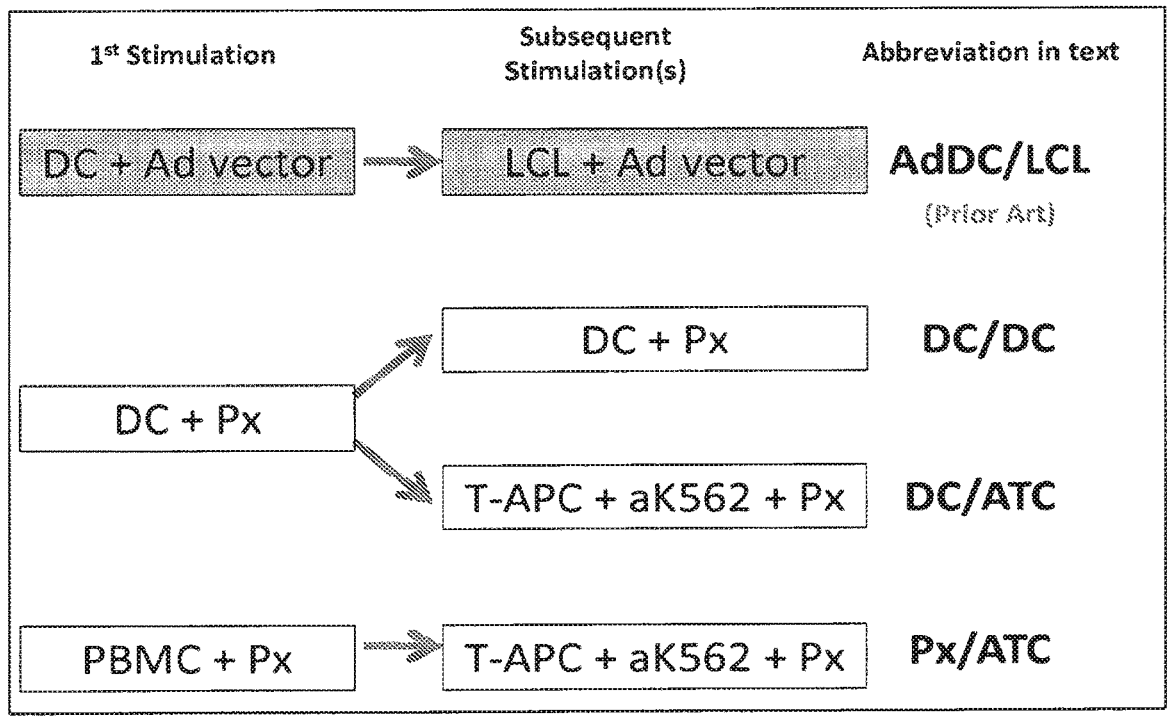

FIGURE 4B   Expansion of cells from a healthy donor in response to EBV antigens using the prior art and the new embodiments of the invention.
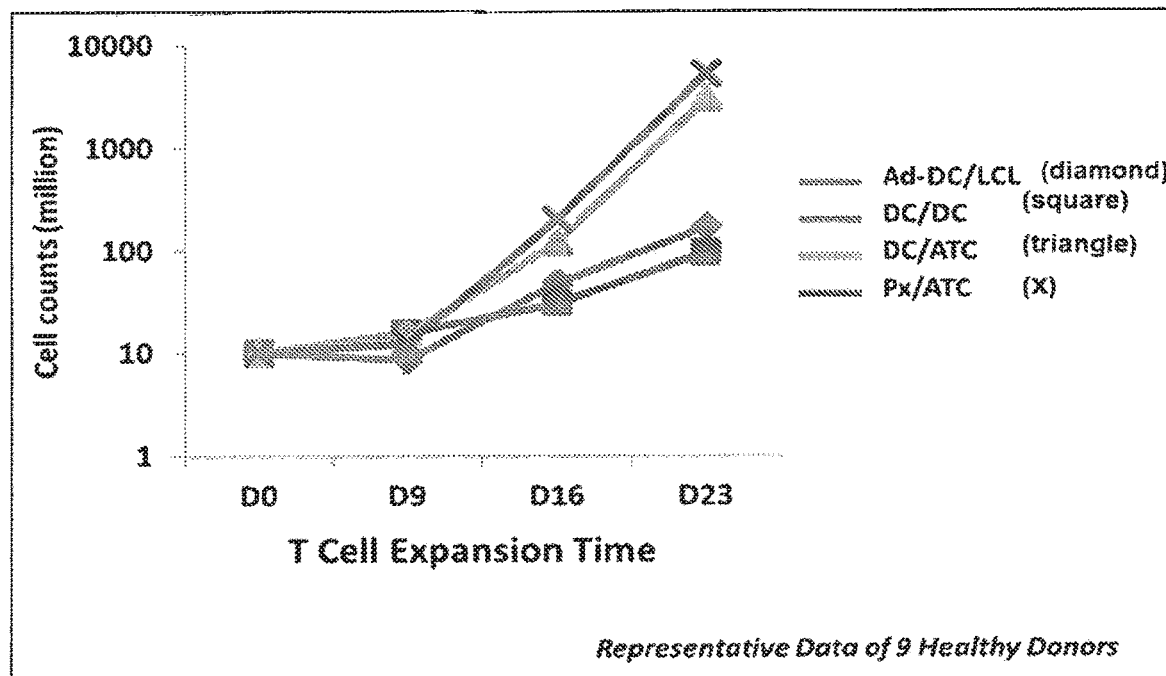

FIGURE 4C  The number of antigen specific, IFNg secreting T cells in the final cell population was increased in the embodiments of the invention compared to the prior art method
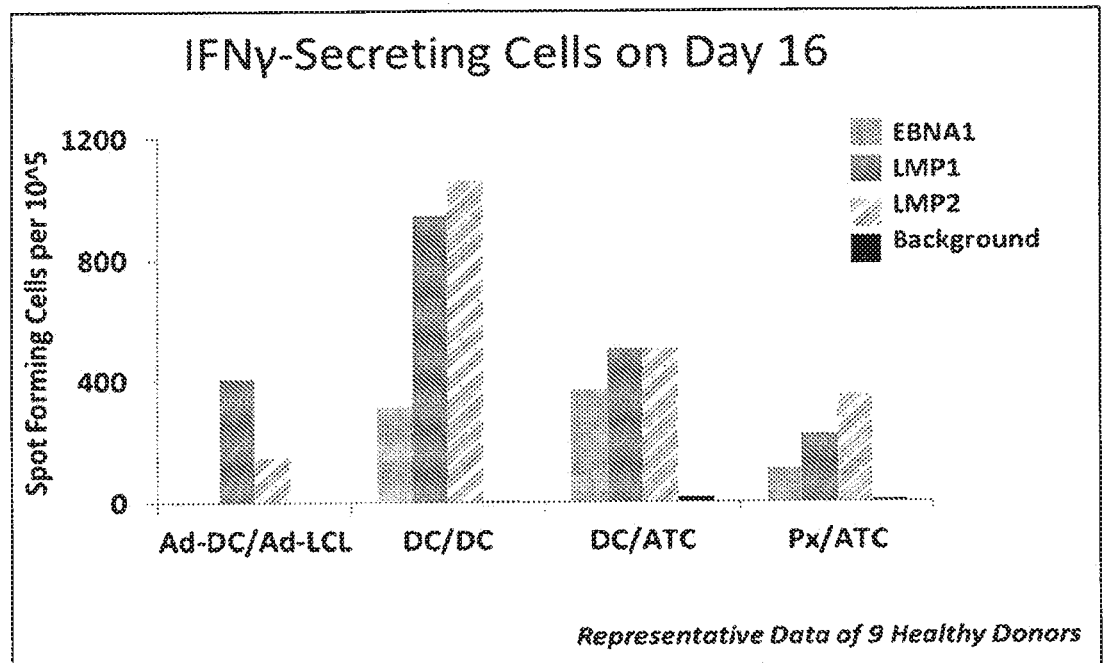
FIGURE 4D
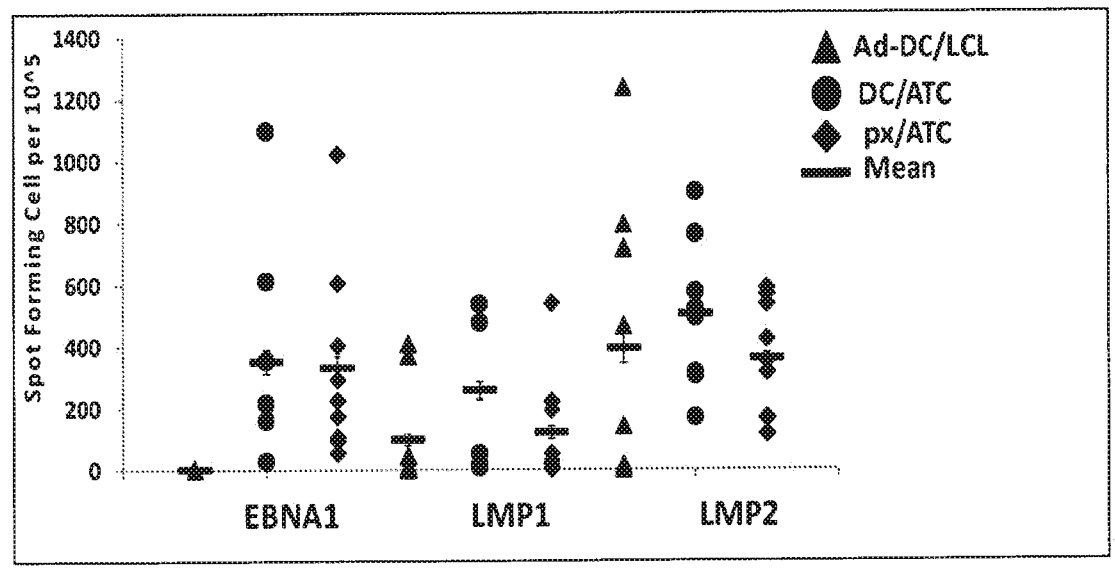

FIGURE 4E  The avidity of the T cell receptors for the different peptide antigens is not decreased by the use of the various embodiments when compared to the prior art process.
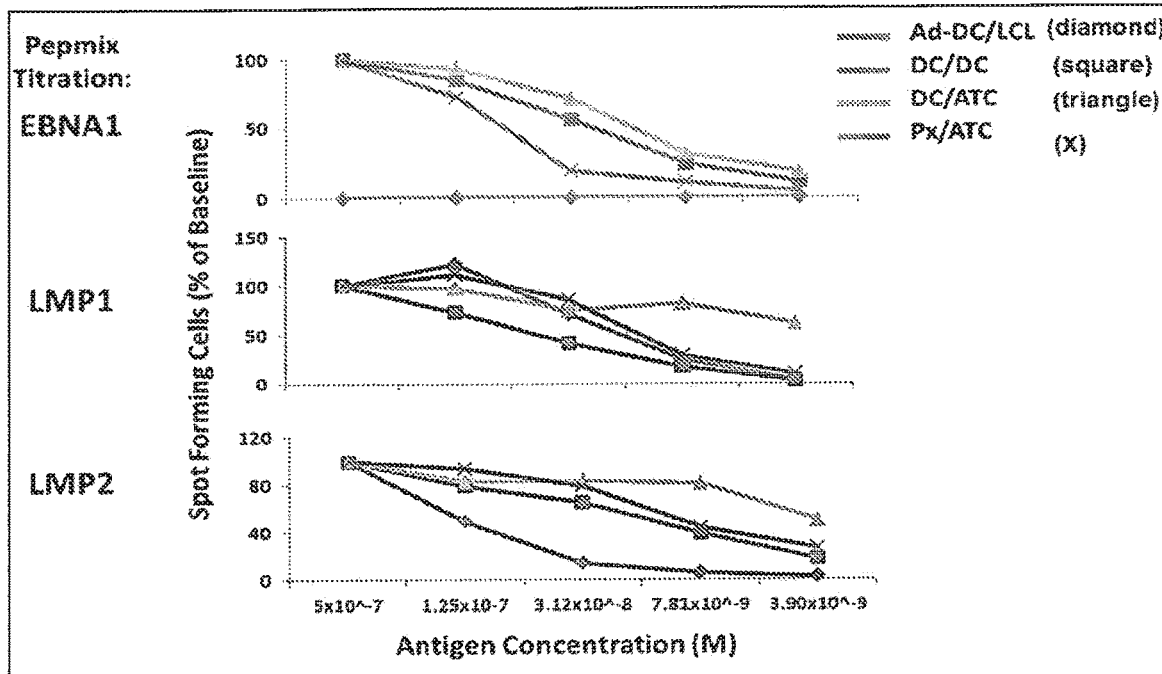
FIGURE 4F  T cell markers for the cellular composition and activation markers in the prior art method and the embodiments of the invention.
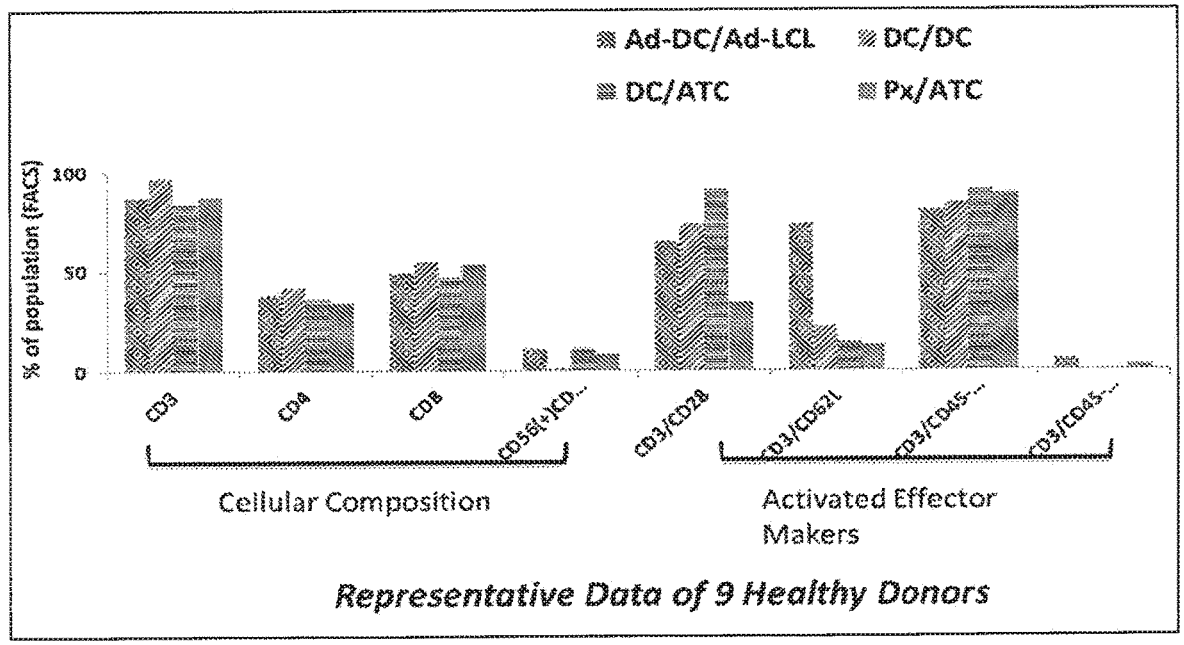

FIGURE 4G  Culture of cells using the prior art skews responses towards antigens expressed in LCL cells rather than on the latency type 2 antigens present in EBV+ cancer cells from lymphoma and NPC patients.. The new methods therefore focus the specificity of the expanded CTLs towards clinically relevant antigens.

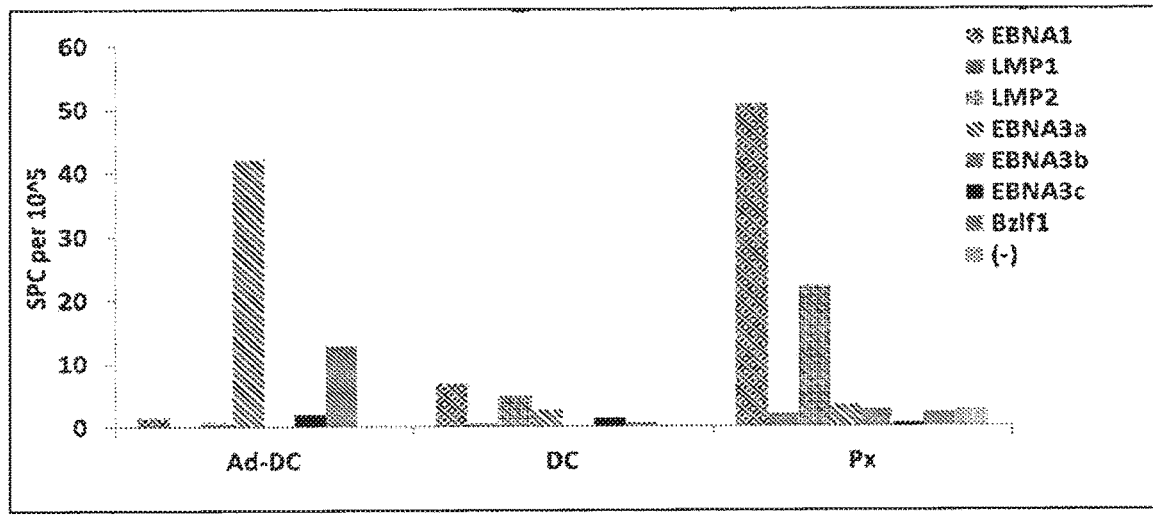

FIGURE 5A  A Schematic representation of the main stimulation steps used in the prior art process and the various embodiments of the invention.

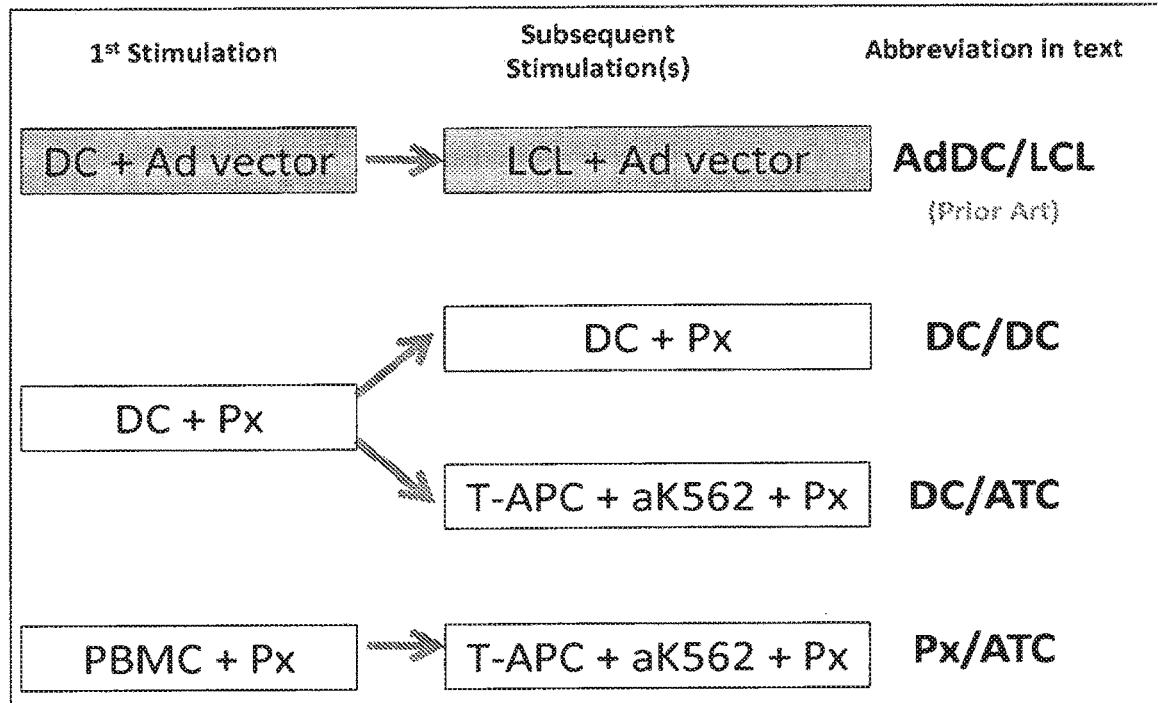

FIGURE 5B  Expansion of EBV specific T cells is enhanced in 2 of the 3 embodiments when compared to the prior art in NPC patients.
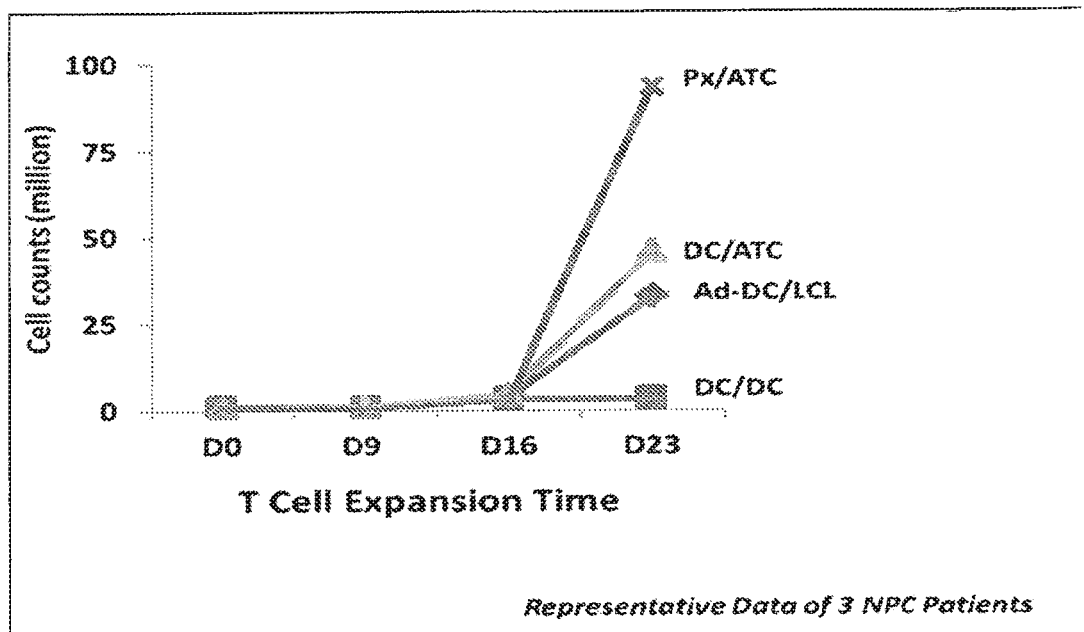
FIGURE 5C
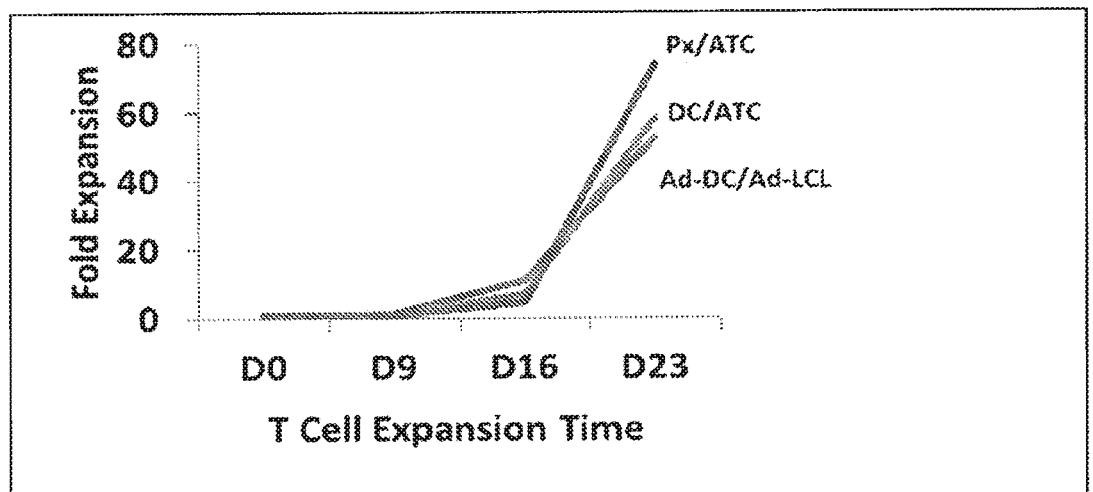

FIGURE 5D  EBV specific T cells expanded from NPC patients show enhanced specificity when using the embodiments of the invention compared to the prior art method.
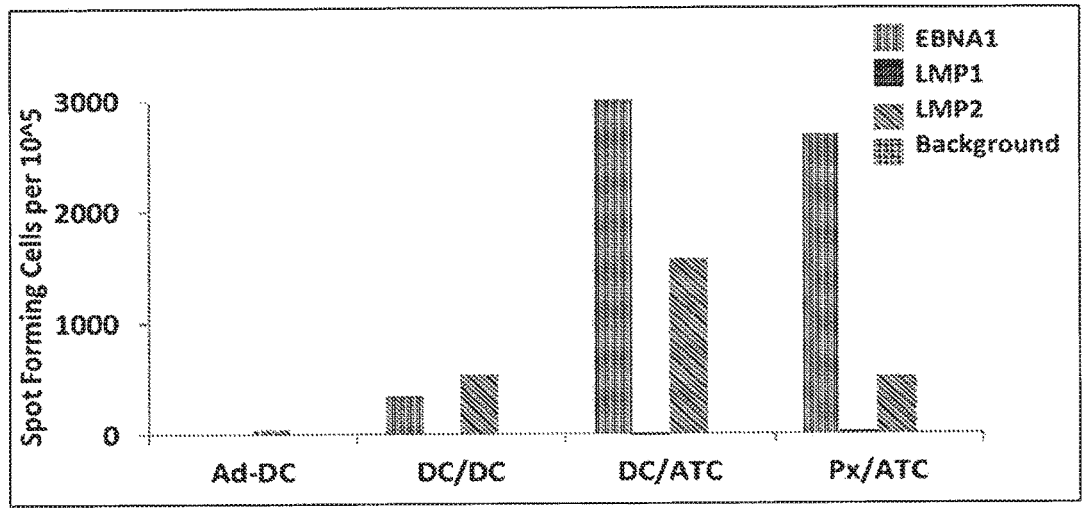
FIGURE 5E  The avidity of the T cell receptors for the different peptide antigens is not decreased by the use of the various embodiments when compared to the prior art process in NPC patients.
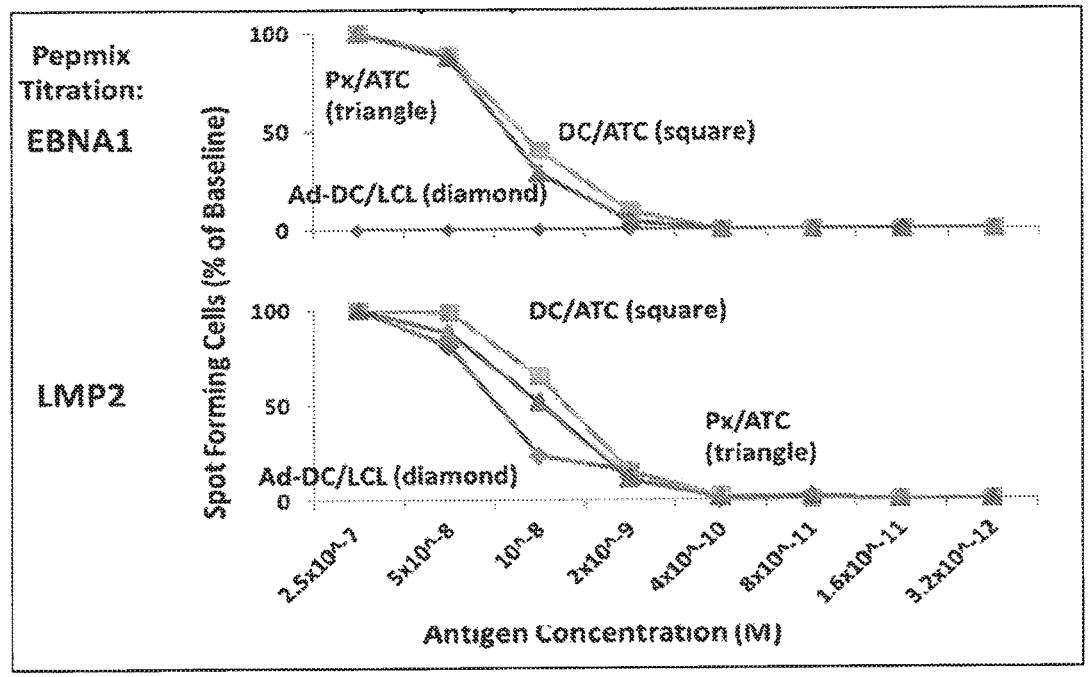

FIGURE 5F   T cell markers for the cellular composition and activation markers in the prior art method and the embodiments of the invention in NPC patients.
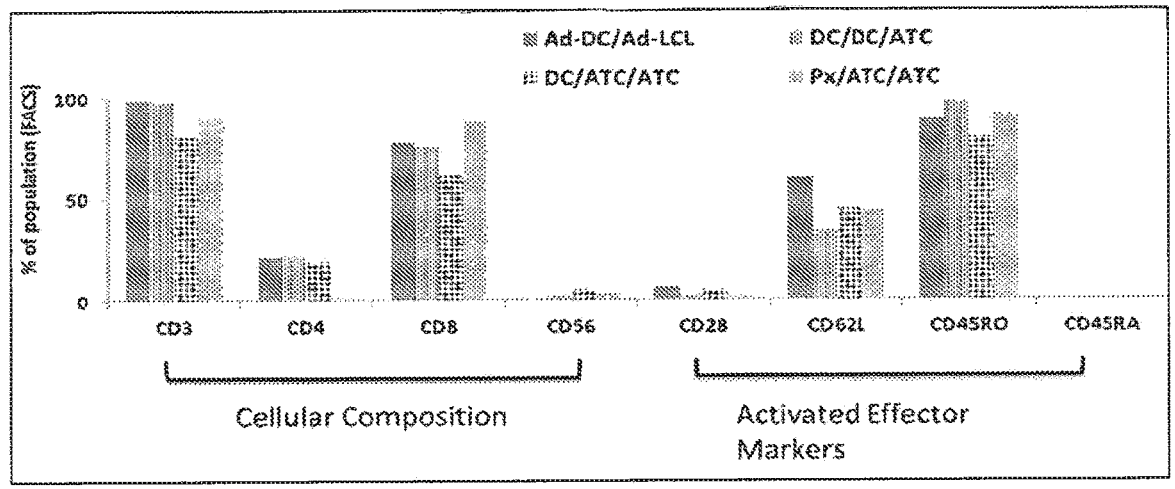
FIGURE 5G   T Cells from NPC patients expanded employing the new embodiments of the invention(CD3+/CD19-) kill LCL (EBV+ cancer cell-line, CD3-/CD19+) better in co-culture for 4 and 10 days as T cells expanded by the prior art.
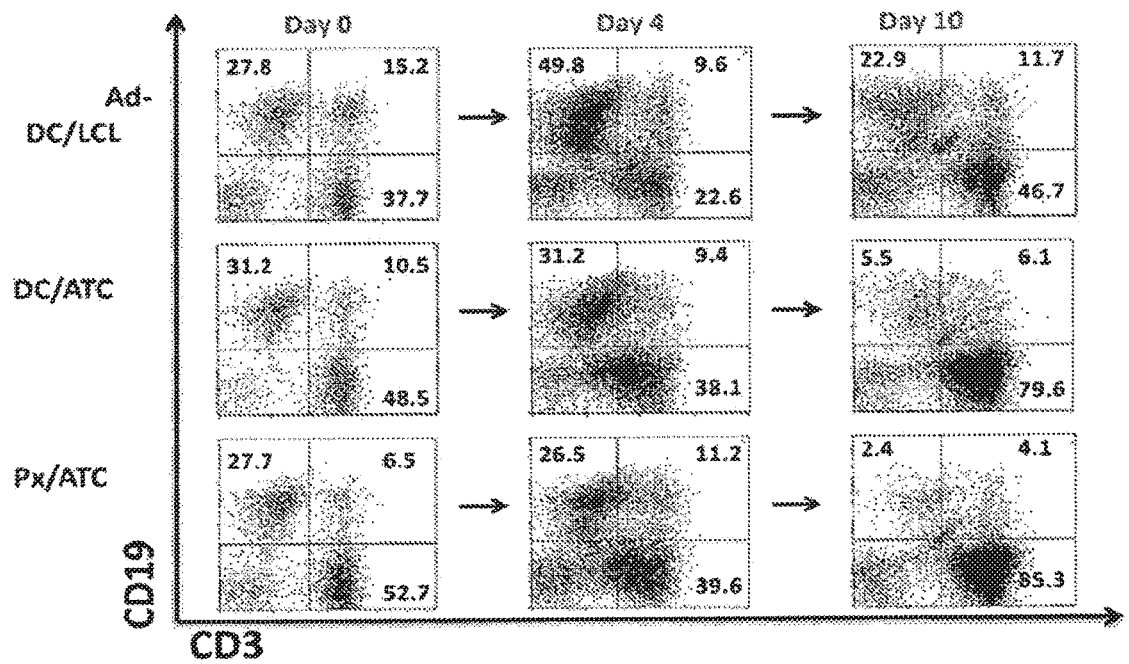

FIGURE 6A    A Schematic representation of the main stimulation steps used in the prior art process and the various embodiments of the invention.
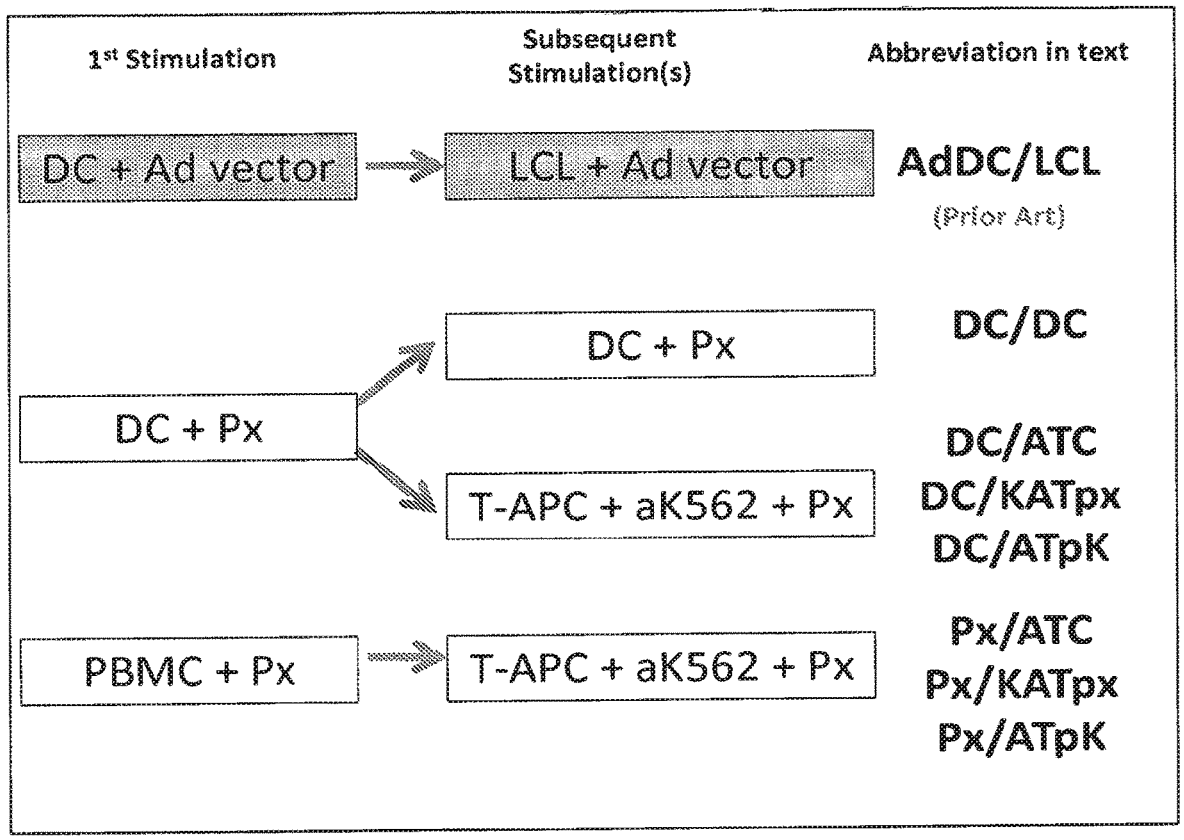

FIGURE 6B    Expansion of EBV specific T cells is enhanced in 2 of the 3 embodiments when compared to the prior art in lymphoma patients.
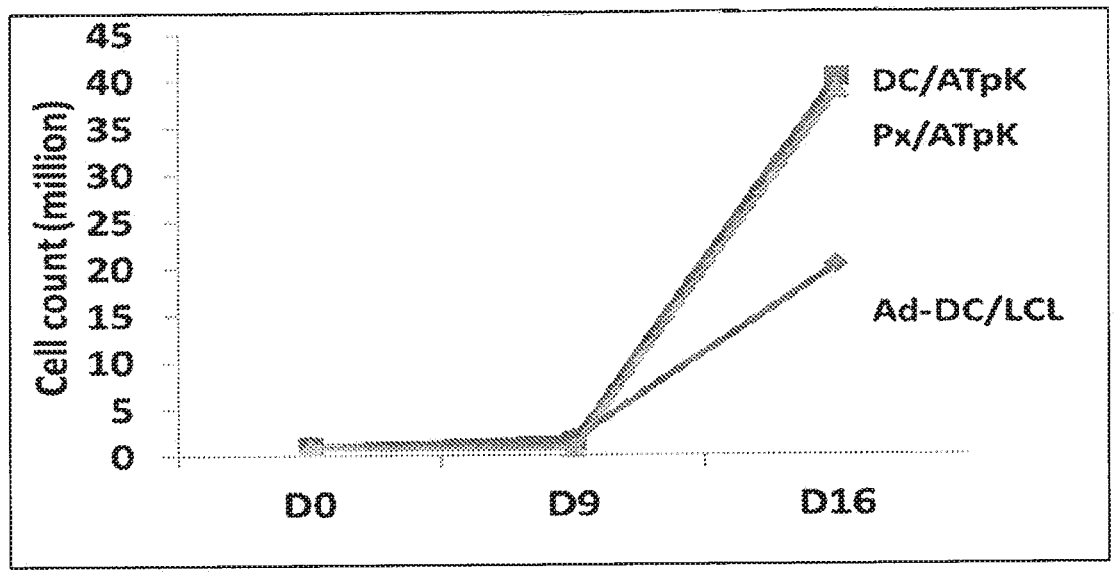
FIGURE 6C
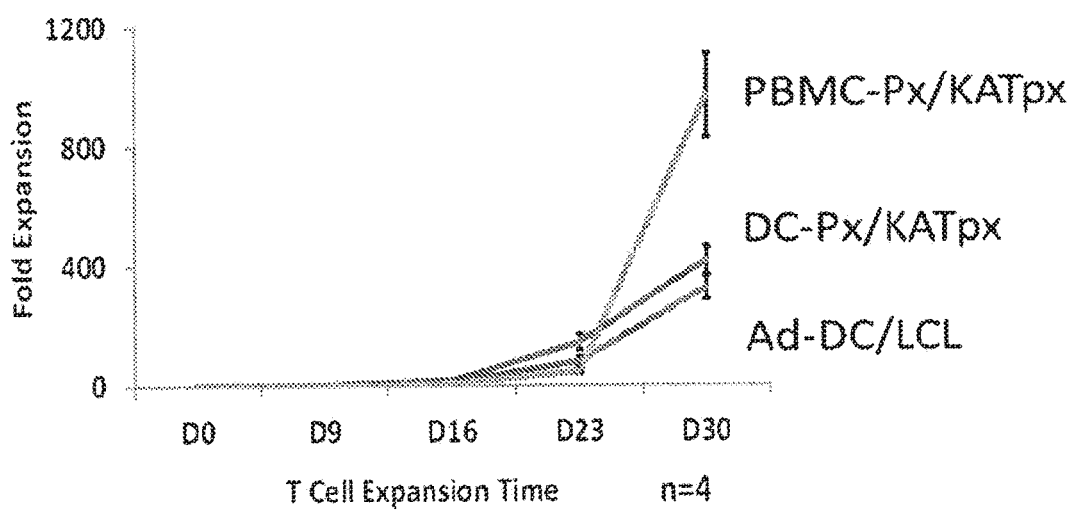

FIGURE 6D  EBV specific T cells expanded from lymphoma patients show enhanced specificity when using the embodiments of the invention compared to the prior art method.
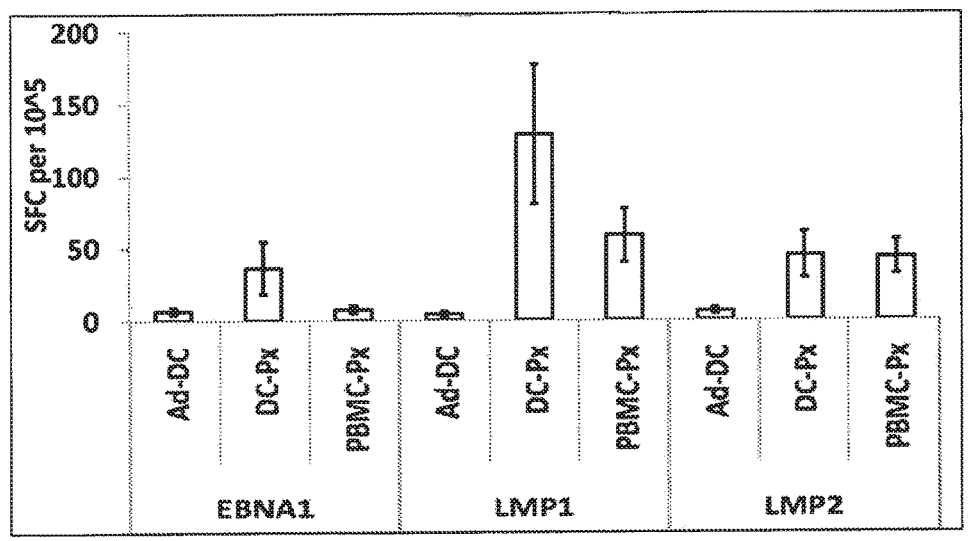

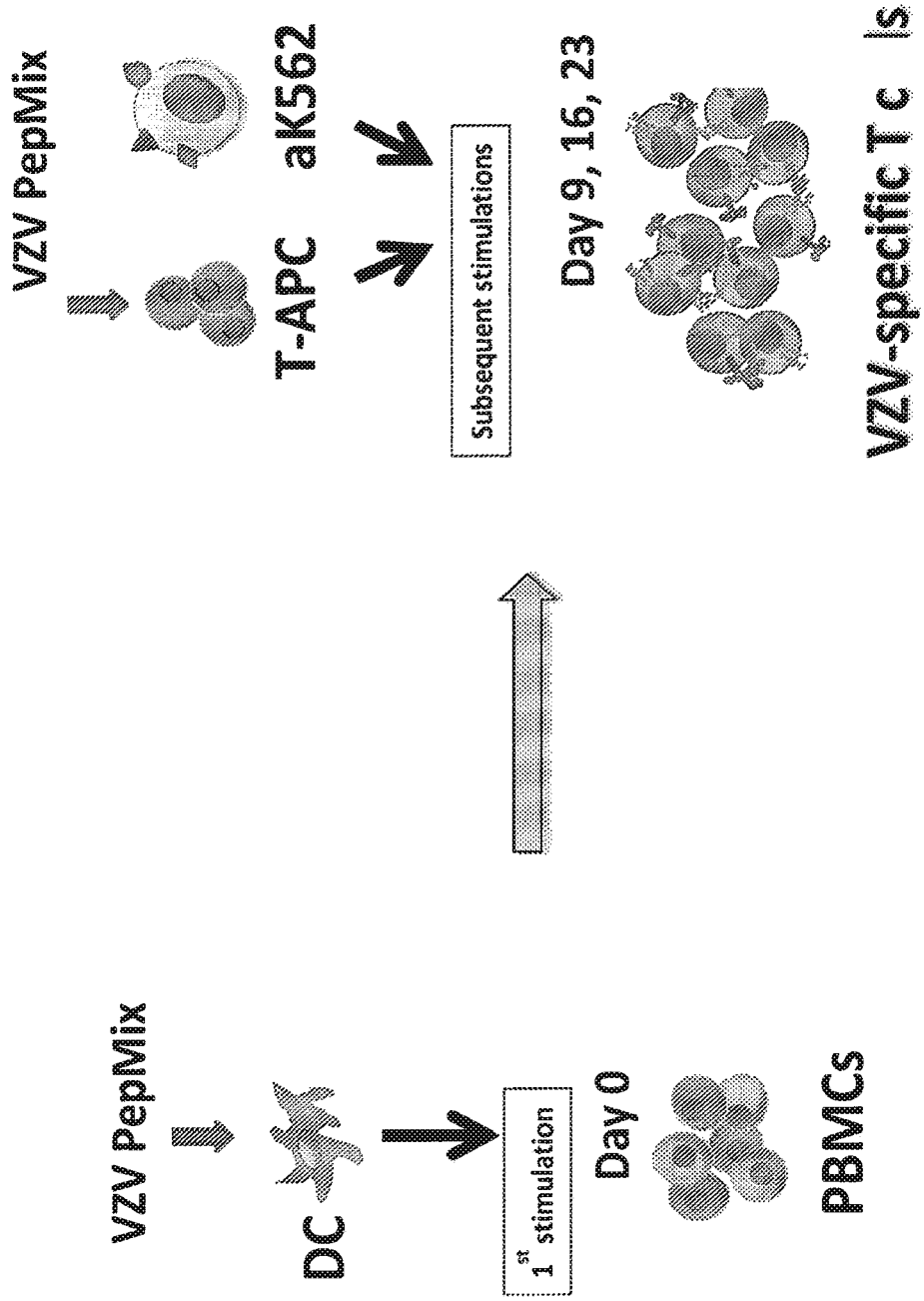
FIGURE 7A is a schematic representation of the embodiment of the invention that was used to expand VZV specific T cells from the PBMC of a healthy donor FIGURE 7B    Expansion of VZV-specific T cells
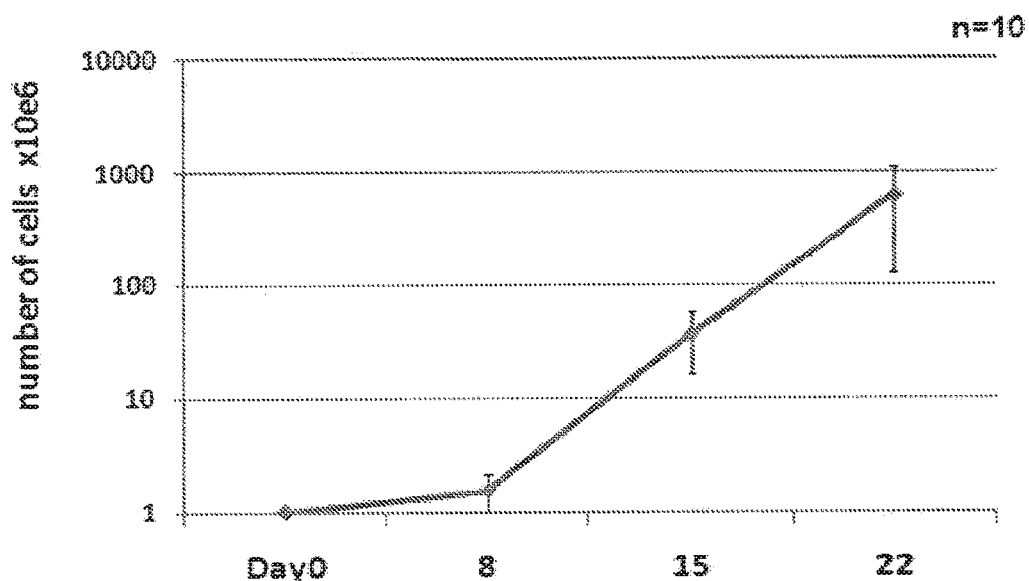
FIGURE 7C    IFNg secreting cells in cultures of VZV specific T cells
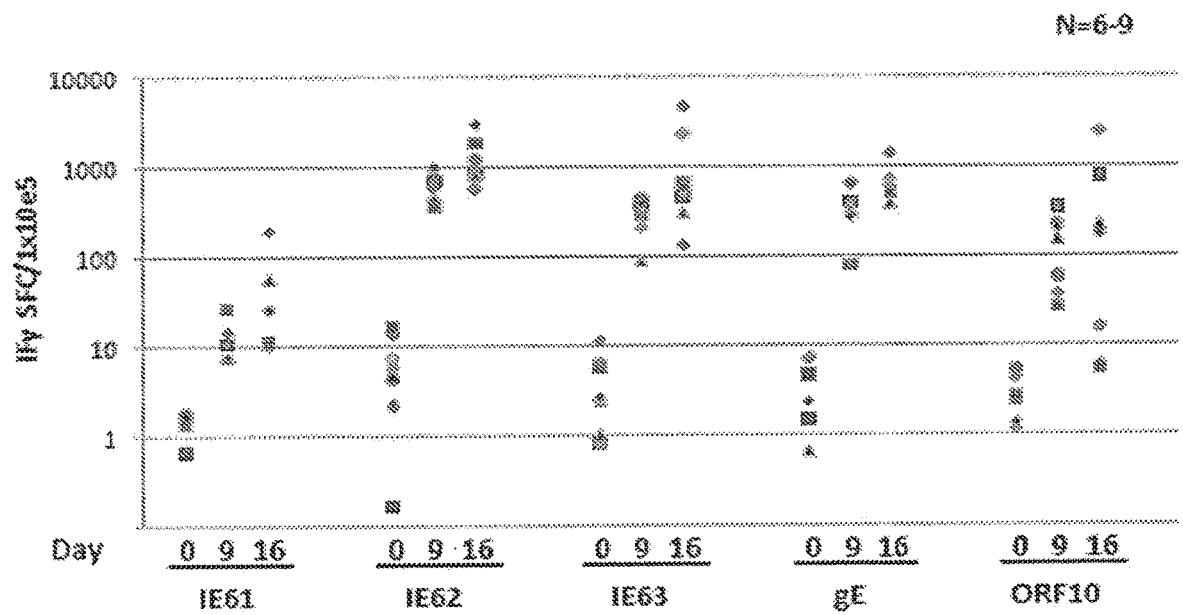

SEQUENCE LISTING

<160> NUMBER OF SEQ ID NOS: 340

<210> SEQ ID NO 1
<211> LENGTH: 15
<212> TYPE: PRT
<213> ORGANISM: Herpes viridae

<400> SEQUENCE: 1

Met Ser Asp Glu Gly Pro Gly Thr Gly Pro Gly Asn Gly Leu Gly
1               5                   10                  15

<210> SEQ ID NO 2
<211> LENGTH: 15
<212> TYPE: PRT
<213> ORGANISM: Herpes viridae

```
<400> SEQUENCE: 2

Gly Pro Gly Thr Gly Pro Gly Asn Gly Leu Gly Glu Lys Gly Asp
1               5                   10                  15

<210> SEQ ID NO 3
<211> LENGTH: 15
<212> TYPE: PRT
<213> ORGANISM: Herpes viridae

<400> SEQUENCE: 3

Gly Pro Gly Asn Gly Leu Gly Glu Lys Gly Asp Thr Ser Gly Pro
1               5                   10                  15

<210> SEQ ID NO 4
<211> LENGTH: 15
<212> TYPE: PRT
<213> ORGANISM: Herpes viridae

<400> SEQUENCE: 4

Gly Leu Gly Glu Lys Gly Asp Thr Ser Gly Pro Glu Gly Ser Gly
1               5                   10                  15

<210> SEQ ID NO 5
<211> LENGTH: 15
<212> TYPE: PRT
<213> ORGANISM: Herpes viridae

<400> SEQUENCE: 5

Lys Gly Asp Thr Ser Gly Pro Glu Gly Ser Gly Gly Ser Gly Pro
1               5                   10                  15

<210> SEQ ID NO 6
<211> LENGTH: 15
<212> TYPE: PRT
<213> ORGANISM: Herpes viridae

<400> SEQUENCE: 6

Ser Gly Pro Glu Gly Ser Gly Gly Ser Gly Pro Gln Arg Arg Gly
1               5                   10                  15

<210> SEQ ID NO 7
<211> LENGTH: 15
<212> TYPE: PRT
<213> ORGANISM: Herpes viridae

<400> SEQUENCE: 7

Gly Ser Gly Gly Ser Gly Pro Gln Arg Arg Gly Gly Asp Asn His
1               5                   10                  15

<210> SEQ ID NO 8
<211> LENGTH: 15
<212> TYPE: PRT
<213> ORGANISM: Herpes viridae

<400> SEQUENCE: 8

Ser Gly Pro Gln Arg Arg Gly Gly Asp Asn His Gly Arg Gly Arg
1               5                   10                  15

<210> SEQ ID NO 9
<211> LENGTH: 15
<212> TYPE: PRT
<213> ORGANISM: Herpes viridae
```

```
<400> SEQUENCE: 9

Arg Arg Gly Gly Asp Asn His Gly Arg Gly Arg Gly Arg Gly Arg
1               5                   10                  15

<210> SEQ ID NO 10
<211> LENGTH: 15
<212> TYPE: PRT
<213> ORGANISM: Herpes viridae

<400> SEQUENCE: 10

Asp Asn His Gly Arg Gly Arg Gly Arg Gly Arg Gly Arg Gly Gly
1               5                   10                  15

<210> SEQ ID NO 11
<211> LENGTH: 15
<212> TYPE: PRT
<213> ORGANISM: Herpes viridae

<400> SEQUENCE: 11

Arg Gly Arg Gly Arg Gly Arg Gly Arg Gly Gly Gly Arg Pro Gly
1               5                   10                  15

<210> SEQ ID NO 12
<211> LENGTH: 15
<212> TYPE: PRT
<213> ORGANISM: Herpes viridae

<400> SEQUENCE: 12

Arg Gly Arg Gly Arg Gly Gly Gly Arg Pro Gly Ala Pro Gly Gly
1               5                   10                  15

<210> SEQ ID NO 13
<211> LENGTH: 15
<212> TYPE: PRT
<213> ORGANISM: Herpes viridae

<400> SEQUENCE: 13

Arg Gly Gly Gly Arg Pro Gly Ala Pro Gly Gly Ser Gly Ser Gly
1               5                   10                  15

<210> SEQ ID NO 14
<211> LENGTH: 15
<212> TYPE: PRT
<213> ORGANISM: Herpes viridae

<400> SEQUENCE: 14

Arg Pro Gly Ala Pro Gly Gly Ser Gly Ser Gly Pro Arg His Arg
1               5                   10                  15

<210> SEQ ID NO 15
<211> LENGTH: 15
<212> TYPE: PRT
<213> ORGANISM: Herpes viridae

<400> SEQUENCE: 15

Pro Gly Gly Ser Gly Ser Gly Pro Arg His Arg Asp Gly Val Arg
1               5                   10                  15

<210> SEQ ID NO 16
<211> LENGTH: 15
<212> TYPE: PRT
<213> ORGANISM: Herpes viridae
```

```
<400> SEQUENCE: 16

Gly Ser Gly Pro Arg His Arg Asp Gly Val Arg Arg Pro Gln Lys
1               5                   10                  15

<210> SEQ ID NO 17
<211> LENGTH: 15
<212> TYPE: PRT
<213> ORGANISM: Herpes viridae

<400> SEQUENCE: 17

Arg His Arg Asp Gly Val Arg Arg Pro Gln Lys Arg Pro Ser Cys
1               5                   10                  15

<210> SEQ ID NO 18
<211> LENGTH: 15
<212> TYPE: PRT
<213> ORGANISM: Herpes viridae

<400> SEQUENCE: 18

Gly Val Arg Arg Pro Gln Lys Arg Pro Ser Cys Ile Gly Cys Lys
1               5                   10                  15

<210> SEQ ID NO 19
<211> LENGTH: 15
<212> TYPE: PRT
<213> ORGANISM: Herpes viridae

<400> SEQUENCE: 19

Pro Gln Lys Arg Pro Ser Cys Ile Gly Cys Lys Gly Thr His Gly
1               5                   10                  15

<210> SEQ ID NO 20
<211> LENGTH: 15
<212> TYPE: PRT
<213> ORGANISM: Herpes viridae

<400> SEQUENCE: 20

Pro Ser Cys Ile Gly Cys Lys Gly Thr His Gly Gly Arg Gly Arg
1               5                   10                  15

<210> SEQ ID NO 21
<211> LENGTH: 15
<212> TYPE: PRT
<213> ORGANISM: Herpes viridae

<400> SEQUENCE: 21

Gly Cys Lys Gly Thr His Gly Gly Arg Gly Arg Gly Gly Ser Gly
1               5                   10                  15

<210> SEQ ID NO 22
<211> LENGTH: 15
<212> TYPE: PRT
<213> ORGANISM: Herpes viridae

<400> SEQUENCE: 22

Thr His Gly Gly Arg Gly Arg Gly Gly Ser Gly Gly Arg Arg Gly
1               5                   10                  15

<210> SEQ ID NO 23
<211> LENGTH: 15
<212> TYPE: PRT
<213> ORGANISM: Herpes viridae
```

<400> SEQUENCE: 23

Arg Gly Arg Gly Gly Ser Gly Gly Arg Gly Arg Gly Arg Gly Glu
1               5                   10                  15

<210> SEQ ID NO 24
<211> LENGTH: 15
<212> TYPE: PRT
<213> ORGANISM: Herpes viridae

<400> SEQUENCE: 24

Gly Ser Gly Gly Arg Arg Gly Arg Gly Arg Glu Arg Ala Arg Gly
1               5                   10                  15

<210> SEQ ID NO 25
<211> LENGTH: 15
<212> TYPE: PRT
<213> ORGANISM: Herpes viridae

<400> SEQUENCE: 25

Arg Arg Gly Arg Gly Arg Glu Arg Ala Arg Gly Gly Ser Arg Glu
1               5                   10                  15

<210> SEQ ID NO 26
<211> LENGTH: 15
<212> TYPE: PRT
<213> ORGANISM: Herpes viridae

<400> SEQUENCE: 26

Gly Arg Glu Arg Ala Arg Gly Gly Ser Arg Glu Arg Ala Arg Gly
1               5                   10                  15

<210> SEQ ID NO 27
<211> LENGTH: 15
<212> TYPE: PRT
<213> ORGANISM: Herpes viridae

<400> SEQUENCE: 27

Ala Arg Gly Gly Ser Arg Glu Arg Ala Arg Gly Arg Gly Arg Gly
1               5                   10                  15

<210> SEQ ID NO 28
<211> LENGTH: 15
<212> TYPE: PRT
<213> ORGANISM: Herpes viridae

<400> SEQUENCE: 28

Ser Arg Glu Arg Ala Arg Gly Arg Gly Arg Gly Arg Gly Glu Lys
1               5                   10                  15

<210> SEQ ID NO 29
<211> LENGTH: 15
<212> TYPE: PRT
<213> ORGANISM: Herpes viridae

<400> SEQUENCE: 29

Ala Arg Gly Arg Gly Arg Gly Arg Gly Glu Lys Arg Pro Arg Ser
1               5                   10                  15

<210> SEQ ID NO 30
<211> LENGTH: 15
<212> TYPE: PRT
<213> ORGANISM: Herpes viridae -continued

```
<400> SEQUENCE: 30

Gly Arg Gly Arg Gly Glu Lys Arg Pro Arg Ser Pro Ser Ser Gln
1               5                   10                  15

<210> SEQ ID NO 31
<211> LENGTH: 15
<212> TYPE: PRT
<213> ORGANISM: Herpes viridae

<400> SEQUENCE: 31

Gly Glu Lys Arg Pro Arg Ser Pro Ser Ser Gln Ser Ser Ser Ser
1               5                   10                  15

<210> SEQ ID NO 32
<211> LENGTH: 15
<212> TYPE: PRT
<213> ORGANISM: Herpes viridae

<400> SEQUENCE: 32

Pro Arg Ser Pro Ser Ser Gln Ser Ser Ser Ser Gly Ser Pro Pro
1               5                   10                  15

<210> SEQ ID NO 33
<211> LENGTH: 15
<212> TYPE: PRT
<213> ORGANISM: Herpes viridae

<400> SEQUENCE: 33

Ser Ser Gln Ser Ser Ser Ser Gly Ser Pro Pro Arg Arg Pro Pro
1               5                   10                  15

<210> SEQ ID NO 34
<211> LENGTH: 15
<212> TYPE: PRT
<213> ORGANISM: Herpes viridae

<400> SEQUENCE: 34

Ser Ser Ser Gly Ser Pro Pro Arg Arg Pro Pro Pro Gly Arg Arg
1               5                   10                  15

<210> SEQ ID NO 35
<211> LENGTH: 15
<212> TYPE: PRT
<213> ORGANISM: Herpes viridae

<400> SEQUENCE: 35

Ser Pro Pro Arg Arg Pro Pro Pro Gly Arg Arg Pro Phe Phe His
1               5                   10                  15

<210> SEQ ID NO 36
<211> LENGTH: 15
<212> TYPE: PRT
<213> ORGANISM: Herpes viridae

<400> SEQUENCE: 36

Arg Pro Pro Pro Gly Arg Arg Pro Phe Phe His Pro Val Gly Glu
1               5                   10                  15

<210> SEQ ID NO 37
<211> LENGTH: 15
<212> TYPE: PRT
<213> ORGANISM: Herpes viridae
```

```
<400> SEQUENCE: 37

Gly Arg Arg Pro Phe Phe His Pro Val Gly Glu Ala Asp Tyr Phe
1               5                   10                  15

<210> SEQ ID NO 38
<211> LENGTH: 15
<212> TYPE: PRT
<213> ORGANISM: Herpes viridae

<400> SEQUENCE: 38

Phe Phe His Pro Val Gly Glu Ala Asp Tyr Phe Glu Tyr His Gln
1               5                   10                  15

<210> SEQ ID NO 39
<211> LENGTH: 15
<212> TYPE: PRT
<213> ORGANISM: Herpes viridae

<400> SEQUENCE: 39

Val Gly Glu Ala Asp Tyr Phe Glu Tyr His Gln Glu Gly Gly Pro
1               5                   10                  15

<210> SEQ ID NO 40
<211> LENGTH: 15
<212> TYPE: PRT
<213> ORGANISM: Herpes viridae

<400> SEQUENCE: 40

Asp Tyr Phe Glu Tyr His Gln Glu Gly Gly Pro Asp Gly Glu Pro
1               5                   10                  15

<210> SEQ ID NO 41
<211> LENGTH: 15
<212> TYPE: PRT
<213> ORGANISM: Herpes viridae

<400> SEQUENCE: 41

Tyr His Gln Glu Gly Gly Pro Asp Gly Glu Pro Asp Val Pro Pro
1               5                   10                  15

<210> SEQ ID NO 42
<211> LENGTH: 15
<212> TYPE: PRT
<213> ORGANISM: Herpes viridae

<400> SEQUENCE: 42

Gly Gly Pro Asp Gly Glu Pro Asp Val Pro Pro Gly Ala Ile Glu
1               5                   10                  15

<210> SEQ ID NO 43
<211> LENGTH: 15
<212> TYPE: PRT
<213> ORGANISM: Herpes viridae

<400> SEQUENCE: 43

Gly Glu Pro Asp Val Pro Pro Gly Ala Ile Glu Gln Gly Pro Ala
1               5                   10                  15

<210> SEQ ID NO 44
<211> LENGTH: 15
<212> TYPE: PRT
<213> ORGANISM: Herpes viridae
```

-continued

<400> SEQUENCE: 44

Val Pro Pro Gly Ala Ile Glu Gln Gly Pro Ala Asp Asp Pro Gly
1               5                   10                  15

<210> SEQ ID NO 45
<211> LENGTH: 15
<212> TYPE: PRT
<213> ORGANISM: Herpes viridae

<400> SEQUENCE: 45

Ala Ile Glu Gln Gly Pro Ala Asp Asp Pro Gly Glu Gly Pro Ser
1               5                   10                  15

<210> SEQ ID NO 46
<211> LENGTH: 15
<212> TYPE: PRT
<213> ORGANISM: Herpes viridae

<400> SEQUENCE: 46

Gly Pro Ala Asp Asp Pro Gly Glu Gly Pro Ser Thr Gly Pro Arg
1               5                   10                  15

<210> SEQ ID NO 47
<211> LENGTH: 15
<212> TYPE: PRT
<213> ORGANISM: Herpes viridae

<400> SEQUENCE: 47

Asp Pro Gly Glu Gly Pro Ser Thr Gly Pro Arg Gly Gln Gly Asp
1               5                   10                  15

<210> SEQ ID NO 48
<211> LENGTH: 15
<212> TYPE: PRT
<213> ORGANISM: Herpes viridae

<400> SEQUENCE: 48

Gly Pro Ser Thr Gly Pro Arg Gly Gln Gly Asp Gly Gly Arg Arg
1               5                   10                  15

<210> SEQ ID NO 49
<211> LENGTH: 15
<212> TYPE: PRT
<213> ORGANISM: Herpes viridae

<400> SEQUENCE: 49

Gly Pro Arg Gly Gln Gly Asp Gly Gly Arg Arg Lys Lys Gly Gly
1               5                   10                  15

<210> SEQ ID NO 50
<211> LENGTH: 15
<212> TYPE: PRT
<213> ORGANISM: Herpes viridae

<400> SEQUENCE: 50

Gln Gly Asp Gly Gly Arg Arg Lys Lys Gly Gly Trp Phe Gly Lys
1               5                   10                  15

<210> SEQ ID NO 51
<211> LENGTH: 15
<212> TYPE: PRT
<213> ORGANISM: Herpes viridae

```
<400> SEQUENCE: 51

Gly Arg Arg Lys Lys Gly Gly Trp Phe Gly Lys His Arg Gly Gln
1               5                   10                  15

<210> SEQ ID NO 52
<211> LENGTH: 15
<212> TYPE: PRT
<213> ORGANISM: Herpes viridae

<400> SEQUENCE: 52

Lys Gly Gly Trp Phe Gly Lys His Arg Gly Gln Gly Gly Ser Asn
1               5                   10                  15

<210> SEQ ID NO 53
<211> LENGTH: 15
<212> TYPE: PRT
<213> ORGANISM: Herpes viridae

<400> SEQUENCE: 53

Phe Gly Lys His Arg Gly Gln Gly Gly Ser Asn Pro Lys Phe Glu
1               5                   10                  15

<210> SEQ ID NO 54
<211> LENGTH: 15
<212> TYPE: PRT
<213> ORGANISM: Herpes viridae

<400> SEQUENCE: 54

Arg Gly Gln Gly Gly Ser Asn Pro Lys Phe Glu Asn Ile Ala Glu
1               5                   10                  15

<210> SEQ ID NO 55
<211> LENGTH: 15
<212> TYPE: PRT
<213> ORGANISM: Herpes viridae

<400> SEQUENCE: 55

Gly Ser Asn Pro Lys Phe Glu Asn Ile Ala Glu Gly Leu Arg Ala
1               5                   10                  15

<210> SEQ ID NO 56
<211> LENGTH: 15
<212> TYPE: PRT
<213> ORGANISM: Herpes viridae

<400> SEQUENCE: 56

Lys Phe Glu Asn Ile Ala Glu Gly Leu Arg Ala Leu Leu Ala Arg
1               5                   10                  15

<210> SEQ ID NO 57
<211> LENGTH: 15
<212> TYPE: PRT
<213> ORGANISM: Herpes viridae

<400> SEQUENCE: 57

Ile Ala Glu Gly Leu Arg Ala Leu Leu Ala Arg Ser His Val Glu
1               5                   10                  15

<210> SEQ ID NO 58
<211> LENGTH: 15
<212> TYPE: PRT
<213> ORGANISM: Herpes viridae
```

```
<400> SEQUENCE: 58

Leu Arg Ala Leu Leu Ala Arg Ser His Val Glu Arg Thr Thr Asp
1               5                   10                  15

<210> SEQ ID NO 59
<211> LENGTH: 15
<212> TYPE: PRT
<213> ORGANISM: Herpes viridae

<400> SEQUENCE: 59

Leu Ala Arg Ser His Val Glu Arg Thr Thr Asp Glu Gly Thr Trp
1               5                   10                  15

<210> SEQ ID NO 60
<211> LENGTH: 15
<212> TYPE: PRT
<213> ORGANISM: Herpes viridae

<400> SEQUENCE: 60

His Val Glu Arg Thr Thr Asp Glu Gly Thr Trp Val Ala Gly Val
1               5                   10                  15

<210> SEQ ID NO 61
<211> LENGTH: 15
<212> TYPE: PRT
<213> ORGANISM: Herpes viridae

<400> SEQUENCE: 61

Thr Thr Asp Glu Gly Thr Trp Val Ala Gly Val Phe Val Tyr Gly
1               5                   10                  15

<210> SEQ ID NO 62
<211> LENGTH: 15
<212> TYPE: PRT
<213> ORGANISM: Herpes viridae

<400> SEQUENCE: 62

Gly Thr Trp Val Ala Gly Val Phe Val Tyr Gly Gly Ser Lys Thr
1               5                   10                  15

<210> SEQ ID NO 63
<211> LENGTH: 15
<212> TYPE: PRT
<213> ORGANISM: Herpes viridae

<400> SEQUENCE: 63

Ala Gly Val Phe Val Tyr Gly Gly Ser Lys Thr Ser Leu Tyr Asn
1               5                   10                  15

<210> SEQ ID NO 64
<211> LENGTH: 15
<212> TYPE: PRT
<213> ORGANISM: Herpes viridae

<400> SEQUENCE: 64

Val Tyr Gly Gly Ser Lys Thr Ser Leu Tyr Asn Leu Arg Arg Gly
1               5                   10                  15

<210> SEQ ID NO 65
<211> LENGTH: 15
<212> TYPE: PRT
<213> ORGANISM: Herpes viridae
```

```
<400> SEQUENCE: 65

Ser Lys Thr Ser Leu Tyr Asn Leu Arg Arg Gly Thr Ala Leu Ala
1               5                   10                  15

<210> SEQ ID NO 66
<211> LENGTH: 15
<212> TYPE: PRT
<213> ORGANISM: Herpes viridae

<400> SEQUENCE: 66

Leu Tyr Asn Leu Arg Arg Gly Thr Ala Leu Ala Ile Pro Gln Cys
1               5                   10                  15

<210> SEQ ID NO 67
<211> LENGTH: 15
<212> TYPE: PRT
<213> ORGANISM: Herpes viridae

<400> SEQUENCE: 67

Arg Arg Gly Thr Ala Leu Ala Ile Pro Gln Cys Arg Leu Thr Pro
1               5                   10                  15

<210> SEQ ID NO 68
<211> LENGTH: 15
<212> TYPE: PRT
<213> ORGANISM: Herpes viridae

<400> SEQUENCE: 68

Ala Leu Ala Ile Pro Gln Cys Arg Leu Thr Pro Leu Ser Arg Leu
1               5                   10                  15

<210> SEQ ID NO 69
<211> LENGTH: 15
<212> TYPE: PRT
<213> ORGANISM: Herpes viridae

<400> SEQUENCE: 69

Pro Gln Cys Arg Leu Thr Pro Leu Ser Arg Leu Pro Phe Gly Met
1               5                   10                  15

<210> SEQ ID NO 70
<211> LENGTH: 15
<212> TYPE: PRT
<213> ORGANISM: Herpes viridae

<400> SEQUENCE: 70

Leu Thr Pro Leu Ser Arg Leu Pro Phe Gly Met Ala Pro Gly Pro
1               5                   10                  15

<210> SEQ ID NO 71
<211> LENGTH: 15
<212> TYPE: PRT
<213> ORGANISM: Herpes viridae

<400> SEQUENCE: 71

Ser Arg Leu Pro Phe Gly Met Ala Pro Gly Pro Gly Pro Gln Pro
1               5                   10                  15

<210> SEQ ID NO 72
<211> LENGTH: 15
<212> TYPE: PRT
<213> ORGANISM: Herpes viridae
```

-continued

```
<400> SEQUENCE: 72

Phe Gly Met Ala Pro Gly Pro Gln Pro Gly Pro Leu Arg
1               5                   10                  15

<210> SEQ ID NO 73
<211> LENGTH: 15
<212> TYPE: PRT
<213> ORGANISM: Herpes viridae

<400> SEQUENCE: 73

Pro Gly Pro Gly Pro Gln Pro Gly Pro Leu Arg Glu Ser Ile Val
1               5                   10                  15

<210> SEQ ID NO 74
<211> LENGTH: 15
<212> TYPE: PRT
<213> ORGANISM: Herpes viridae

<400> SEQUENCE: 74

Pro Gln Pro Gly Pro Leu Arg Glu Ser Ile Val Cys Tyr Phe Met
1               5                   10                  15

<210> SEQ ID NO 75
<211> LENGTH: 15
<212> TYPE: PRT
<213> ORGANISM: Herpes viridae

<400> SEQUENCE: 75

Pro Leu Arg Glu Ser Ile Val Cys Tyr Phe Met Val Phe Leu Gln
1               5                   10                  15

<210> SEQ ID NO 76
<211> LENGTH: 15
<212> TYPE: PRT
<213> ORGANISM: Herpes viridae

<400> SEQUENCE: 76

Ser Ile Val Cys Tyr Phe Met Val Phe Leu Gln Thr His Ile Phe
1               5                   10                  15

<210> SEQ ID NO 77
<211> LENGTH: 15
<212> TYPE: PRT
<213> ORGANISM: Herpes viridae

<400> SEQUENCE: 77

Tyr Phe Met Val Phe Leu Gln Thr His Ile Phe Ala Glu Val Leu
1               5                   10                  15

<210> SEQ ID NO 78
<211> LENGTH: 15
<212> TYPE: PRT
<213> ORGANISM: Herpes viridae

<400> SEQUENCE: 78

Phe Leu Gln Thr His Ile Phe Ala Glu Val Leu Lys Asp Ala Ile
1               5                   10                  15

<210> SEQ ID NO 79
<211> LENGTH: 15
<212> TYPE: PRT
<213> ORGANISM: Herpes viridae
```

-continued

```
<400> SEQUENCE: 79

His Ile Phe Ala Glu Val Leu Lys Asp Ala Ile Lys Asp Leu Val
1               5                   10                  15

<210> SEQ ID NO 80
<211> LENGTH: 15
<212> TYPE: PRT
<213> ORGANISM: Herpes viridae

<400> SEQUENCE: 80

Glu Val Leu Lys Asp Ala Ile Lys Asp Leu Val Met Thr Lys Pro
1               5                   10                  15

<210> SEQ ID NO 81
<211> LENGTH: 15
<212> TYPE: PRT
<213> ORGANISM: Herpes viridae

<400> SEQUENCE: 81

Asp Ala Ile Lys Asp Leu Val Met Thr Lys Pro Ala Pro Thr Cys
1               5                   10                  15

<210> SEQ ID NO 82
<211> LENGTH: 15
<212> TYPE: PRT
<213> ORGANISM: Herpes viridae

<400> SEQUENCE: 82

Asp Leu Val Met Thr Lys Pro Ala Pro Thr Cys Asn Ile Arg Val
1               5                   10                  15

<210> SEQ ID NO 83
<211> LENGTH: 15
<212> TYPE: PRT
<213> ORGANISM: Herpes viridae

<400> SEQUENCE: 83

Thr Lys Pro Ala Pro Thr Cys Asn Ile Arg Val Thr Val Cys Ser
1               5                   10                  15

<210> SEQ ID NO 84
<211> LENGTH: 15
<212> TYPE: PRT
<213> ORGANISM: Herpes viridae

<400> SEQUENCE: 84

Pro Thr Cys Asn Ile Arg Val Thr Val Cys Ser Phe Asp Asp Gly
1               5                   10                  15

<210> SEQ ID NO 85
<211> LENGTH: 15
<212> TYPE: PRT
<213> ORGANISM: Herpes viridae

<400> SEQUENCE: 85

Ile Arg Val Thr Val Cys Ser Phe Asp Asp Gly Val Asp Leu Pro
1               5                   10                  15

<210> SEQ ID NO 86
<211> LENGTH: 15
<212> TYPE: PRT
<213> ORGANISM: Herpes viridae
```

```
<400> SEQUENCE: 86

Val Cys Ser Phe Asp Asp Gly Val Asp Leu Pro Pro Trp Phe Pro
1               5                   10                  15

<210> SEQ ID NO 87
<211> LENGTH: 15
<212> TYPE: PRT
<213> ORGANISM: Herpes viridae

<400> SEQUENCE: 87

Asp Asp Gly Val Asp Leu Pro Pro Trp Phe Pro Pro Met Val Glu
1               5                   10                  15

<210> SEQ ID NO 88
<211> LENGTH: 15
<212> TYPE: PRT
<213> ORGANISM: Herpes viridae

<400> SEQUENCE: 88

Asp Leu Pro Pro Trp Phe Pro Pro Met Val Glu Gly Ala Ala Ala
1               5                   10                  15

<210> SEQ ID NO 89
<211> LENGTH: 15
<212> TYPE: PRT
<213> ORGANISM: Herpes viridae

<400> SEQUENCE: 89

Trp Phe Pro Pro Met Val Glu Gly Ala Ala Ala Glu Gly Asp Asp
1               5                   10                  15

<210> SEQ ID NO 90
<211> LENGTH: 15
<212> TYPE: PRT
<213> ORGANISM: Herpes viridae

<400> SEQUENCE: 90

Met Val Glu Gly Ala Ala Ala Glu Gly Asp Asp Gly Asp Asp Gly
1               5                   10                  15

<210> SEQ ID NO 91
<211> LENGTH: 15
<212> TYPE: PRT
<213> ORGANISM: Herpes viridae

<400> SEQUENCE: 91

Ala Ala Ala Glu Gly Asp Asp Gly Asp Asp Gly Asp Glu Gly Gly
1               5                   10                  15

<210> SEQ ID NO 92
<211> LENGTH: 15
<212> TYPE: PRT
<213> ORGANISM: Herpes viridae

<400> SEQUENCE: 92

Gly Asp Asp Gly Asp Asp Gly Asp Glu Gly Gly Asp Gly Asp Glu
1               5                   10                  15

<210> SEQ ID NO 93
<211> LENGTH: 15
<212> TYPE: PRT
<213> ORGANISM: Herpes viridae
```

<400> SEQUENCE: 93

Asp Asp Gly Asp Glu Gly Gly Asp Gly Asp Glu Gly Glu Glu Gly
1               5                   10                  15

<210> SEQ ID NO 94
<211> LENGTH: 13
<212> TYPE: PRT
<213> ORGANISM: Herpes viridae

<400> SEQUENCE: 94

Glu Gly Gly Asp Gly Asp Glu Gly Glu Glu Gly Gln Glu
1               5                   10

<210> SEQ ID NO 95
<211> LENGTH: 15
<212> TYPE: PRT
<213> ORGANISM: Herpes viridae

<400> SEQUENCE: 95

Met Glu His Asp Leu Glu Arg Gly Pro Pro Gly Pro Arg Arg Pro
1               5                   10                  15

<210> SEQ ID NO 96
<211> LENGTH: 15
<212> TYPE: PRT
<213> ORGANISM: Herpes viridae

<400> SEQUENCE: 96

Leu Glu Arg Gly Pro Pro Gly Pro Arg Arg Pro Pro Arg Gly Pro
1               5                   10                  15

<210> SEQ ID NO 97
<211> LENGTH: 15
<212> TYPE: PRT
<213> ORGANISM: Herpes viridae

<400> SEQUENCE: 97

Pro Pro Gly Pro Arg Arg Pro Pro Arg Gly Pro Pro Leu Ser Ser
1               5                   10                  15

<210> SEQ ID NO 98
<211> LENGTH: 15
<212> TYPE: PRT
<213> ORGANISM: Herpes viridae

<400> SEQUENCE: 98

Arg Arg Pro Pro Arg Gly Pro Pro Leu Ser Ser Ser Leu Gly Leu
1               5                   10                  15

<210> SEQ ID NO 99
<211> LENGTH: 15
<212> TYPE: PRT
<213> ORGANISM: Herpes viridae

<400> SEQUENCE: 99

Leu Phe Trp Leu Tyr Ile Val Met Ser Asp Trp Thr Gly Gly Ala
1               5                   10                  15

<210> SEQ ID NO 100
<211> LENGTH: 15
<212> TYPE: PRT
<213> ORGANISM: Herpes viridae

```
<400> SEQUENCE: 100

Tyr Ile Val Met Ser Asp Trp Thr Gly Gly Ala Leu Leu Val Leu
1               5                   10                  15

<210> SEQ ID NO 101
<211> LENGTH: 15
<212> TYPE: PRT
<213> ORGANISM: Herpes viridae

<400> SEQUENCE: 101

Ser Asp Trp Thr Gly Gly Ala Leu Leu Val Leu Tyr Ser Phe Ala
1               5                   10                  15

<210> SEQ ID NO 102
<211> LENGTH: 15
<212> TYPE: PRT
<213> ORGANISM: Herpes viridae

<400> SEQUENCE: 102

Gly Gly Ala Leu Leu Val Leu Tyr Ser Phe Ala Leu Met Leu Ile
1               5                   10                  15

<210> SEQ ID NO 103
<211> LENGTH: 15
<212> TYPE: PRT
<213> ORGANISM: Herpes viridae

<400> SEQUENCE: 103

Leu Val Leu Tyr Ser Phe Ala Leu Met Leu Ile Ile Ile Ile Leu
1               5                   10                  15

<210> SEQ ID NO 104
<211> LENGTH: 15
<212> TYPE: PRT
<213> ORGANISM: Herpes viridae

<400> SEQUENCE: 104

Ser Phe Ala Leu Met Leu Ile Ile Ile Ile Leu Ile Ile Phe Ile
1               5                   10                  15

<210> SEQ ID NO 105
<211> LENGTH: 15
<212> TYPE: PRT
<213> ORGANISM: Herpes viridae

<400> SEQUENCE: 105

Met Leu Ile Ile Ile Ile Leu Ile Ile Phe Ile Phe Arg Arg Asp
1               5                   10                  15

<210> SEQ ID NO 106
<211> LENGTH: 15
<212> TYPE: PRT
<213> ORGANISM: Herpes viridae

<400> SEQUENCE: 106

Ile Ile Leu Ile Ile Phe Ile Phe Arg Arg Asp Leu Leu Cys Pro
1               5                   10                  15

<210> SEQ ID NO 107
<211> LENGTH: 15
<212> TYPE: PRT
<213> ORGANISM: Herpes viridae
```

```
<400> SEQUENCE: 107

Ile Phe Ile Phe Arg Arg Asp Leu Leu Cys Pro Leu Gly Ala Leu
1               5                   10                  15

<210> SEQ ID NO 108
<211> LENGTH: 15
<212> TYPE: PRT
<213> ORGANISM: Herpes viridae

<400> SEQUENCE: 108

Arg Arg Asp Leu Leu Cys Pro Leu Gly Ala Leu Cys Ile Leu Leu
1               5                   10                  15

<210> SEQ ID NO 109
<211> LENGTH: 15
<212> TYPE: PRT
<213> ORGANISM: Herpes viridae

<400> SEQUENCE: 109

Leu Cys Pro Leu Gly Ala Leu Cys Ile Leu Leu Met Ile Thr
1               5                   10                  15

<210> SEQ ID NO 110
<211> LENGTH: 15
<212> TYPE: PRT
<213> ORGANISM: Herpes viridae

<400> SEQUENCE: 110

Gly Ala Leu Cys Ile Leu Leu Met Ile Thr Leu Leu Ile
1               5                   10                  15

<210> SEQ ID NO 111
<211> LENGTH: 15
<212> TYPE: PRT
<213> ORGANISM: Herpes viridae

<400> SEQUENCE: 111

Ile Leu Leu Leu Met Ile Thr Leu Leu Ile Ala Leu Trp Asn
1               5                   10                  15

<210> SEQ ID NO 112
<211> LENGTH: 15
<212> TYPE: PRT
<213> ORGANISM: Herpes viridae

<400> SEQUENCE: 112

Met Ile Thr Leu Leu Leu Ile Ala Leu Trp Asn Leu His Gly Gln
1               5                   10                  15

<210> SEQ ID NO 113
<211> LENGTH: 15
<212> TYPE: PRT
<213> ORGANISM: Herpes viridae

<400> SEQUENCE: 113

Leu Leu Ile Ala Leu Trp Asn Leu His Gly Gln Ala Leu Tyr Leu
1               5                   10                  15

<210> SEQ ID NO 114
<211> LENGTH: 15
<212> TYPE: PRT
<213> ORGANISM: Herpes viridae
```

```
<400> SEQUENCE: 114

Leu Trp Asn Leu His Gly Gln Ala Leu Tyr Leu Gly Ile Val Leu
1               5                   10                  15

<210> SEQ ID NO 115
<211> LENGTH: 15
<212> TYPE: PRT
<213> ORGANISM: Herpes viridae

<400> SEQUENCE: 115

His Gly Gln Ala Leu Tyr Leu Gly Ile Val Leu Phe Ile Phe Gly
1               5                   10                  15

<210> SEQ ID NO 116
<211> LENGTH: 15
<212> TYPE: PRT
<213> ORGANISM: Herpes viridae

<400> SEQUENCE: 116

Leu Tyr Leu Gly Ile Val Leu Phe Ile Phe Gly Cys Leu Leu Val
1               5                   10                  15

<210> SEQ ID NO 117
<211> LENGTH: 15
<212> TYPE: PRT
<213> ORGANISM: Herpes viridae

<400> SEQUENCE: 117

Ile Val Leu Phe Ile Phe Gly Cys Leu Leu Val Leu Gly Leu Trp
1               5                   10                  15

<210> SEQ ID NO 118
<211> LENGTH: 15
<212> TYPE: PRT
<213> ORGANISM: Herpes viridae

<400> SEQUENCE: 118

Ile Phe Gly Cys Leu Leu Val Leu Gly Leu Trp Ile Tyr Leu Leu
1               5                   10                  15

<210> SEQ ID NO 119
<211> LENGTH: 15
<212> TYPE: PRT
<213> ORGANISM: Herpes viridae

<400> SEQUENCE: 119

Leu Leu Val Leu Gly Leu Trp Ile Tyr Leu Leu Glu Ile Leu Trp
1               5                   10                  15

<210> SEQ ID NO 120
<211> LENGTH: 15
<212> TYPE: PRT
<213> ORGANISM: Herpes viridae

<400> SEQUENCE: 120

Gly Leu Trp Ile Tyr Leu Leu Glu Ile Leu Trp Arg Leu Gly Ala
1               5                   10                  15

<210> SEQ ID NO 121
<211> LENGTH: 15
<212> TYPE: PRT
<213> ORGANISM: Herpes viridae
```

```
<400> SEQUENCE: 121

Tyr Leu Leu Glu Ile Leu Trp Arg Leu Gly Ala Thr Ile Trp Gln
1               5                   10                  15

<210> SEQ ID NO 122
<211> LENGTH: 15
<212> TYPE: PRT
<213> ORGANISM: Herpes viridae

<400> SEQUENCE: 122

Ile Leu Trp Arg Leu Gly Ala Thr Ile Trp Gln Leu Leu Ala Phe
1               5                   10                  15

<210> SEQ ID NO 123
<211> LENGTH: 15
<212> TYPE: PRT
<213> ORGANISM: Herpes viridae

<400> SEQUENCE: 123

Leu Gly Ala Thr Ile Trp Gln Leu Leu Ala Phe Phe Leu Ala Phe
1               5                   10                  15

<210> SEQ ID NO 124
<211> LENGTH: 15
<212> TYPE: PRT
<213> ORGANISM: Herpes viridae

<400> SEQUENCE: 124

Ile Trp Gln Leu Leu Ala Phe Phe Leu Ala Phe Phe Leu Asp Leu
1               5                   10                  15

<210> SEQ ID NO 125
<211> LENGTH: 15
<212> TYPE: PRT
<213> ORGANISM: Herpes viridae

<400> SEQUENCE: 125

Leu Ala Phe Phe Leu Ala Phe Phe Leu Asp Leu Ile Leu Leu Ile
1               5                   10                  15

<210> SEQ ID NO 126
<211> LENGTH: 15
<212> TYPE: PRT
<213> ORGANISM: Herpes viridae

<400> SEQUENCE: 126

Leu Ala Phe Phe Leu Asp Leu Ile Leu Leu Ile Ile Ala Leu Tyr
1               5                   10                  15

<210> SEQ ID NO 127
<211> LENGTH: 15
<212> TYPE: PRT
<213> ORGANISM: Herpes viridae

<400> SEQUENCE: 127

Leu Asp Leu Ile Leu Leu Ile Ile Ala Leu Tyr Leu Gln Gln Asn
1               5                   10                  15

<210> SEQ ID NO 128
<211> LENGTH: 15
<212> TYPE: PRT
<213> ORGANISM: Herpes viridae
```

```
<400> SEQUENCE: 128

Leu Leu Ile Ile Ala Leu Tyr Leu Gln Gln Asn Trp Trp Thr Leu
1               5                   10                  15

<210> SEQ ID NO 129
<211> LENGTH: 15
<212> TYPE: PRT
<213> ORGANISM: Herpes viridae

<400> SEQUENCE: 129

Ala Leu Tyr Leu Gln Gln Asn Trp Trp Thr Leu Leu Val Asp Leu
1               5                   10                  15

<210> SEQ ID NO 130
<211> LENGTH: 15
<212> TYPE: PRT
<213> ORGANISM: Herpes viridae

<400> SEQUENCE: 130

Gln Gln Asn Trp Trp Thr Leu Leu Val Asp Leu Leu Trp Leu Leu
1               5                   10                  15

<210> SEQ ID NO 131
<211> LENGTH: 15
<212> TYPE: PRT
<213> ORGANISM: Herpes viridae

<400> SEQUENCE: 131

Trp Thr Leu Leu Val Asp Leu Leu Trp Leu Leu Leu Phe Leu Ala
1               5                   10                  15

<210> SEQ ID NO 132
<211> LENGTH: 15
<212> TYPE: PRT
<213> ORGANISM: Herpes viridae

<400> SEQUENCE: 132

Val Asp Leu Leu Trp Leu Leu Leu Phe Leu Ala Ile Leu Ile Trp
1               5                   10                  15

<210> SEQ ID NO 133
<211> LENGTH: 15
<212> TYPE: PRT
<213> ORGANISM: Herpes viridae

<400> SEQUENCE: 133

Trp Leu Leu Leu Phe Leu Ala Ile Leu Ile Trp Met Tyr Tyr His
1               5                   10                  15

<210> SEQ ID NO 134
<211> LENGTH: 15
<212> TYPE: PRT
<213> ORGANISM: Herpes viridae

<400> SEQUENCE: 134

Phe Leu Ala Ile Leu Ile Trp Met Tyr Tyr His Gly Gln Arg His
1               5                   10                  15

<210> SEQ ID NO 135
<211> LENGTH: 15
<212> TYPE: PRT
<213> ORGANISM: Herpes viridae
```

```
<400> SEQUENCE: 135

Leu Ile Trp Met Tyr Tyr His Gly Gln Arg His Ser Asp Glu His
1               5                   10                  15

<210> SEQ ID NO 136
<211> LENGTH: 15
<212> TYPE: PRT
<213> ORGANISM: Herpes viridae

<400> SEQUENCE: 136

Tyr Tyr His Gly Gln Arg His Ser Asp Glu His His His Asp Asp
1               5                   10                  15

<210> SEQ ID NO 137
<211> LENGTH: 15
<212> TYPE: PRT
<213> ORGANISM: Herpes viridae

<400> SEQUENCE: 137

Gln Arg His Ser Asp Glu His His His Asp Asp Ser Leu Pro His
1               5                   10                  15

<210> SEQ ID NO 138
<211> LENGTH: 15
<212> TYPE: PRT
<213> ORGANISM: Herpes viridae

<400> SEQUENCE: 138

Asp Glu His His His Asp Asp Ser Leu Pro His Pro Gln Gln Ala
1               5                   10                  15

<210> SEQ ID NO 139
<211> LENGTH: 15
<212> TYPE: PRT
<213> ORGANISM: Herpes viridae

<400> SEQUENCE: 139

His Asp Asp Ser Leu Pro His Pro Gln Gln Ala Thr Asp Asp Ser
1               5                   10                  15

<210> SEQ ID NO 140
<211> LENGTH: 15
<212> TYPE: PRT
<213> ORGANISM: Herpes viridae

<400> SEQUENCE: 140

Leu Pro His Pro Gln Gln Ala Thr Asp Asp Ser Gly His Glu Ser
1               5                   10                  15

<210> SEQ ID NO 141
<211> LENGTH: 15
<212> TYPE: PRT
<213> ORGANISM: Herpes viridae

<400> SEQUENCE: 141

Gln Gln Ala Thr Asp Asp Ser Gly His Glu Ser Asp Ser Asn Ser
1               5                   10                  15

<210> SEQ ID NO 142
<211> LENGTH: 15
<212> TYPE: PRT
<213> ORGANISM: Herpes viridae
```

<400> SEQUENCE: 142

Asp Asp Ser Gly His Glu Ser Asp Ser Asn Ser Asn Glu Gly Arg
1               5                   10                  15

<210> SEQ ID NO 143
<211> LENGTH: 15
<212> TYPE: PRT
<213> ORGANISM: Herpes viridae

<400> SEQUENCE: 143

His Glu Ser Asp Ser Asn Ser Asn Glu Gly Arg His His Leu Leu
1               5                   10                  15

<210> SEQ ID NO 144
<211> LENGTH: 15
<212> TYPE: PRT
<213> ORGANISM: Herpes viridae

<400> SEQUENCE: 144

Ser Asn Ser Asn Glu Gly Arg His His Leu Leu Val Ser Gly Ala
1               5                   10                  15

<210> SEQ ID NO 145
<211> LENGTH: 15
<212> TYPE: PRT
<213> ORGANISM: Herpes viridae

<400> SEQUENCE: 145

Glu Gly Arg His His Leu Leu Val Ser Gly Ala Gly Asp Gly Pro
1               5                   10                  15

<210> SEQ ID NO 146
<211> LENGTH: 15
<212> TYPE: PRT
<213> ORGANISM: Herpes viridae

<400> SEQUENCE: 146

His Leu Leu Val Ser Gly Ala Gly Asp Gly Pro Pro Leu Cys Ser
1               5                   10                  15

<210> SEQ ID NO 147
<211> LENGTH: 15
<212> TYPE: PRT
<213> ORGANISM: Herpes viridae

<400> SEQUENCE: 147

Ser Gly Ala Gly Asp Gly Pro Pro Leu Cys Ser Gln Asn Leu Gly
1               5                   10                  15

<210> SEQ ID NO 148
<211> LENGTH: 15
<212> TYPE: PRT
<213> ORGANISM: Herpes viridae

<400> SEQUENCE: 148

Asp Gly Pro Pro Leu Cys Ser Gln Asn Leu Gly Ala Pro Gly Gly
1               5                   10                  15

<210> SEQ ID NO 149
<211> LENGTH: 15
<212> TYPE: PRT
<213> ORGANISM: Herpes viridae

```
<400> SEQUENCE: 149

Leu Cys Ser Gln Asn Leu Gly Ala Pro Gly Gly Gly Pro Asp Asn
1               5                   10                  15

<210> SEQ ID NO 150
<211> LENGTH: 15
<212> TYPE: PRT
<213> ORGANISM: Herpes viridae

<400> SEQUENCE: 150

Asn Leu Gly Ala Pro Gly Gly Gly Pro Asp Asn Gly Pro Gln Asp
1               5                   10                  15

<210> SEQ ID NO 151
<211> LENGTH: 15
<212> TYPE: PRT
<213> ORGANISM: Herpes viridae

<400> SEQUENCE: 151

Pro Gly Gly Gly Pro Asp Asn Gly Pro Gln Asp Pro Asp Asn Thr
1               5                   10                  15

<210> SEQ ID NO 152
<211> LENGTH: 15
<212> TYPE: PRT
<213> ORGANISM: Herpes viridae

<400> SEQUENCE: 152

Pro Asp Asn Gly Pro Gln Asp Pro Asp Asn Thr Asp Asp Asn Gly
1               5                   10                  15

<210> SEQ ID NO 153
<211> LENGTH: 15
<212> TYPE: PRT
<213> ORGANISM: Herpes viridae

<400> SEQUENCE: 153

Pro Gln Asp Pro Asp Asn Thr Asp Asn Gly Pro Gln Asp Pro
1               5                   10                  15

<210> SEQ ID NO 154
<211> LENGTH: 15
<212> TYPE: PRT
<213> ORGANISM: Herpes viridae

<400> SEQUENCE: 154

Asp Asn Thr Asp Asp Asn Gly Pro Gln Asp Pro Asp Asn Thr Asp
1               5                   10                  15

<210> SEQ ID NO 155
<211> LENGTH: 15
<212> TYPE: PRT
<213> ORGANISM: Herpes viridae

<400> SEQUENCE: 155

Asp Asn Gly Pro Gln Asp Pro Asp Asn Thr Asp Asn Gly Pro
1               5                   10                  15

<210> SEQ ID NO 156
<211> LENGTH: 15
<212> TYPE: PRT
<213> ORGANISM: Herpes viridae
```

<400> SEQUENCE: 156

Gln Asp Pro Asp Asn Thr Asp Asp Asn Gly Pro His Asp Pro Leu
1               5                   10                  15

<210> SEQ ID NO 157
<211> LENGTH: 15
<212> TYPE: PRT
<213> ORGANISM: Herpes viridae

<400> SEQUENCE: 157

Asn Thr Asp Asp Asn Gly Pro His Asp Pro Leu Pro His Ser Pro
1               5                   10                  15

<210> SEQ ID NO 158
<211> LENGTH: 15
<212> TYPE: PRT
<213> ORGANISM: Herpes viridae

<400> SEQUENCE: 158

Asn Gly Pro His Asp Pro Leu Pro His Ser Pro Ser Asp Ser Ala
1               5                   10                  15

<210> SEQ ID NO 159
<211> LENGTH: 15
<212> TYPE: PRT
<213> ORGANISM: Herpes viridae

<400> SEQUENCE: 159

Asp Pro Leu Pro His Ser Pro Ser Asp Ser Ala Gly Asn Asp Gly
1               5                   10                  15

<210> SEQ ID NO 160
<211> LENGTH: 15
<212> TYPE: PRT
<213> ORGANISM: Herpes viridae

<400> SEQUENCE: 160

His Ser Pro Ser Asp Ser Ala Gly Asn Asp Gly Gly Pro Pro Gln
1               5                   10                  15

<210> SEQ ID NO 161
<211> LENGTH: 15
<212> TYPE: PRT
<213> ORGANISM: Herpes viridae

<400> SEQUENCE: 161

Asp Ser Ala Gly Asn Asp Gly Gly Pro Pro Gln Leu Thr Glu Glu
1               5                   10                  15

<210> SEQ ID NO 162
<211> LENGTH: 15
<212> TYPE: PRT
<213> ORGANISM: Herpes viridae

<400> SEQUENCE: 162

Asn Asp Gly Gly Pro Pro Gln Leu Thr Glu Glu Val Glu Asn Lys
1               5                   10                  15

<210> SEQ ID NO 163
<211> LENGTH: 15
<212> TYPE: PRT
<213> ORGANISM: Herpes viridae -continued

<400> SEQUENCE: 163

Pro Pro Gln Leu Thr Glu Glu Val Glu Asn Lys Gly Gly Asp Gln
1               5                   10                  15

<210> SEQ ID NO 164
<211> LENGTH: 15
<212> TYPE: PRT
<213> ORGANISM: Herpes viridae

<400> SEQUENCE: 164

Thr Glu Glu Val Glu Asn Lys Gly Gly Asp Gln Gly Pro Pro Leu
1               5                   10                  15

<210> SEQ ID NO 165
<211> LENGTH: 15
<212> TYPE: PRT
<213> ORGANISM: Herpes viridae

<400> SEQUENCE: 165

Glu Asn Lys Gly Gly Asp Gln Gly Pro Pro Leu Met Thr Asp Gly
1               5                   10                  15

<210> SEQ ID NO 166
<211> LENGTH: 15
<212> TYPE: PRT
<213> ORGANISM: Herpes viridae

<400> SEQUENCE: 166

Gly Asp Gln Gly Pro Pro Leu Met Thr Asp Gly Gly Gly Gly His
1               5                   10                  15

<210> SEQ ID NO 167
<211> LENGTH: 15
<212> TYPE: PRT
<213> ORGANISM: Herpes viridae

<400> SEQUENCE: 167

Pro Pro Leu Met Thr Asp Gly Gly Gly Gly His Ser His Asp Ser
1               5                   10                  15

<210> SEQ ID NO 168
<211> LENGTH: 15
<212> TYPE: PRT
<213> ORGANISM: Herpes viridae

<400> SEQUENCE: 168

Thr Asp Gly Gly Gly Gly His Ser His Asp Ser Gly His Gly Gly
1               5                   10                  15

<210> SEQ ID NO 169
<211> LENGTH: 15
<212> TYPE: PRT
<213> ORGANISM: Herpes viridae

<400> SEQUENCE: 169

Gly Gly His Ser His Asp Ser Gly His Gly Gly Asp Pro His
1               5                   10                  15

<210> SEQ ID NO 170
<211> LENGTH: 15
<212> TYPE: PRT
<213> ORGANISM: Herpes viridae

```
<400> SEQUENCE: 170

His Asp Ser Gly His Gly Gly Asp Pro His Leu Pro Thr Leu
1               5                   10                  15

<210> SEQ ID NO 171
<211> LENGTH: 15
<212> TYPE: PRT
<213> ORGANISM: Herpes viridae

<400> SEQUENCE: 171

His Gly Gly Gly Asp Pro His Leu Pro Thr Leu Leu Leu Gly Ser
1               5                   10                  15

<210> SEQ ID NO 172
<211> LENGTH: 15
<212> TYPE: PRT
<213> ORGANISM: Herpes viridae

<400> SEQUENCE: 172

Asp Pro His Leu Pro Thr Leu Leu Leu Gly Ser Ser Gly Ser Gly
1               5                   10                  15

<210> SEQ ID NO 173
<211> LENGTH: 15
<212> TYPE: PRT
<213> ORGANISM: Herpes viridae

<400> SEQUENCE: 173

Pro Thr Leu Leu Leu Gly Ser Ser Gly Ser Gly Gly Asp Asp Asp
1               5                   10                  15

<210> SEQ ID NO 174
<211> LENGTH: 15
<212> TYPE: PRT
<213> ORGANISM: Herpes viridae

<400> SEQUENCE: 174

Leu Gly Ser Ser Gly Ser Gly Gly Asp Asp Asp Asp Pro His Gly
1               5                   10                  15

<210> SEQ ID NO 175
<211> LENGTH: 15
<212> TYPE: PRT
<213> ORGANISM: Herpes viridae

<400> SEQUENCE: 175

Gly Ser Gly Gly Asp Asp Asp Asp Pro His Gly Pro Val Gln Leu
1               5                   10                  15

<210> SEQ ID NO 176
<211> LENGTH: 15
<212> TYPE: PRT
<213> ORGANISM: Herpes viridae

<400> SEQUENCE: 176

Asp Asp Asp Asp Pro His Gly Pro Val Gln Leu Ser Tyr Tyr Asp
1               5                   10                  15

<210> SEQ ID NO 177
<211> LENGTH: 15
<212> TYPE: PRT
<213> ORGANISM: Herpes viridae
```

```
<400> SEQUENCE: 177

Met Gly Ser Leu Glu Met Val Pro Met Gly Ala Gly Pro Pro Ser
1               5                   10                  15

<210> SEQ ID NO 178
<211> LENGTH: 15
<212> TYPE: PRT
<213> ORGANISM: Herpes viridae

<400> SEQUENCE: 178

Glu Met Val Pro Met Gly Ala Gly Pro Pro Ser Pro Gly Gly Asp
1               5                   10                  15

<210> SEQ ID NO 179
<211> LENGTH: 15
<212> TYPE: PRT
<213> ORGANISM: Herpes viridae

<400> SEQUENCE: 179

Met Gly Ala Gly Pro Pro Ser Pro Gly Gly Asp Pro Asp Gly Tyr
1               5                   10                  15

<210> SEQ ID NO 180
<211> LENGTH: 15
<212> TYPE: PRT
<213> ORGANISM: Herpes viridae

<400> SEQUENCE: 180

Pro Pro Ser Pro Gly Gly Asp Pro Asp Gly Tyr Asp Gly Gly Asn
1               5                   10                  15

<210> SEQ ID NO 181
<211> LENGTH: 15
<212> TYPE: PRT
<213> ORGANISM: Herpes viridae

<400> SEQUENCE: 181

Gly Gly Asp Pro Asp Gly Tyr Asp Gly Gly Asn Asn Ser Gln Tyr
1               5                   10                  15

<210> SEQ ID NO 182
<211> LENGTH: 15
<212> TYPE: PRT
<213> ORGANISM: Herpes viridae

<400> SEQUENCE: 182

Asp Gly Tyr Asp Gly Gly Asn Asn Ser Gln Tyr Pro Ser Ala Ser
1               5                   10                  15

<210> SEQ ID NO 183
<211> LENGTH: 15
<212> TYPE: PRT
<213> ORGANISM: Herpes viridae

<400> SEQUENCE: 183

Gly Gly Asn Asn Ser Gln Tyr Pro Ser Ala Ser Gly Ser Ser Gly
1               5                   10                  15

<210> SEQ ID NO 184
<211> LENGTH: 15
<212> TYPE: PRT
<213> ORGANISM: Herpes viridae
```

<400> SEQUENCE: 184

Ser Gln Tyr Pro Ser Ala Ser Gly Ser Ser Gly Asn Thr Pro Thr
1               5                   10                  15

<210> SEQ ID NO 185
<211> LENGTH: 15
<212> TYPE: PRT
<213> ORGANISM: Herpes viridae

<400> SEQUENCE: 185

Ser Ala Ser Gly Ser Ser Gly Asn Thr Pro Thr Pro Pro Asn Asp
1               5                   10                  15

<210> SEQ ID NO 186
<211> LENGTH: 15
<212> TYPE: PRT
<213> ORGANISM: Herpes viridae

<400> SEQUENCE: 186

Ser Ser Gly Asn Thr Pro Thr Pro Pro Asn Asp Glu Glu Arg Glu
1               5                   10                  15

<210> SEQ ID NO 187
<211> LENGTH: 15
<212> TYPE: PRT
<213> ORGANISM: Herpes viridae

<400> SEQUENCE: 187

Thr Pro Thr Pro Pro Asn Asp Glu Glu Arg Glu Ser Asn Glu Glu
1               5                   10                  15

<210> SEQ ID NO 188
<211> LENGTH: 15
<212> TYPE: PRT
<213> ORGANISM: Herpes viridae

<400> SEQUENCE: 188

Pro Asn Asp Glu Glu Arg Glu Ser Asn Glu Glu Pro Pro Pro Pro
1               5                   10                  15

<210> SEQ ID NO 189
<211> LENGTH: 15
<212> TYPE: PRT
<213> ORGANISM: Herpes viridae

<400> SEQUENCE: 189

Glu Arg Glu Ser Asn Glu Glu Pro Pro Pro Pro Tyr Glu Asp Pro
1               5                   10                  15

<210> SEQ ID NO 190
<211> LENGTH: 15
<212> TYPE: PRT
<213> ORGANISM: Herpes viridae

<400> SEQUENCE: 190

Asn Glu Glu Pro Pro Pro Pro Tyr Glu Asp Pro Tyr Trp Gly Asn
1               5                   10                  15

<210> SEQ ID NO 191
<211> LENGTH: 15
<212> TYPE: PRT
<213> ORGANISM: Herpes viridae

```
<400> SEQUENCE: 191

Pro Pro Pro Tyr Glu Asp Pro Tyr Trp Gly Asn Gly Asp Arg His
1               5                   10                  15

<210> SEQ ID NO 192
<211> LENGTH: 15
<212> TYPE: PRT
<213> ORGANISM: Herpes viridae

<400> SEQUENCE: 192

Glu Asp Pro Tyr Trp Gly Asn Gly Asp Arg His Ser Asp Tyr Gln
1               5                   10                  15

<210> SEQ ID NO 193
<211> LENGTH: 15
<212> TYPE: PRT
<213> ORGANISM: Herpes viridae

<400> SEQUENCE: 193

Trp Gly Asn Gly Asp Arg His Ser Asp Tyr Gln Pro Leu Gly Thr
1               5                   10                  15

<210> SEQ ID NO 194
<211> LENGTH: 15
<212> TYPE: PRT
<213> ORGANISM: Herpes viridae

<400> SEQUENCE: 194

Asp Arg His Ser Asp Tyr Gln Pro Leu Gly Thr Gln Asp Gln Ser
1               5                   10                  15

<210> SEQ ID NO 195
<211> LENGTH: 15
<212> TYPE: PRT
<213> ORGANISM: Herpes viridae

<400> SEQUENCE: 195

Asp Tyr Gln Pro Leu Gly Thr Gln Asp Gln Ser Leu Tyr Leu Gly
1               5                   10                  15

<210> SEQ ID NO 196
<211> LENGTH: 15
<212> TYPE: PRT
<213> ORGANISM: Herpes viridae

<400> SEQUENCE: 196

Leu Gly Thr Gln Asp Gln Ser Leu Tyr Leu Gly Leu Gln His Asp
1               5                   10                  15

<210> SEQ ID NO 197
<211> LENGTH: 15
<212> TYPE: PRT
<213> ORGANISM: Herpes viridae

<400> SEQUENCE: 197

Asp Gln Ser Leu Tyr Leu Gly Leu Gln His Asp Gly Asn Asp Gly
1               5                   10                  15

<210> SEQ ID NO 198
<211> LENGTH: 15
<212> TYPE: PRT
<213> ORGANISM: Herpes viridae
```

```
<400> SEQUENCE: 198

Tyr Leu Gly Leu Gln His Asp Gly Asn Asp Gly Leu Pro Pro Pro
1               5                   10                  15

<210> SEQ ID NO 199
<211> LENGTH: 15
<212> TYPE: PRT
<213> ORGANISM: Herpes viridae

<400> SEQUENCE: 199

Gln His Asp Gly Asn Asp Gly Leu Pro Pro Pro Tyr Ser Pro
1               5                   10                  15

<210> SEQ ID NO 200
<211> LENGTH: 15
<212> TYPE: PRT
<213> ORGANISM: Herpes viridae

<400> SEQUENCE: 200

Asn Asp Gly Leu Pro Pro Pro Tyr Ser Pro Arg Asp Asp Ser
1               5                   10                  15

<210> SEQ ID NO 201
<211> LENGTH: 15
<212> TYPE: PRT
<213> ORGANISM: Herpes viridae

<400> SEQUENCE: 201

Pro Pro Pro Pro Tyr Ser Pro Arg Asp Asp Ser Ser Gln His Ile
1               5                   10                  15

<210> SEQ ID NO 202
<211> LENGTH: 15
<212> TYPE: PRT
<213> ORGANISM: Herpes viridae

<400> SEQUENCE: 202

Tyr Ser Pro Arg Asp Asp Ser Ser Gln His Ile Tyr Glu Glu Ala
1               5                   10                  15

<210> SEQ ID NO 203
<211> LENGTH: 15
<212> TYPE: PRT
<213> ORGANISM: Herpes viridae

<400> SEQUENCE: 203

Asp Asp Ser Ser Gln His Ile Tyr Glu Glu Ala Gly Arg Gly Ser
1               5                   10                  15

<210> SEQ ID NO 204
<211> LENGTH: 15
<212> TYPE: PRT
<213> ORGANISM: Herpes viridae

<400> SEQUENCE: 204

Gln His Ile Tyr Glu Glu Ala Gly Arg Gly Ser Met Asn Pro Val
1               5                   10                  15

<210> SEQ ID NO 205
<211> LENGTH: 15
<212> TYPE: PRT
<213> ORGANISM: Herpes viridae
```

```
<400> SEQUENCE: 205

Glu Glu Ala Gly Arg Gly Ser Met Asn Pro Val Cys Leu Pro Val
1               5                   10                  15

<210> SEQ ID NO 206
<211> LENGTH: 15
<212> TYPE: PRT
<213> ORGANISM: Herpes viridae

<400> SEQUENCE: 206

Arg Gly Ser Met Asn Pro Val Cys Leu Pro Val Ile Val Ala Pro
1               5                   10                  15

<210> SEQ ID NO 207
<211> LENGTH: 15
<212> TYPE: PRT
<213> ORGANISM: Herpes viridae

<400> SEQUENCE: 207

Asn Pro Val Cys Leu Pro Val Ile Val Ala Pro Tyr Leu Phe Trp
1               5                   10                  15

<210> SEQ ID NO 208
<211> LENGTH: 15
<212> TYPE: PRT
<213> ORGANISM: Herpes viridae

<400> SEQUENCE: 208

Leu Pro Val Ile Val Ala Pro Tyr Leu Phe Trp Leu Ala Ala Ile
1               5                   10                  15

<210> SEQ ID NO 209
<211> LENGTH: 15
<212> TYPE: PRT
<213> ORGANISM: Herpes viridae

<400> SEQUENCE: 209

Val Ala Pro Tyr Leu Phe Trp Leu Ala Ala Ile Ala Ala Ser Cys
1               5                   10                  15

<210> SEQ ID NO 210
<211> LENGTH: 15
<212> TYPE: PRT
<213> ORGANISM: Herpes viridae

<400> SEQUENCE: 210

Leu Phe Trp Leu Ala Ala Ile Ala Ala Ser Cys Phe Thr Ala Ser
1               5                   10                  15

<210> SEQ ID NO 211
<211> LENGTH: 15
<212> TYPE: PRT
<213> ORGANISM: Herpes viridae

<400> SEQUENCE: 211

Ala Ala Ile Ala Ala Ser Cys Phe Thr Ala Ser Val Ser Thr Val
1               5                   10                  15

<210> SEQ ID NO 212
<211> LENGTH: 15
<212> TYPE: PRT
<213> ORGANISM: Herpes viridae
```

```
<400> SEQUENCE: 212

Ala Ser Cys Phe Thr Ala Ser Val Ser Thr Val Val Thr Ala Thr
1               5                   10                  15

<210> SEQ ID NO 213
<211> LENGTH: 15
<212> TYPE: PRT
<213> ORGANISM: Herpes viridae

<400> SEQUENCE: 213

Thr Ala Ser Val Ser Thr Val Val Thr Ala Thr Gly Leu Ala Leu
1               5                   10                  15

<210> SEQ ID NO 214
<211> LENGTH: 15
<212> TYPE: PRT
<213> ORGANISM: Herpes viridae

<400> SEQUENCE: 214

Ser Thr Val Val Thr Ala Thr Gly Leu Ala Leu Ser Leu Leu Leu
1               5                   10                  15

<210> SEQ ID NO 215
<211> LENGTH: 15
<212> TYPE: PRT
<213> ORGANISM: Herpes viridae

<400> SEQUENCE: 215

Thr Ala Thr Gly Leu Ala Leu Ser Leu Leu Leu Leu Ala Ala Val
1               5                   10                  15

<210> SEQ ID NO 216
<211> LENGTH: 15
<212> TYPE: PRT
<213> ORGANISM: Herpes viridae

<400> SEQUENCE: 216

Leu Ala Leu Ser Leu Leu Leu Leu Ala Ala Val Ala Ser Ser Tyr
1               5                   10                  15

<210> SEQ ID NO 217
<211> LENGTH: 15
<212> TYPE: PRT
<213> ORGANISM: Herpes viridae

<400> SEQUENCE: 217

Leu Leu Leu Leu Ala Ala Val Ala Ser Ser Tyr Ala Ala Ala Gln
1               5                   10                  15

<210> SEQ ID NO 218
<211> LENGTH: 15
<212> TYPE: PRT
<213> ORGANISM: Herpes viridae

<400> SEQUENCE: 218

Ala Ala Val Ala Ser Ser Tyr Ala Ala Ala Gln Arg Lys Leu Leu
1               5                   10                  15

<210> SEQ ID NO 219
<211> LENGTH: 15
<212> TYPE: PRT
<213> ORGANISM: Herpes viridae
```

```
<400> SEQUENCE: 219

Ser Ser Tyr Ala Ala Gln Arg Lys Leu Leu Thr Pro Val Thr
1               5                   10                  15

<210> SEQ ID NO 220
<211> LENGTH: 15
<212> TYPE: PRT
<213> ORGANISM: Herpes viridae

<400> SEQUENCE: 220

Ala Ala Gln Arg Lys Leu Leu Thr Pro Val Thr Val Leu Thr Ala
1               5                   10                  15

<210> SEQ ID NO 221
<211> LENGTH: 15
<212> TYPE: PRT
<213> ORGANISM: Herpes viridae

<400> SEQUENCE: 221

Lys Leu Leu Thr Pro Val Thr Val Leu Thr Ala Val Val Thr Phe
1               5                   10                  15

<210> SEQ ID NO 222
<211> LENGTH: 15
<212> TYPE: PRT
<213> ORGANISM: Herpes viridae

<400> SEQUENCE: 222

Pro Val Thr Val Leu Thr Ala Val Val Thr Phe Phe Ala Ile Cys
1               5                   10                  15

<210> SEQ ID NO 223
<211> LENGTH: 15
<212> TYPE: PRT
<213> ORGANISM: Herpes viridae

<400> SEQUENCE: 223

Leu Thr Ala Val Val Thr Phe Phe Ala Ile Cys Leu Thr Trp Arg
1               5                   10                  15

<210> SEQ ID NO 224
<211> LENGTH: 15
<212> TYPE: PRT
<213> ORGANISM: Herpes viridae

<400> SEQUENCE: 224

Val Thr Phe Phe Ala Ile Cys Leu Thr Trp Arg Ile Glu Asp Pro
1               5                   10                  15

<210> SEQ ID NO 225
<211> LENGTH: 15
<212> TYPE: PRT
<213> ORGANISM: Herpes viridae

<400> SEQUENCE: 225

Ala Ile Cys Leu Thr Trp Arg Ile Glu Asp Pro Pro Phe Asn Ser
1               5                   10                  15

<210> SEQ ID NO 226
<211> LENGTH: 15
<212> TYPE: PRT
<213> ORGANISM: Herpes viridae
```

```
<400> SEQUENCE: 226

Thr Trp Arg Ile Glu Asp Pro Pro Phe Asn Ser Leu Leu Phe Ala
1               5                   10                  15

<210> SEQ ID NO 227
<211> LENGTH: 15
<212> TYPE: PRT
<213> ORGANISM: Herpes viridae

<400> SEQUENCE: 227

Glu Asp Pro Pro Phe Asn Ser Leu Leu Phe Ala Leu Leu Ala Ala
1               5                   10                  15

<210> SEQ ID NO 228
<211> LENGTH: 15
<212> TYPE: PRT
<213> ORGANISM: Herpes viridae

<400> SEQUENCE: 228

Phe Asn Ser Leu Leu Phe Ala Leu Leu Ala Ala Ala Gly Gly Leu
1               5                   10                  15

<210> SEQ ID NO 229
<211> LENGTH: 15
<212> TYPE: PRT
<213> ORGANISM: Herpes viridae

<400> SEQUENCE: 229

Leu Phe Ala Leu Leu Ala Ala Ala Gly Gly Leu Gln Gly Ile Tyr
1               5                   10                  15

<210> SEQ ID NO 230
<211> LENGTH: 15
<212> TYPE: PRT
<213> ORGANISM: Herpes viridae

<400> SEQUENCE: 230

Leu Ala Ala Ala Gly Gly Leu Gln Gly Ile Tyr Val Leu Val Met
1               5                   10                  15

<210> SEQ ID NO 231
<211> LENGTH: 15
<212> TYPE: PRT
<213> ORGANISM: Herpes viridae

<400> SEQUENCE: 231

Gly Gly Leu Gln Gly Ile Tyr Val Leu Val Met Leu Val Leu Leu
1               5                   10                  15

<210> SEQ ID NO 232
<211> LENGTH: 15
<212> TYPE: PRT
<213> ORGANISM: Herpes viridae

<400> SEQUENCE: 232

Gly Ile Tyr Val Leu Val Met Leu Val Leu Leu Ile Leu Ala Tyr
1               5                   10                  15

<210> SEQ ID NO 233
<211> LENGTH: 15
<212> TYPE: PRT
<213> ORGANISM: Herpes viridae
```

```
<400> SEQUENCE: 233

Leu Val Met Leu Val Leu Leu Ile Leu Ala Tyr Arg Arg Arg Trp
1               5                   10                  15

<210> SEQ ID NO 234
<211> LENGTH: 15
<212> TYPE: PRT
<213> ORGANISM: Herpes viridae

<400> SEQUENCE: 234

Val Leu Leu Ile Leu Ala Tyr Arg Arg Arg Trp Arg Arg Leu Thr
1               5                   10                  15

<210> SEQ ID NO 235
<211> LENGTH: 15
<212> TYPE: PRT
<213> ORGANISM: Herpes viridae

<400> SEQUENCE: 235

Leu Ala Tyr Arg Arg Arg Trp Arg Arg Leu Thr Val Cys Gly Gly
1               5                   10                  15

<210> SEQ ID NO 236
<211> LENGTH: 15
<212> TYPE: PRT
<213> ORGANISM: Herpes viridae

<400> SEQUENCE: 236

Arg Arg Trp Arg Arg Leu Thr Val Cys Gly Gly Ile Met Phe Leu
1               5                   10                  15

<210> SEQ ID NO 237
<211> LENGTH: 15
<212> TYPE: PRT
<213> ORGANISM: Herpes viridae

<400> SEQUENCE: 237

Arg Leu Thr Val Cys Gly Gly Ile Met Phe Leu Ala Cys Val Leu
1               5                   10                  15

<210> SEQ ID NO 238
<211> LENGTH: 15
<212> TYPE: PRT
<213> ORGANISM: Herpes viridae

<400> SEQUENCE: 238

Cys Gly Gly Ile Met Phe Leu Ala Cys Val Leu Val Leu Ile Val
1               5                   10                  15

<210> SEQ ID NO 239
<211> LENGTH: 15
<212> TYPE: PRT
<213> ORGANISM: Herpes viridae

<400> SEQUENCE: 239

Met Phe Leu Ala Cys Val Leu Val Leu Ile Val Asp Ala Val Leu
1               5                   10                  15

<210> SEQ ID NO 240
<211> LENGTH: 15
<212> TYPE: PRT
<213> ORGANISM: Herpes viridae
```

-continued

<400> SEQUENCE: 240

Cys Val Leu Val Leu Ile Val Asp Ala Val Leu Gln Leu Ser Pro
1               5                   10                  15

<210> SEQ ID NO 241
<211> LENGTH: 15
<212> TYPE: PRT
<213> ORGANISM: Herpes viridae

<400> SEQUENCE: 241

Leu Ile Val Asp Ala Val Leu Gln Leu Ser Pro Leu Leu Gly Ala
1               5                   10                  15

<210> SEQ ID NO 242
<211> LENGTH: 15
<212> TYPE: PRT
<213> ORGANISM: Herpes viridae

<400> SEQUENCE: 242

Ala Val Leu Gln Leu Ser Pro Leu Leu Gly Ala Val Thr Val Val
1               5                   10                  15

<210> SEQ ID NO 243
<211> LENGTH: 15
<212> TYPE: PRT
<213> ORGANISM: Herpes viridae

<400> SEQUENCE: 243

Leu Ser Pro Leu Leu Gly Ala Val Thr Val Val Ser Met Thr Leu
1               5                   10                  15

<210> SEQ ID NO 244
<211> LENGTH: 15
<212> TYPE: PRT
<213> ORGANISM: Herpes viridae

<400> SEQUENCE: 244

Leu Gly Ala Val Thr Val Val Ser Met Thr Leu Leu Leu Leu Ala
1               5                   10                  15

<210> SEQ ID NO 245
<211> LENGTH: 15
<212> TYPE: PRT
<213> ORGANISM: Herpes viridae

<400> SEQUENCE: 245

Thr Val Val Ser Met Thr Leu Leu Leu Leu Ala Phe Val Leu Trp
1               5                   10                  15

<210> SEQ ID NO 246
<211> LENGTH: 15
<212> TYPE: PRT
<213> ORGANISM: Herpes viridae

<400> SEQUENCE: 246

Met Thr Leu Leu Leu Leu Ala Phe Val Leu Trp Leu Ser Ser Pro
1               5                   10                  15

<210> SEQ ID NO 247
<211> LENGTH: 15
<212> TYPE: PRT
<213> ORGANISM: Herpes viridae

```
<400> SEQUENCE: 247

Leu Leu Ala Phe Val Leu Trp Leu Ser Ser Pro Gly Gly Leu Gly
1               5                   10                  15

<210> SEQ ID NO 248
<211> LENGTH: 15
<212> TYPE: PRT
<213> ORGANISM: Herpes viridae

<400> SEQUENCE: 248

Val Leu Trp Leu Ser Ser Pro Gly Gly Leu Gly Thr Leu Gly Ala
1               5                   10                  15

<210> SEQ ID NO 249
<211> LENGTH: 15
<212> TYPE: PRT
<213> ORGANISM: Herpes viridae

<400> SEQUENCE: 249

Ser Ser Pro Gly Gly Leu Gly Thr Leu Gly Ala Ala Leu Leu Thr
1               5                   10                  15

<210> SEQ ID NO 250
<211> LENGTH: 15
<212> TYPE: PRT
<213> ORGANISM: Herpes viridae

<400> SEQUENCE: 250

Gly Leu Gly Thr Leu Gly Ala Ala Leu Leu Thr Leu Ala Ala Ala
1               5                   10                  15

<210> SEQ ID NO 251
<211> LENGTH: 15
<212> TYPE: PRT
<213> ORGANISM: Herpes viridae

<400> SEQUENCE: 251

Leu Gly Ala Ala Leu Leu Thr Leu Ala Ala Ala Leu Ala Leu Leu
1               5                   10                  15

<210> SEQ ID NO 252
<211> LENGTH: 15
<212> TYPE: PRT
<213> ORGANISM: Herpes viridae

<400> SEQUENCE: 252

Leu Leu Thr Leu Ala Ala Ala Leu Ala Leu Leu Ala Ser Leu Ile
1               5                   10                  15

<210> SEQ ID NO 253
<211> LENGTH: 15
<212> TYPE: PRT
<213> ORGANISM: Herpes viridae

<400> SEQUENCE: 253

Ala Ala Ala Leu Ala Leu Leu Ala Ser Leu Ile Leu Gly Thr Leu
1               5                   10                  15

<210> SEQ ID NO 254
<211> LENGTH: 15
<212> TYPE: PRT
<213> ORGANISM: Herpes viridae
```

-continued

<400> SEQUENCE: 254

Ala Leu Leu Ala Ser Leu Ile Leu Gly Thr Leu Asn Leu Thr Thr
1               5                   10                  15

<210> SEQ ID NO 255
<211> LENGTH: 15
<212> TYPE: PRT
<213> ORGANISM: Herpes viridae

<400> SEQUENCE: 255

Ser Leu Ile Leu Gly Thr Leu Asn Leu Thr Thr Met Phe Leu Leu
1               5                   10                  15

<210> SEQ ID NO 256
<211> LENGTH: 15
<212> TYPE: PRT
<213> ORGANISM: Herpes viridae

<400> SEQUENCE: 256

Gly Thr Leu Asn Leu Thr Thr Met Phe Leu Leu Met Leu Leu Trp
1               5                   10                  15

<210> SEQ ID NO 257
<211> LENGTH: 15
<212> TYPE: PRT
<213> ORGANISM: Herpes viridae

<400> SEQUENCE: 257

Leu Thr Thr Met Phe Leu Leu Met Leu Leu Trp Thr Leu Val Val
1               5                   10                  15

<210> SEQ ID NO 258
<211> LENGTH: 15
<212> TYPE: PRT
<213> ORGANISM: Herpes viridae

<400> SEQUENCE: 258

Phe Leu Leu Met Leu Leu Trp Thr Leu Val Val Leu Leu Ile Cys
1               5                   10                  15

<210> SEQ ID NO 259
<211> LENGTH: 15
<212> TYPE: PRT
<213> ORGANISM: Herpes viridae

<400> SEQUENCE: 259

Leu Leu Trp Thr Leu Val Val Leu Leu Ile Cys Ser Ser Cys Ser
1               5                   10                  15

<210> SEQ ID NO 260
<211> LENGTH: 15
<212> TYPE: PRT
<213> ORGANISM: Herpes viridae

<400> SEQUENCE: 260

Leu Val Val Leu Leu Ile Cys Ser Ser Cys Ser Ser Cys Pro Leu
1               5                   10                  15

<210> SEQ ID NO 261
<211> LENGTH: 15
<212> TYPE: PRT
<213> ORGANISM: Herpes viridae

```
<400> SEQUENCE: 261

Leu Ile Cys Ser Ser Cys Ser Ser Cys Pro Leu Ser Lys Ile Leu
1               5                   10                  15

<210> SEQ ID NO 262
<211> LENGTH: 15
<212> TYPE: PRT
<213> ORGANISM: Herpes viridae

<400> SEQUENCE: 262

Ser Cys Ser Ser Cys Pro Leu Ser Lys Ile Leu Leu Ala Arg Leu
1               5                   10                  15

<210> SEQ ID NO 263
<211> LENGTH: 15
<212> TYPE: PRT
<213> ORGANISM: Herpes viridae

<400> SEQUENCE: 263

Cys Pro Leu Ser Lys Ile Leu Leu Ala Arg Leu Phe Leu Tyr Ala
1               5                   10                  15

<210> SEQ ID NO 264
<211> LENGTH: 15
<212> TYPE: PRT
<213> ORGANISM: Herpes viridae

<400> SEQUENCE: 264

Lys Ile Leu Leu Ala Arg Leu Phe Leu Tyr Ala Leu Ala Leu Leu
1               5                   10                  15

<210> SEQ ID NO 265
<211> LENGTH: 15
<212> TYPE: PRT
<213> ORGANISM: Herpes viridae

<400> SEQUENCE: 265

Ala Arg Leu Phe Leu Tyr Ala Leu Ala Leu Leu Leu Leu Ala Ser
1               5                   10                  15

<210> SEQ ID NO 266
<211> LENGTH: 15
<212> TYPE: PRT
<213> ORGANISM: Herpes viridae

<400> SEQUENCE: 266

Leu Tyr Ala Leu Ala Leu Leu Leu Leu Ala Ser Ala Leu Ile Ala
1               5                   10                  15

<210> SEQ ID NO 267
<211> LENGTH: 15
<212> TYPE: PRT
<213> ORGANISM: Herpes viridae

<400> SEQUENCE: 267

Ala Leu Leu Leu Leu Ala Ser Ala Leu Ile Ala Gly Gly Ser Ile
1               5                   10                  15

<210> SEQ ID NO 268
<211> LENGTH: 15
<212> TYPE: PRT
<213> ORGANISM: Herpes viridae
```

```
<400> SEQUENCE: 268

Leu Ala Ser Ala Leu Ile Ala Gly Gly Ser Ile Leu Gln Thr Asn
1               5                   10                  15

<210> SEQ ID NO 269
<211> LENGTH: 15
<212> TYPE: PRT
<213> ORGANISM: Herpes viridae

<400> SEQUENCE: 269

Leu Ile Ala Gly Gly Ser Ile Leu Gln Thr Asn Phe Lys Ser Leu
1               5                   10                  15

<210> SEQ ID NO 270
<211> LENGTH: 15
<212> TYPE: PRT
<213> ORGANISM: Herpes viridae

<400> SEQUENCE: 270

Gly Ser Ile Leu Gln Thr Asn Phe Lys Ser Leu Ser Ser Thr Glu
1               5                   10                  15

<210> SEQ ID NO 271
<211> LENGTH: 15
<212> TYPE: PRT
<213> ORGANISM: Herpes viridae

<400> SEQUENCE: 271

Gln Thr Asn Phe Lys Ser Leu Ser Ser Thr Glu Phe Ile Pro Asn
1               5                   10                  15

<210> SEQ ID NO 272
<211> LENGTH: 15
<212> TYPE: PRT
<213> ORGANISM: Herpes viridae

<400> SEQUENCE: 272

Lys Ser Leu Ser Ser Thr Glu Phe Ile Pro Asn Leu Phe Cys Met
1               5                   10                  15

<210> SEQ ID NO 273
<211> LENGTH: 15
<212> TYPE: PRT
<213> ORGANISM: Herpes viridae

<400> SEQUENCE: 273

Ser Thr Glu Phe Ile Pro Asn Leu Phe Cys Met Leu Leu Leu Ile
1               5                   10                  15

<210> SEQ ID NO 274
<211> LENGTH: 15
<212> TYPE: PRT
<213> ORGANISM: Herpes viridae

<400> SEQUENCE: 274

Ile Pro Asn Leu Phe Cys Met Leu Leu Leu Ile Val Ala Gly Ile
1               5                   10                  15

<210> SEQ ID NO 275
<211> LENGTH: 15
<212> TYPE: PRT
<213> ORGANISM: Herpes viridae
```

```
<400> SEQUENCE: 275

Phe Cys Met Leu Leu Ile Val Ala Gly Ile Leu Phe Ile Leu
1               5                   10                  15

<210> SEQ ID NO 276
<211> LENGTH: 15
<212> TYPE: PRT
<213> ORGANISM: Herpes viridae

<400> SEQUENCE: 276

Leu Leu Ile Val Ala Gly Ile Leu Phe Ile Leu Ala Ile Leu Thr
1               5                   10                  15

<210> SEQ ID NO 277
<211> LENGTH: 15
<212> TYPE: PRT
<213> ORGANISM: Herpes viridae

<400> SEQUENCE: 277

Ala Gly Ile Leu Phe Ile Leu Ala Ile Leu Thr Glu Trp Gly Ser
1               5                   10                  15

<210> SEQ ID NO 278
<211> LENGTH: 15
<212> TYPE: PRT
<213> ORGANISM: Herpes viridae

<400> SEQUENCE: 278

Phe Ile Leu Ala Ile Leu Thr Glu Trp Gly Ser Gly Asn Arg Thr
1               5                   10                  15

<210> SEQ ID NO 279
<211> LENGTH: 15
<212> TYPE: PRT
<213> ORGANISM: Herpes viridae

<400> SEQUENCE: 279

Ile Leu Thr Glu Trp Gly Ser Gly Asn Arg Thr Tyr Gly Pro Val
1               5                   10                  15

<210> SEQ ID NO 280
<211> LENGTH: 15
<212> TYPE: PRT
<213> ORGANISM: Herpes viridae

<400> SEQUENCE: 280

Trp Gly Ser Gly Asn Arg Thr Tyr Gly Pro Val Phe Met Cys Leu
1               5                   10                  15

<210> SEQ ID NO 281
<211> LENGTH: 15
<212> TYPE: PRT
<213> ORGANISM: Herpes viridae

<400> SEQUENCE: 281

Asn Arg Thr Tyr Gly Pro Val Phe Met Cys Leu Gly Gly Leu Leu
1               5                   10                  15

<210> SEQ ID NO 282
<211> LENGTH: 15
<212> TYPE: PRT
<213> ORGANISM: Herpes viridae
```

```
<400> SEQUENCE: 282

Gly Pro Val Phe Met Cys Leu Gly Gly Leu Leu Thr Met Val Ala
1               5                   10                  15

<210> SEQ ID NO 283
<211> LENGTH: 15
<212> TYPE: PRT
<213> ORGANISM: Herpes viridae

<400> SEQUENCE: 283

Met Cys Leu Gly Gly Leu Leu Thr Met Val Ala Gly Ala Val Trp
1               5                   10                  15

<210> SEQ ID NO 284
<211> LENGTH: 15
<212> TYPE: PRT
<213> ORGANISM: Herpes viridae

<400> SEQUENCE: 284

Gly Leu Leu Thr Met Val Ala Gly Ala Val Trp Leu Thr Val Met
1               5                   10                  15

<210> SEQ ID NO 285
<211> LENGTH: 15
<212> TYPE: PRT
<213> ORGANISM: Herpes viridae

<400> SEQUENCE: 285

Met Val Ala Gly Ala Val Trp Leu Thr Val Met Ser Asn Thr Leu
1               5                   10                  15

<210> SEQ ID NO 286
<211> LENGTH: 15
<212> TYPE: PRT
<213> ORGANISM: Herpes viridae

<400> SEQUENCE: 286

Ala Val Trp Leu Thr Val Met Ser Asn Thr Leu Leu Ser Ala Trp
1               5                   10                  15

<210> SEQ ID NO 287
<211> LENGTH: 15
<212> TYPE: PRT
<213> ORGANISM: Herpes viridae

<400> SEQUENCE: 287

Thr Val Met Ser Asn Thr Leu Leu Ser Ala Trp Ile Leu Thr Ala
1               5                   10                  15

<210> SEQ ID NO 288
<211> LENGTH: 15
<212> TYPE: PRT
<213> ORGANISM: Herpes viridae

<400> SEQUENCE: 288

Asn Thr Leu Leu Ser Ala Trp Ile Leu Thr Ala Gly Phe Leu Ile
1               5                   10                  15

<210> SEQ ID NO 289
<211> LENGTH: 15
<212> TYPE: PRT
<213> ORGANISM: Herpes viridae
```

<400> SEQUENCE: 289

Ser Ala Trp Ile Leu Thr Ala Gly Phe Leu Ile Phe Leu Ile Gly
1               5                   10                  15

<210> SEQ ID NO 290
<211> LENGTH: 15
<212> TYPE: PRT
<213> ORGANISM: Herpes viridae

<400> SEQUENCE: 290

Leu Thr Ala Gly Phe Leu Ile Phe Leu Ile Gly Phe Ala Leu Phe
1               5                   10                  15

<210> SEQ ID NO 291
<211> LENGTH: 15
<212> TYPE: PRT
<213> ORGANISM: Herpes viridae

<400> SEQUENCE: 291

Phe Leu Ile Phe Leu Ile Gly Phe Ala Leu Phe Gly Val Ile Arg
1               5                   10                  15

<210> SEQ ID NO 292
<211> LENGTH: 15
<212> TYPE: PRT
<213> ORGANISM: Herpes viridae

<400> SEQUENCE: 292

Leu Ile Gly Phe Ala Leu Phe Gly Val Ile Arg Cys Cys Arg Tyr
1               5                   10                  15

<210> SEQ ID NO 293
<211> LENGTH: 15
<212> TYPE: PRT
<213> ORGANISM: Herpes viridae

<400> SEQUENCE: 293

Ala Leu Phe Gly Val Ile Arg Cys Cys Arg Tyr Cys Cys Tyr Tyr
1               5                   10                  15

<210> SEQ ID NO 294
<211> LENGTH: 15
<212> TYPE: PRT
<213> ORGANISM: Herpes viridae

<400> SEQUENCE: 294

Val Ile Arg Cys Cys Arg Tyr Cys Cys Tyr Tyr Cys Leu Thr Leu
1               5                   10                  15

<210> SEQ ID NO 295
<211> LENGTH: 15
<212> TYPE: PRT
<213> ORGANISM: Herpes viridae

<400> SEQUENCE: 295

Cys Arg Tyr Cys Cys Tyr Tyr Cys Leu Thr Leu Glu Ser Glu Glu
1               5                   10                  15

<210> SEQ ID NO 296
<211> LENGTH: 15
<212> TYPE: PRT
<213> ORGANISM: Herpes viridae

```
<400> SEQUENCE: 296

Cys Tyr Tyr Cys Leu Thr Leu Glu Ser Glu Glu Arg Pro Pro Thr
1               5                   10                  15

<210> SEQ ID NO 297
<211> LENGTH: 15
<212> TYPE: PRT
<213> ORGANISM: Herpes viridae

<400> SEQUENCE: 297

Leu Thr Leu Glu Ser Glu Glu Arg Pro Pro Thr Pro Tyr Arg Asn
1               5                   10                  15

<210> SEQ ID NO 298
<211> LENGTH: 13
<212> TYPE: PRT
<213> ORGANISM: Herpes viridae

<400> SEQUENCE: 298

Ser Glu Glu Arg Pro Pro Thr Pro Tyr Arg Asn Thr Val
1               5                   10

<210> SEQ ID NO 299
<211> LENGTH: 15
<212> TYPE: PRT
<213> ORGANISM: Herpes viridae

<400> SEQUENCE: 299

Met Ala Arg Phe Ile Ala Gln Leu Leu Leu Ala Ser Cys Val
1               5                   10                  15

<210> SEQ ID NO 300
<211> LENGTH: 15
<212> TYPE: PRT
<213> ORGANISM: Herpes viridae

<400> SEQUENCE: 300

Ala Gln Leu Leu Leu Ala Ser Cys Val Ala Ala Gly Gln Ala
1               5                   10                  15

<210> SEQ ID NO 301
<211> LENGTH: 15
<212> TYPE: PRT
<213> ORGANISM: Herpes viridae

<400> SEQUENCE: 301

Leu Ala Ser Cys Val Ala Ala Gly Gln Ala Val Thr Ala Phe Leu
1               5                   10                  15

<210> SEQ ID NO 302
<211> LENGTH: 15
<212> TYPE: PRT
<213> ORGANISM: Herpes viridae

<400> SEQUENCE: 302

Ala Ala Gly Gln Ala Val Thr Ala Phe Leu Gly Glu Arg Val Thr
1               5                   10                  15

<210> SEQ ID NO 303
<211> LENGTH: 15
<212> TYPE: PRT
```

```
<400> SEQUENCE: 303

Val Thr Ala Phe Leu Gly Glu Arg Val Thr Leu Thr Ser Tyr Trp
1               5                   10                  15

<210> SEQ ID NO 304
<211> LENGTH: 15
<212> TYPE: PRT
<213> ORGANISM: Herpes viridae

<400> SEQUENCE: 304

Gly Glu Arg Val Thr Leu Thr Ser Tyr Trp Arg Arg Val Ser Leu
1               5                   10                  15

<210> SEQ ID NO 305
<211> LENGTH: 15
<212> TYPE: PRT
<213> ORGANISM: Herpes viridae

<400> SEQUENCE: 305

Leu Thr Ser Tyr Trp Arg Arg Val Ser Leu Gly Pro Glu Ile Glu
1               5                   10                  15

<210> SEQ ID NO 306
<211> LENGTH: 15
<212> TYPE: PRT
<213> ORGANISM: Herpes viridae

<400> SEQUENCE: 306

Arg Arg Val Ser Leu Gly Pro Glu Ile Glu Val Ser Trp Phe Lys
1               5                   10                  15

<210> SEQ ID NO 307
<211> LENGTH: 15
<212> TYPE: PRT
<213> ORGANISM: Herpes viridae

<400> SEQUENCE: 307

Gly Pro Glu Ile Glu Val Ser Trp Phe Lys Leu Gly Pro Gly Glu
1               5                   10                  15

<210> SEQ ID NO 308
<211> LENGTH: 15
<212> TYPE: PRT
<213> ORGANISM: Herpes viridae

<400> SEQUENCE: 308

Val Ser Trp Phe Lys Leu Gly Pro Gly Glu Glu Gln Val Leu Ile
1               5                   10                  15

<210> SEQ ID NO 309
<211> LENGTH: 15
<212> TYPE: PRT
<213> ORGANISM: Herpes viridae

<400> SEQUENCE: 309

Leu Gly Pro Gly Glu Glu Gln Val Leu Ile Gly Arg Met His His
1               5                   10                  15

<210> SEQ ID NO 310
<211> LENGTH: 15
<212> TYPE: PRT
<213> ORGANISM: Herpes viridae
```

```
<400> SEQUENCE: 310

Glu Gln Val Leu Ile Gly Arg Met His His Asp Val Ile Phe Ile
1               5                   10                  15

<210> SEQ ID NO 311
<211> LENGTH: 15
<212> TYPE: PRT
<213> ORGANISM: Herpes viridae

<400> SEQUENCE: 311

Gly Arg Met His His Asp Val Ile Phe Ile Glu Trp Pro Phe Arg
1               5                   10                  15

<210> SEQ ID NO 312
<211> LENGTH: 15
<212> TYPE: PRT
<213> ORGANISM: Herpes viridae

<400> SEQUENCE: 312

Asp Val Ile Phe Ile Glu Trp Pro Phe Arg Gly Phe Phe Asp Ile
1               5                   10                  15

<210> SEQ ID NO 313
<211> LENGTH: 15
<212> TYPE: PRT
<213> ORGANISM: Herpes viridae

<400> SEQUENCE: 313

Glu Trp Pro Phe Arg Gly Phe Phe Asp Ile His Arg Ser Ala Asn
1               5                   10                  15

<210> SEQ ID NO 314
<211> LENGTH: 15
<212> TYPE: PRT
<213> ORGANISM: Herpes viridae

<400> SEQUENCE: 314

Gly Phe Phe Asp Ile His Arg Ser Ala Asn Thr Phe Phe Leu Val
1               5                   10                  15

<210> SEQ ID NO 315
<211> LENGTH: 15
<212> TYPE: PRT
<213> ORGANISM: Herpes viridae

<400> SEQUENCE: 315

His Arg Ser Ala Asn Thr Phe Phe Leu Val Val Thr Ala Ala Asn
1               5                   10                  15

<210> SEQ ID NO 316
<211> LENGTH: 15
<212> TYPE: PRT
<213> ORGANISM: Herpes viridae

<400> SEQUENCE: 316

Thr Phe Phe Leu Val Val Thr Ala Ala Asn Ile Ser His Asp Gly
1               5                   10                  15

<210> SEQ ID NO 317
<211> LENGTH: 15
<212> TYPE: PRT
<213> ORGANISM: Herpes viridae
```

```
<400> SEQUENCE: 317

Val Thr Ala Ala Asn Ile Ser His Asp Gly Asn Tyr Leu Cys Arg
1               5                   10                  15

<210> SEQ ID NO 318
<211> LENGTH: 15
<212> TYPE: PRT
<213> ORGANISM: Herpes viridae

<400> SEQUENCE: 318

Ile Ser His Asp Gly Asn Tyr Leu Cys Arg Met Lys Leu Gly Glu
1               5                   10                  15

<210> SEQ ID NO 319
<211> LENGTH: 15
<212> TYPE: PRT
<213> ORGANISM: Herpes viridae

<400> SEQUENCE: 319

Asn Tyr Leu Cys Arg Met Lys Leu Gly Glu Thr Glu Val Thr Lys
1               5                   10                  15

<210> SEQ ID NO 320
<211> LENGTH: 15
<212> TYPE: PRT
<213> ORGANISM: Herpes viridae

<400> SEQUENCE: 320

Met Lys Leu Gly Glu Thr Glu Val Thr Lys Gln Glu His Leu Ser
1               5                   10                  15

<210> SEQ ID NO 321
<211> LENGTH: 15
<212> TYPE: PRT
<213> ORGANISM: Herpes viridae

<400> SEQUENCE: 321

Thr Glu Val Thr Lys Gln Glu His Leu Ser Val Val Lys Pro Leu
1               5                   10                  15

<210> SEQ ID NO 322
<211> LENGTH: 15
<212> TYPE: PRT
<213> ORGANISM: Herpes viridae

<400> SEQUENCE: 322

Gln Glu His Leu Ser Val Val Lys Pro Leu Thr Leu Ser Val His
1               5                   10                  15

<210> SEQ ID NO 323
<211> LENGTH: 15
<212> TYPE: PRT
<213> ORGANISM: Herpes viridae

<400> SEQUENCE: 323

Val Val Lys Pro Leu Thr Leu Ser Val His Ser Glu Arg Ser Gln
1               5                   10                  15

<210> SEQ ID NO 324
<211> LENGTH: 15
<212> TYPE: PRT
<213> ORGANISM: Herpes viridae
```

-continued

<400> SEQUENCE: 324

Thr Leu Ser Val His Ser Glu Arg Ser Gln Phe Pro Asp Phe Ser
1               5                   10                  15

<210> SEQ ID NO 325
<211> LENGTH: 15
<212> TYPE: PRT
<213> ORGANISM: Herpes viridae

<400> SEQUENCE: 325

Ser Glu Arg Ser Gln Phe Pro Asp Phe Ser Val Leu Thr Val Thr
1               5                   10                  15

<210> SEQ ID NO 326
<211> LENGTH: 15
<212> TYPE: PRT
<213> ORGANISM: Herpes viridae

<400> SEQUENCE: 326

Phe Pro Asp Phe Ser Val Leu Thr Val Thr Cys Thr Val Asn Ala
1               5                   10                  15

<210> SEQ ID NO 327
<211> LENGTH: 15
<212> TYPE: PRT
<213> ORGANISM: Herpes viridae

<400> SEQUENCE: 327

Val Leu Thr Val Thr Cys Thr Val Asn Ala Phe Pro His Pro His
1               5                   10                  15

<210> SEQ ID NO 328
<211> LENGTH: 15
<212> TYPE: PRT
<213> ORGANISM: Herpes viridae

<400> SEQUENCE: 328

Cys Thr Val Asn Ala Phe Pro His Pro His Val Gln Trp Leu Met
1               5                   10                  15

<210> SEQ ID NO 329
<211> LENGTH: 15
<212> TYPE: PRT
<213> ORGANISM: Herpes viridae

<400> SEQUENCE: 329

Phe Pro His Pro His Val Gln Trp Leu Met Pro Glu Gly Val Glu
1               5                   10                  15

<210> SEQ ID NO 330
<211> LENGTH: 15
<212> TYPE: PRT
<213> ORGANISM: Herpes viridae

<400> SEQUENCE: 330

Val Gln Trp Leu Met Pro Glu Gly Val Glu Pro Ala Pro Thr Ala
1               5                   10                  15

<210> SEQ ID NO 331
<211> LENGTH: 15
<212> TYPE: PRT
<213> ORGANISM: Herpes viridae

```
<400> SEQUENCE: 331

Pro Glu Gly Val Glu Pro Ala Pro Thr Ala Ala Asn Gly Gly Val
1               5                   10                  15

<210> SEQ ID NO 332
<211> LENGTH: 15
<212> TYPE: PRT
<213> ORGANISM: Herpes viridae

<400> SEQUENCE: 332

Pro Ala Pro Thr Ala Ala Asn Gly Gly Val Gly Ser Leu Ser Val
1               5                   10                  15

<210> SEQ ID NO 333
<211> LENGTH: 15
<212> TYPE: PRT
<213> ORGANISM: Herpes viridae

<400> SEQUENCE: 333

Ala Asn Gly Gly Val Gly Ser Leu Ser Val Ala Val Asp Leu Ser
1               5                   10                  15

<210> SEQ ID NO 334
<211> LENGTH: 15
<212> TYPE: PRT
<213> ORGANISM: Herpes viridae

<400> SEQUENCE: 334

Gly Ser Leu Ser Val Ala Val Asp Leu Ser Leu Pro Lys Pro Trp
1               5                   10                  15

<210> SEQ ID NO 335
<211> LENGTH: 15
<212> TYPE: PRT
<213> ORGANISM: Herpes viridae

<400> SEQUENCE: 335

Ala Val Asp Leu Ser Leu Pro Lys Pro Trp His Leu Pro Val Thr
1               5                   10                  15

<210> SEQ ID NO 336
<211> LENGTH: 15
<212> TYPE: PRT
<213> ORGANISM: Herpes viridae

<400> SEQUENCE: 336

Leu Pro Lys Pro Trp His Leu Pro Val Thr Cys Val Gly Lys Asn
1               5                   10                  15

<210> SEQ ID NO 337
<211> LENGTH: 15
<212> TYPE: PRT
<213> ORGANISM: Herpes viridae

<400> SEQUENCE: 337

His Leu Pro Val Thr Cys Val Gly Lys Asn Asp Lys Glu Glu Ala
1               5                   10                  15

<210> SEQ ID NO 338
<211> LENGTH: 15
<212> TYPE: PRT
<213> ORGANISM: Herpes viridae
```

```
<400> SEQUENCE: 338

Cys Val Gly Lys Asn Asp Lys Glu Glu Ala His Gly Val Tyr Val
1               5                   10                  15

<210> SEQ ID NO 339
<211> LENGTH: 15
<212> TYPE: PRT
<213> ORGANISM: Herpes viridae

<400> SEQUENCE: 339

Asp Lys Glu Glu Ala His Gly Val Tyr Val Ser Gly Tyr Leu Ser
1               5                   10                  15

<210> SEQ ID NO 340
<211> LENGTH: 220
<212> TYPE: PRT
<213> ORGANISM: Herpes viridae

<400> SEQUENCE: 340

Met Ala Arg Phe Ile Ala Gln Leu Leu Leu Ala Ser Cys Val Ala
1               5                   10                  15

Ala Gly Gln Ala Val Thr Ala Phe Leu Gly Glu Arg Val Thr Leu Thr
                20                  25                  30

Ser Tyr Trp Arg Arg Val Ser Leu Gly Pro Glu Ile Glu Val Ser Trp
            35                  40                  45

Phe Lys Leu Gly Pro Gly Glu Glu Gln Val Leu Ile Gly Arg Met His
    50                  55                  60

His Asp Val Ile Phe Ile Glu Trp Pro Phe Arg Gly Phe Phe Asp Ile
65                  70                  75                  80

His Arg Ser Ala Asn Thr Phe Phe Leu Val Val Thr Ala Ala Asn Ile
                85                  90                  95

Ser His Asp Gly Asn Tyr Leu Cys Arg Met Lys Leu Gly Glu Thr Glu
            100                 105                 110

Val Thr Lys Gln Glu His Leu Ser Val Val Lys Pro Leu Thr Leu Ser
            115                 120                 125

Val His Ser Glu Arg Ser Gln Phe Pro Asp Phe Ser Val Leu Thr Val
            130                 135                 140

Thr Cys Thr Val Asn Ala Phe Pro His Pro His Val Gln Trp Leu Met
145                 150                 155                 160

Pro Glu Gly Val Glu Pro Ala Pro Thr Ala Ala Asn Gly Gly Val Met
                165                 170                 175

Lys Glu Lys Asp Gly Ser Leu Ser Val Ala Val Asp Leu Ser Leu Pro
            180                 185                 190

Lys Pro Trp His Leu Pro Val Thr Cys Val Gly Lys Asn Asp Lys Glu
            195                 200                 205

Glu Ala His Gly Val Tyr Val Ser Gly Tyr Leu Ser
            210                 215                 220
```

PROCESS OF EXPANDING T CELLS

CROSS REFERENCE TO RELATED APPLICATIONS

This application is a continuation of U.S. patent application Ser. No. 14/364,592, filed on Sep. 24, 2014, now issued as U.S. patent Ser. No. 10/351,824 on Jul. 16, 2019, which is a national phase application under 35 U.S.C. § 371 that claims priority to International Application No. PCT/GB2012/050896, filed Apr. 23, 2012, which claims priority to U.S. Provisional Patent Application Ser. No. 61/569,577, filed Dec. 12, 2011. The entire contents of these applications are incorporated by reference herein in their entirety.

INCORPORATED BY REFERENCE

This application incorporates by reference the contents of an 68.9 kb text file created on May 6, 2019 and named "0043CON_REPLACEMENT_SequenceListing2.txt," which is the sequence listing for this application.

TECHNICAL FIELD

The present invention relates to a novel process for expanding T cells, such as autologous T cells, cell populations therefrom, pharmaceutical compositions comprising the said cell populations and use of the cells and compositions for treatment, particular the treatment or prophylaxis of virus infection and/or cancer, for example in immune compromised or immune competent human patients.

BACKGROUND

While viruses are widely recognized as a cause of infectious disease, certain viruses are also associated with human cancer. The human immune system is central to the control of viral infections and also malignancies shown to be related to oncogenic viruses. Within the complex array of cells, antibodies and immunomodulatory molecules which constitute the human immune system, lymphocytes of thymic origin (T cells) operate in a central role to control viral infections and cancer. Hence, one approach to prevent or treat virus infections and cancer has been to take T-cells from these patients and stimulate and/or expand them in vitro before transfusing them back into the patient.

In vivo T cell activation and antigen-specific expansion is generally considered to result from a two signal process wherein the first signal is initiated by the ligation of the T cell receptor/CD3 complex with a major histocompatibility complex class I or class II molecule (MHC Class I or MHC Class II) presenting a peptide antigen. The MHC Class I or MHC Class II and peptide complex is expressed on the surface of a cell (the antigen presenting cell or APC). The peptide antigen originates from a molecule within the cell which undergoes endogenous processing and may be, inter olio, (1) a "self" antigen naturally occurring in the body; (2) a tumour antigen which results from a mutation related to cancer or (3) a viral antigen associated with infection or cancer. The recognition of the antigen by the T cell receptor is considered the first signal and the second signal arises from co-stimulation which results from the ligation of additional surface molecules on the T cell with additional molecules on the APC. The up-regulation and ligation of these co-stimulatory molecules between the T cell and APC may be necessary to effect or enhance T cell activation since the first signal may not be sufficient alone to achieve this.

The two signal activation may lead to the expansion of the T cell so that greater numbers of the antigen-specific T cells will be available to control the pathogen or cancer giving rise to the immune response. The canonical understanding of this two signal activation is based on the same APC providing both the first signal and the second signal to the responding T cell such that the co-stimulation is directly associated with antigen recognition. The in vitro activation and expansion of T cells has traditionally been a long, complex and resource intensive process. A typical process may, for example take 8-12 weeks and often employs live "target" virus and/or viral vectors to achieve antigen presentation by antigen presenting cells (APC). Generally T cell activation/expansion requires static conditions rather than stirred or physically agitated culture systems.

One prior art method of culturing antigen specific T cells which recognize the LMP1 and LMP2 antigens of Epstein Barr Virus (EBV) may be summarized as follows:

Preparatory Steps

In order to achieve the two signal T cell activation and expansion process in a controlled manner, it is useful to create an antigen-presenting cell through transfection of B cells taken from the patient. This is referred to as establishing an autologous lymphoblastoid cell line and is undertaken through infection of the cell with EBV (EBV-LCL). It takes about 6-8 weeks to develop this cell line and thus it is one of the first stages that must be started as part of a culture process which relies upon the EBV-LCL for antigen presentation. It is prepared by culturing B cells from the patient with EBV virus in the presence of cyclosporine A to inhibit EBV-specific T cell outgrowth and elimination of the LCL.

Prior to the expansion step with the EBV-LCLs, the culture system involves the initial activation and expansion of the LMP-1 and LMP-2 specific T cells with autologous dendritic cells which been transduced with a viral vector Ad5f35-LMP1-LMP2 (encoding the EBV proteins LMP1 and LMP2) (days 0 to 8).

day 9 to 12 the cytolytic T lymphocytes (CTLs) are harvested and re-suspended in fresh medium and re-stimulated with EBV-LCLs transduced with Ad5f35-LMP1-LMP2.

day 13 to 16 cytolytic T lymphocytes are fed with fresh medium and recombinant human IL-2 followed by weekly re-stimulation using CTL:LCL and twice weekly addition of IL-2 for a 4 to 8 week period.

Dendritic cells for use in the process must also be prepared by taking PBMCs from a patient sample and activating them with IL-4 and GM-CSF to provide adherent PBMCs. These cells are then transduced with a viral vector Ad5f35-LMP1-LMP2 (i.e. encoding the EBV protein LMP1 and LMP2). Finally the dendritic cells are matured by the addition of IL-1β, IL-6, PGE-1 and TNF-α.

Summary of T Cell Expansion Steps
(Also Referred to as Preparation of Cytotoxic T Lymphocytes (CTLs))

Once prepared the transduced dendritic cells are cultured with fresh PBMCs from the patient for a period of about 10 days.

The T cells obtained from this step are then cultured with the transduced EBV-LCLs for a period of about 1 week.

Then the T cells obtained from the latter step are then cultured with transduced EBV-LCLs in the presence of IL-2 for a further 10 days to provide an autologous T cell antigen specific product This process is repeated until sufficient T cells have expanded.

J Immunother Vol 33, Number 3, April 2010 describes a faster and more efficient way of culturing the cells over a period of 23 days employing a system from Wilson Wolf known as the GRex™ system.

However, this rapid process still employs the traditional viral stimuli for the cells.

There are various problems with the prior art strategy:
(i) the use of live virus such as EBV and viral vectors has the potential to cause an immunodominant response against the vector which may interfere with efficient generation of target virus specific CT L's;
(ii) the use of live virus is an impediment to progression to phase 3 trials due to safety concerns;
(iii) the requirement for B cells to manufacture the EBV-LCL, now that Rituxan (which depletes B cells) has become standard therapy for most lymphoma patients means the technique cannot be employed for many patients;
(iv) the duration of manufacturing (a minimum of 6 weeks to establish the EBV-LCL and another 5 to 7 weeks for CTL expansion) is very inconvenient, impractical and economically challenging;
(v) the complexity of cell manipulation provides many opportunities for error and contamination of the product, hence, the principles of good manufacturing practice (GMP) are difficult to comply with, and
(vi) the autologous antigen presenting cells used to stimulate the T cell expansion can express antigens other than the target antigen, which may reduce the purity of the antigen-specific T cells which are desired for the therapeutic T cell product.

Nevertheless skilled persons have been reluctant to move away from the established processes because each step was thought necessary to generate a product with therapeutic characteristics and in particular to generate T cell populations that are suitable for recognizing cells infected by live viruses and cancers expressing viral antigens, in vivo.

The present disclosure provides a method for the rapid and efficient production of antigen specific T cells with specificity to a target antigen.

SUMMARY OF THE INVENTION

The present disclosure provides a process for in vitro expansion of antigen specific T cells such as autologous antigen specific T cells comprising the steps:
a) culturing a population of autologous PBMCs in the presence of:
i) dendritic cells which have been pulsed with a peptide/peptide mix relevant to a target antigen(s) OR a peptide/peptide mix relevant to a target antigen(s), and
ii) at least one cytokine, and
b) culturing a population of cells obtained from step a) in the presence of:
i) dendritic cells which have been pulsed with a peptide/peptide mix relevant to a target antigen(s) OR autologous antigen presenting T cells (T-APC's) cells which have been pulsed with a peptide/peptide mix relevant to a target antigen(s) and an artificial co-stimulatory factor, and
ii) optionally a cytokine, and
characterised in that the process does not employ live virus and/or viral vectors or the use of DNA or RNA encoded antigens in the expansion of the relevant T cell population.

In one embodiment there is provided a process for in vitro expansion of autologous antigen specific T cells comprising the steps:

a) culturing a population of autologous PBMCs in the presence of:
i) dendritic cells which have been pulsed with a peptide mix relevant to a target antigen(s), and
ii) at least one cytokine, and
b) culturing a population of cells obtained from step a) in the presence of:
i) autologous antigen presenting T cells (T-APC's) cells which have been pulsed with a peptide mix relevant to a target antigen(s) and an artificial co-stimulatory factor,
ii) a cytokine, and
characterised in that the process does not employ live virus and/or viral vectors or the use of DNA or RNA encoded antigens in the expansion of the relevant T cell population.

In the method of the present disclosure the PBMCs or dendritic cells in step a) and the antigen presenting cells of step b) are generally pulsed (also referred to as loading) with peptides selected to present epitopes from the target antigen. These peptides are discussed in more detail below.

We have overcome problems of the prior art by:
eliminating the need to generate EBV-LCL's, and therefore avoid the use of live virus, for antigen presentation (this allows the generation of antigen specific T cells from patients that have previously been B cell depleted, e.g. by Rituxan treatment)
eliminating the need to use viral vector-, or DNA-, or RNA-encoded antigen to achieve antigen expression and presentation in antigen presenting cells
providing an option to eliminate the use of DCs for antigen presentation
providing a method for T cell activation in which the stimulatory signal is provided by an autologous cell population and the co-stimulatory signal is provided by a recombinant cell line or an artificial co-stimulatory complex
providing an efficient and robust 2-step culture process to generate a total of, for example >10e7 CD3 T lymphocytes with suitable antigen specificity in three weeks or less.
focusing stimulation of the T cell with specificity for clinically relevant virus antigen, such as EBV antigens that are otherwise dominated by antigens that are not expressed in type 2 latency tumors (lymphoma and NPC).

The presently claimed invention has significant advantages for the manufacture of the autologous T cell products and potentially makes the therapy available to a wider population of patients. It also minimised the amount of time, intervention and resource required to produce a therapeutic product, and also advantageously minimises the opportunity for contamination.

Moreover, the specificity and properties of the therapeutic product obtained are at least equivalent to the product produced by the prior art methods and in a number of aspects may have improved properties.

Autologous cells from certain patients, such as cancer patients are different from cells obtained from healthy individuals because patient cells often are found to be anergic, i.e. incapable of delivering an immune response against antigens associated with the infection or cancer. Immune suppression is often considered to be systemic whereas anergy is usually described on an antigen-specific basis wherein a specific clone of T cells is no longer able to deliver an immune response against a target antigen. The cancer microenvironment, for example can create anergy such that T cells which recognize cancer antigens are no longer functional.

Evidence of the immune anergy or suppression is, for example the inability to clear virus infection and/or the presence of virus associated cancer cells. In healthy individuals these cells are cleared by the immune system (Teague, R. M., B. D. Sather, J. A. Sacks, M. Z. Huang, M. L. Dossett, J. Morimoto, X. Tan, S. E. Sutton, M. P. Cooke, C. Ohlen, and P. D. Greenberg. 2006. Interleukin-15 rescues tolerant CD8+ T cells for use in adoptive immunotherapy of established tumors. Nat. Med. 12:335-341 and Chemnitz, J. M., D. Eggle, J. Driesen, S. Classen, J. L. Riley, S. bey-Pascher, M. Beyer, A. Popov, T. Zander, and J. L. Schultze. 2007. RNA fingerprints provide direct evidence for the inhibitory role of TGF beta and PD-1 on CD4+ T cells in Hodgkin lymphoma. Blood 110:3226-3233).

Additionally, in patients with Nasopharyngeal Carcinoma (NPC), the results of autologous T cell immunotherapy with antigen-specific cytotoxic T lymphocytes (CTLs) have been relatively ineffective. In one trial only 1 of 11 patients had a complete response, and this may be explained by the inability to reactivate LMP-specific T cells from these patients. In fact the inventors hypothesise that NPC anergizes T cells with specificity for the viral tumour antigens.

Thus in some patients the prior art methods were unable to reactivate appropriate antigen specific T cells adequately.

Efficacy of infused T cells depends not only on their ability to recognize the targeted tumor antigens, but also to recognize multiple epitopes within those antigens to prevent tumor escape due to epitope loss, virus strain variation and T cell driven mutation. Hence there is a need to develop a manufacturing strategy which reproducibly reactivates and expands CTLs that recognize a broad repertoire of epitopes from the antigens, such as LMP1-LMP2-, EBNA1 and BARF1—that are expressed in NPC and in EBV-positive lymphomas.

Prior to the work by the present inventors, who are leaders in the field, it was not known whether peptides could be used to generate an autologous antigen specific T cell population for prophylaxis and treatment of viral infections and cancer associated with viruses. Nor was it known that dendritic cells or T-APCs employed in the present process could be rendered useful as antigen presenting cells employing said peptides. What is more the T cell responses to the peptides seem to be relevant in the context of naturally processed peptides which are recognized by the immune system.

The present invention represents a very significant advancement in the preparation of (autologous) antigen specific T cell preparation and this is likely to result in practical benefits for patients and medical practitioners. The factors that are in important in expanded T cell populations of the present disclosure are:
  the avidity of the T cells for each epitope recognized,
  the number of epitopes recognized within each antigen,
  the number of antigens recognized,
  the fold expansion of T cells and the frequency of T cells with the desired specificity.

BRIEF DESCRIPTION OF THE FIGURES

FIG. 1 shows a diagrammatic representation of a prior art process for generating EVB specific T cells. This method required the production of autologous dendritic cells (DC) for the first round of activation/expansion and Lymphoblastoid Cell Lines (LCL) for the subsequent rounds of activation/expansion. Both, Dcs and LCLs were transfected with adenoviral vectors containing the EBV antigens of choice in order to stimulate the growth of EBV specific T cells.

FIG. 2 shows a diagrammatic representation of the various embodiments of the invention. The diagram shows the process of the invention by demonstrating the use of peptides to generate EBNA1, LMP1 and LMP2 specific T cells. In all new methods the use of Adenoviral vectors as the way of providing the antigen(s) was replaced by the addition of exogenous peptide(s). Also the use of LCL for the second round of activation/expansion was abolished and replaced with either peptide loaded autologous DCs or peptide loaded antigen presenting autologous T cells (T-APC) and aK562 cells. Another embodiment shows that the first stimulation can be performed without the use of DC and utilizes the antigen presenting cells present in the PBMC population.

Figure 6E:
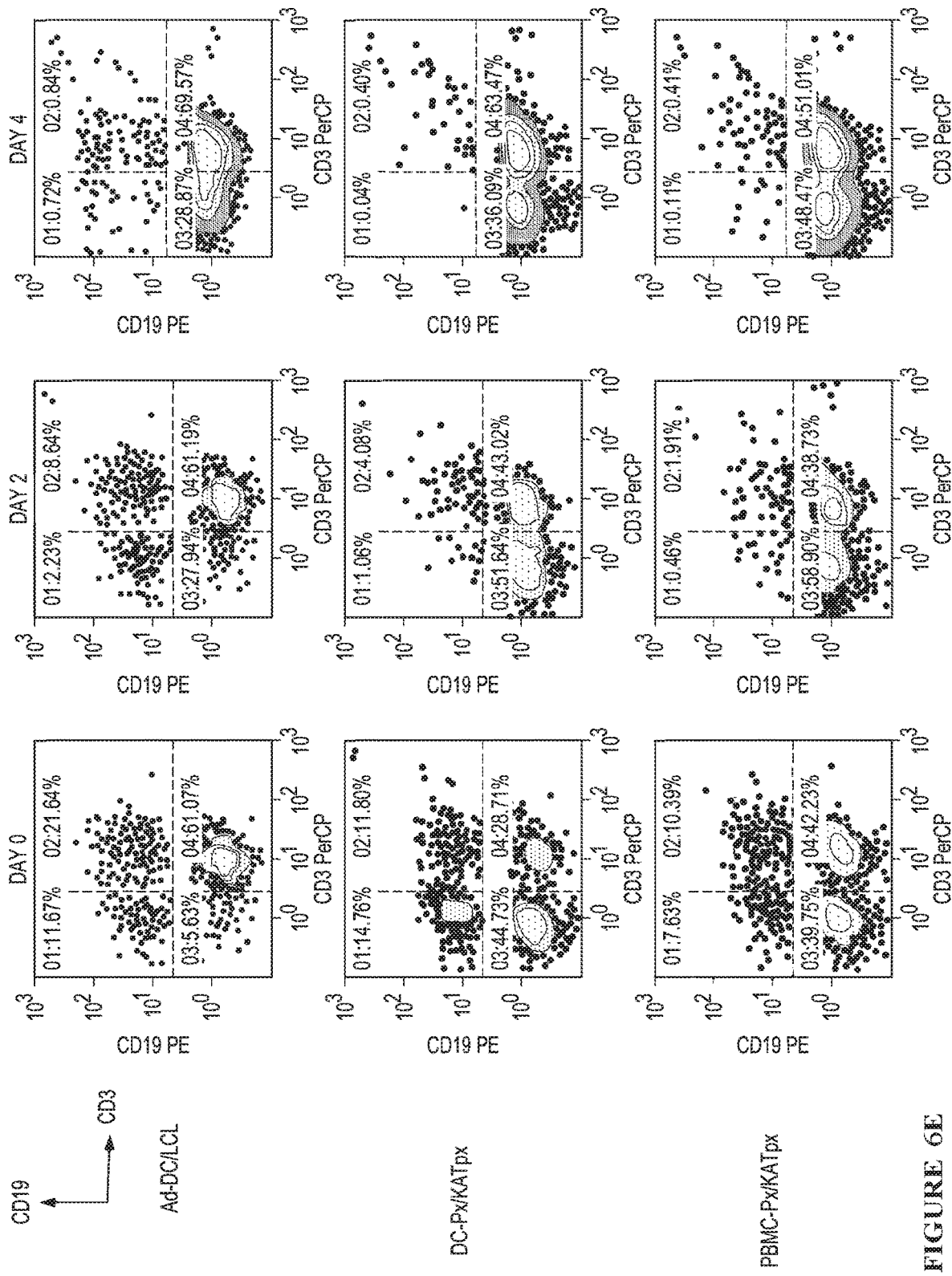

The generation of PBMCs, DCs and T-APCs is described in this document under Protocol 1, 2 and 3 respectively.

FIGS. 3A-3E show the stimulation of T cell expansion by aK562 using T-APCs in step b) of claim 1 of the invention. This demonstrates the use of a novel system to achieve a powerful antigen specific T cell stimulation for the second round of activation/expansion. It is based on the surprising discovery that the first (antigen specific, stimulatory) signal and the second (co-stimulatory) signal can be provided by two separate components. In the example shown the first signal is provided by peptide loaded T-APCs and the second signal is provided by the aK562 cells that have been modified to present co-stimulatory molecules but not MHC. This is as explained in step b) of claim 1 of the invention.

FIG. 3A shows the expansion of T cells using aK562 and T-APCs according to the second stimulation in the invention.

FIG. 3B shows the expansion of T cells using aK562 and T-APCs according in step b) of claim 1 of the invention. This Figure shows the result in 6 normal donors of using the different ratios of CTL:T-APC:aK562 during the second stimulation of the process and the resulting cell expansion. The 1:1:5 ratio was shown to be the most optimal in the majority of donors.

FIG. 3C shows the optimal CTL to aK562 to T-APC ratio for T cell expansion in step b) of claim 1 of the invention. The results were generated by comparing (C) the fold expansion (as individually demonstrated in FIG. 3A), (D) the percentage of CD56+, CD3− cells in the culture and (E) the response in an Interferon-y (IFNg) ELISPOT of the final cell product generated using the different cell to cell ratios (SCF=Spot forming colonies).

FIG. 3D shows a comparison of interferon gamma secreting cells in cultures of EBV specific T cells employing various ratios of CTLs to T-APCs to aK562 cells and different antigens. The number of cells in the final culture producing IFNg in an ELISPOT assay is shown in 2 individual donors following the second stimulation at the different culture ratios. This is shown for the 3 individual EBV antigens of interest and a control without antigen.

FIG. 3E shows that T-APC can act as antigen presenting cells for HLA class I and II restricted antigens.
  A. Upon activation of PBMC with OKT3 and CD28 antibodies (T-APC), T cells will start to upregulate HLA class II as well as co-stimulatory molecules such as CD80, CD83, CD86 and 4-1BBL. Even though HLA class II will reach up to 100% by the end of a week, the level of co-stimulatory molecules is transient and remains low.
  B. aK562 is an HLA(−)ve leukemia cell line that has been engineered to express stable and high level of CD80, CD83, CD86 and 4-1BBL.

FIGS. 4A-4G show the results using the prior art and the various embodiments of the invention to expand EBV specific cells from healthy donors FIG. 4A is a schematic representation of the steps of the prior art process and various embodiments of the invention and their nomenclature. This diagram shows the prior art in a shaded box and the nomenclature used to reference the first and second stimulations. The cell type used as the APC is shown first and then the way the antigen was delivered (Ad vector or Peptides—Px). For the embodiment using T-APC and aK562 plus peptide this is abbreviated in the data to ATC.

FIG. 4B shows expansion of EBV-specific T cells using the prior art and the various embodiments of the invention. This Figure shows the summary of results from 9 healthy donors. Following expansion of EBV specific T cells using the prior art and the 3 other methods outlined in FIG. 4A, cells were counted at day 9, 16 and 23 and the results displayed below as millions of cells. Both methods employing aK562 in combination with DCs or T-APCs show FIG. 4C shows a comparison of interferon gamma secreting cells in cultures of EBV specific T cells using the prior art and the various embodiments of the invention. Following culture using the prior art method and the various embodiments of the invention, the cell populations were re-stimulated with peptides in an ELISPOT assay. Peptides from the three antigens of interest (EBNA-1, LMP1 and LMP2) were used in the assay and the response was either the same or enhanced when compared to the prior art. One representative example (of a total of 9 healthy donors) is shown.

FIG. 4D shows a graph collating the information from all normal donors for the embodiments using ATC.

FIG. 4E shows the T cell receptor affinity for EBV specific T cells expanded by the prior art and the various embodiments of the invention. Cells were cultured to day 16 using the different methods outlined in FIG. 4A they were then re-stimulated with increasing dilutions of peptide in an ELISPOT assay to determine if the new embodiments of the invention would be detrimental to the avidity of the T cell receptors to peptide. In fact the new methods show a similar and in the case of EBNA1 significantly increased avidity for the individual EBV peptides.

FIG. 4F shows the distribution of various T cell markers for cells that were expanded using the prior art and the various embodiments of the invention. At day 16 T cells produced using the 4 different methods were harvested and immune-phenotyped using flow cytometry. This shows that the composition of the cell products is unchanged between the prior art method and the embodiments of the invention. There is a difference between the prior art and the new embodiments in terms of the expression of CD62L. This is expressed on naïve and central memory T cells and is down regulated by effector memory T cells therefore this again could be seen as an advantage for the embodiments of the invention.

FIG. 4G shows that culture of cells using the prior art skews responses towards antigens expressed in LCL cells rather than on the latency type 2 antigens present in EBV+ cancer cells from lymphoma and NPC patients. Cells were generated using the prior art and embodiments of the invention. These were then re-stimulated with a variety of EBV peptides in an ELISPOT assay. This shows that the prior art method skews the response towards specific LCL dominant epitopes whereas the new methods show increased activity against cancer associated antigens such as EBNA1.

FIGS. 5A-5G show the results using the prior art and the various embodiments of the invention to expand EBV specific cells from NPC patients FIG. 5A is a schematic representation of the steps of the prior art process and various embodiments of the invention and their nomenclature. This diagram shows the prior art in a shaded box and the nomenclature used to reference the first and second stimulations. The cell type used as the APC is shown first and then the way the antigen was delivered (Ad vector or Peptide—Px). For the embodiment using T-APC and aK562 plus peptide this is abbreviated in the data to ATC.

FIG. 5B shows expansion of EBV-specific T cells using the prior art and the various embodiments of the invention. Following expansion of EBV specific T cells using the prior art and the 3 other methods outlined in FIG. 5A, cells were counted at day 9, 16 and 23 and the results displayed below as millions of cells or fold expansion. This is representative of 3 and 4 NPC donors respectively. Both methods employing aK562 in combination with DCs or T-APCs show significantly better expansion than the prior art.

FIG. 5C shows the expansion of EBV-specific T cells by fold.

FIG. 5D shows a comparison of interferon gamma secreting cells in cultures of EBV specific T cells using the prior art and the various embodiments of the invention. Following culture using the prior art method and the various embodiments the cell populations were re-stimulated with peptides in an ELISPOT assay. Peptides from the three antigens of interest were used-EBNA-1, LMP1 and LMP2 and the response in NPC patients was enhanced when compared to the prior art. One representative example is shown.

FIG. 5E shows the T cell receptor affinity for EBV specific T cells expanded by the prior art and the various embodiments of the invention. Cells were cultured to day 16 using the different methods outlined in FIG. 5A. They were then re-stimulated with increasing dilutions of peptide in an ELISPOT assay to determine if the new embodiments of the invention would be detrimental to the avidity of the T cell receptors to peptide. In fact the new methods show a similar and in the case of EBNA1 significantly increased avidity for the individual EBV peptides.

FIG. 5F shows the distribution of various T cell markers for cells that were expanded using the prior art and the various embodiments of the invention. At day 31T cells produced using the 4 different methods described in FIG. 5A were harvested and immune-phenotyped using flow cytometry. This shows that the composition of the cell products in unchanged between the prior art method and the embodiments of the invention. There is a difference between the prior art and the new embodiments in terms of the expression of CD62L. This is expressed on naïve and central memory T cells and is down regulated by effector memory T cells therefore this again could be seen as an advantage for the embodiments of the invention.

There is some change as to the methods outlined in FIG. 5A. This is due to the NPC patient cells being subjected to more than one re-stimulation step. However the nomenclature for each stimulation remains the same. This data is representative of 4 NPC patients.

FIG. 5G shows that T Cells from NPC patients expanded employing the new embodiments of the invention (CD3+/CD19-) kill LCL (EBV+ cancer cell-line, CD3-/CD19+) better in co-culture for 4 and 10 days as T cells expanded by the prior art. T cells and LCL were incubated at a 1:1 ratio.

FIGS. 6A-6E show the results using the prior art and the various embodiments of the invention to expand EBV specific cells from lymphoma patients FIG. 6A is a schematic representation of the steps of the prior art process and various embodiments of the invention and their nomenclature. This diagram shows the prior art in a shaded box and the nomenclature used to reference the first and second stimulations. The cell type used as the APC is shown first and then the way the antigen was delivered (Ad vector or Peptides—Px). For the embodiment using T-APC and aK562 plus peptide this is abbreviated in the data to ATC as previously but also has been alternatively abbreviated to KATpx and ATpk in this section of the data.

FIG. 6B shows expansion of EBV-specific T cells using the prior art and the various embodiments of the invention. Following expansion of EBV specific T cells using the prior art and the 3 other methods outlined in FIG. 6A, cells were counted at day 9 and 16 and the results displayed below as millions of cells or fold expansion. This is representative of results with cells from 4 lymphoma patients.

FIG. 6C shows expansion of EBV-specific T cells by fold.

FIG. 6D shows a comparison of interferon gamma secreting cells in cultures of EBV specific T cells using the prior art and the various embodiments of the invention. Following culture using the prior art method and the various embodiments the cell populations were re-stimulated with peptides in an ELISPOT assay. Peptides from the three antigens of interest were used—EBNA-1, LMP1 and LMP2 and the response in lymphoma patients was enhanced when compared to the prior art. One representative example is shown. These results show that when peptide pulsed PBMCs or DCs were used for the first expansion, the number of antigen specific T cells was significantly increased after 9 days relative to culture where the prior art was used.

FIG. 6E shows that T Cells from lymphoma patients expanded employing the new embodiments of the invention (CD3+/CD19−) kill LCL (EBV+ cancer cell-line, CD3−/CD19+) equally well or better in co-culture for 2 or 4 days as T cells expanded by the prior art. T cells and LCL were incubated at a 1:1 ratio.

FIGS. 7A-7C show the results using the prior art and the various embodiments of the invention to expand VZV specific cells from healthy donors. PBMCs were pulsed with overlapping peptide libraries (15 mers overlapping by 11 amino acids) (pepmixes) spanning the VZV proteins, gE, ORF10. 1E61, 1E62 and 1E63 in the presence of IL-4 and IL-7. On days 9, 16 and 23 they were restimulated with autologous activated T cells (AATCs, T-APCs) pulsed with the same pepmixes in the presence of aK562 cells expressing co-stimulatory molecules CD80, CD83, CD86 and 4-1BB ligand (K562-cs), at a ratio of CTLs to T-APCs to K562-cs of 1:1:5. Their rate of proliferation was measured by counting and antigen-specificity was measured in gamma interferon ELISPOT assays.

FIG. 7A is a schematic representation of the steps of the prior art process and various embodiments of the invention and their nomenclature FIG. 7B shows expansion of EBV-specific T cells using the prior art and the various embodiments of the invention. Growth rate of T cells expanded using the protocol described above. >500 fold expansion can be achieved over 22 days FIG. 7C shows a comparison of interferon gamma secreting cells in cultures of EBV specific T cells using the prior art and the various embodiments of the invention. Frequency of T cells from 6 to 9 healthy VZV-seropositive donors that secrete gamma interferon in response to stimulation with VZV peptides after activation with pepmix pulsed PBMCs or DCs on day 0 and pepmix-pulsed autologous activated T cells (T-APCs) plus K-562-cs cells on days 9, 16 and 23. Each symbol represents one donor. Embodiments of the current invention either using peptide pulsed PBMCs or DCs during the first expansion and T-APCs in combination with aK562s for subsequent expansions result in a significant expansion of target CTLs across the various VZV antigens used.

DETAILED DESCRIPTION OF THE INVENTION

Autologous T cells are cells derived from the patient i.e. cells that are natural to the patient as opposed to cells from a donor. Certain tumours associated with viral infection have developed a way to grow in the patient despite the presence of virus-specific T cells. This involves the expression of molecules that are inhibitory to T cells and the modulation of virus gene expression. Thus the T cells in these patients may have reduced function towards the cancer cells, which may be described as a form of anergy. In autologous T cell therapy a sample of T cells are removed from the patient for activation and expansion ex vivo. Once the antigen-specific T cell population has been prepared it is infused into the patient where the T cell cells will further expand and will eliminate cells presenting their target antigens by direct (cytotoxic) and indirect (immune regulatory) mechanisms.

"T cell" is a term commonly employed in the art and intended to include thymocytes, immature T lymphocytes, mature T lymphocytes, resting T lymphocytes or activated T lymphocytes. A T cell can be a T helper (Th) cell, for example a T helper 1 (Th1) or a T helper 2 (Th2) cell. The T cell can be a CD4+ T cell, CD8+ T cell, CD4+CD8+ T cell, CD4−CD8− T cell or any other subset of T cells.

Antigen specific T cell as employed herein is intended to refer to T cells that recognise a particular antigen and responds thereto, for example by proliferating and/or producing cytokines in response thereto.

In one or more embodiments the process does not employ recombinant target antigens for stimulating specificity. Recombinant antigens herein refers to whole or large fragments of antigens prepared by recombinant techniques. In contrast the peptides employed are small fragments of antigen and are generally synthetic.

The present invention relates to ex vivo processing of cells and the T cell products obtained therefrom. Usually the present invention does not include the step of obtaining the sample from the patient. The step of obtaining a sample from the patient is a routine technique of taking a blood sample (which can be processed and optionally provided as an apheresis product). This process presents little risk to patients and does not need to be performed by a doctor but can be performed by appropriately trained support staff. In one embodiment the sample derived from the patient is approximately 200 ml of blood or less, for example 150 ml or less such as in the range 100-150 ml. Generally at least about 60 ml of blood is required.

Typically the PBMCs for T cell expansion, DC generation and T-APC generation are obtained from the blood or apheresis product by Ficoll density gradient separation known to those skilled in the art. Ficoll density gradient separation employs a synthetic sucrose polymer the concentration of which varies through the solution to exploit the separation of different cells during sedimentation. Suitable reagents are available, for example from GE Healthcare, such as Ficoll Paque™ PLUS.

In one embodiment the centre responsible for taking the blood sample or for shipping the blood sample processes the sample by Ficoll density gradient separation prior to transportation.

In one embodiment the blood sample or processed blood sample is transported at ambient temperature, for example above 4° C. and below about 30° C.

In one embodiment the blood sample or processed blood sample is filled into a container, such as bag, comprising two chambers, wherein one chamber contains additives, such as preservatives and/or anticoagulants and the blood or processed blood is filled into the second chamber, after which a seal between the first and second chamber is broken and the contents of the two chambers are mixed. Culturing cells as employed herein is intended to refer to activating and expanding and/or differentiating cells in vitro.

It is known to the skilled person, that expansion of T cells is generally performed in a suitable T cell expansion medium. Generally the process of step a) can be performed without changing the medium. Generally the process of step b) can be performed without changing the media. However, media should be changed if indicated by a glucometer, for example that is if the glucose in the system falls below 100 mg/dl. Thus the process of the present disclosure is efficient in that it minimizes the amount of intervention required to expand the T cells.

T cell expansion may be evaluated by counting viable CD3+ cells.

Viable cells can be tested by cell staining with, for example Trypan blue (and light microscopy) or 7-amino-actinomycin D, vital dye emitting at 670 nm (or Via Probe a commercial ready-to-use solution of 7AAD) and flow cytometry, employing a technique known to those skilled in the art. Where the stain penetrates into the cells the cells are considered not viable. Cells which do not take up dye are considered viable. An exemplary method may employ about 5 μL of 7AAD and about 5 μL of Annexin-V (a phospholipid-binding protein which binds to external phospholipid phosphatidylserine exposed during apotosis) per approximate 100 μL of cells suspension. This mixture may be incubated at ambient temperature for about 15 minutes in the absence of light. The analysis may then be performed employing flow cytometry. See for example M G Wing, A M P Montgomery, S. Songsivilai and J V Watson. An Improved Method for the Detection of Cell Surface Antigens in Samples of Low Viability using Flow Cytometry. J Immunol Methods 126: 21-27 1990.

T cell expansion media generally comprises serum, media and any cytokines employed in the relevant expansion step (i.e. step a) or step b)).

In one embodiment the serum employed is, for example 15% serum or less such as 10% serum, in particular human serum is employed.

In one embodiment the media is Advanced RPMI or RPMI 1640, available form Life Technologies.

In one embodiment the cytokines employed are discussed below.

In one embodiment the cell expansion medium comprises 10% human AB serum, 200 mM L-glutamine, 45% Earle's Ham's amino acids (EHAA or Click's medium) and 45% advanced RPMI or RPMI-1640.

In one embodiment the media employed does not require the use of serum.

Cell expansion as employed herein refers to increasing the number of the target cells in a population of cells as a result of cell division.

In one embodiment in step a) the PBMCs are treated directly with a peptide/peptide mix. It was very surprising that autologous PBMCs could activate T cells in the presence of peptides in a manner similar to when autologous dendritic cells are present, in particular because the message from the literature is that dendritic cells are the optimal antigen presenting cells. Chen M L, Wang F H, Lee P K, Lin C M. Immunol Lett. 2001 Jan. 1; 75(2):91-6.

In another embodiment in step a) of the present process dendritic cells are employed which are prepared from the patients PBMCs.

The blood sample is not generally subject to initial physical selection of cells, for example selection of a subpopulation of cells (or T cells) from an apheresis population.

In one embodiment 1 to $2\times10^7$ PBMCs are stimulated with 0.5 to $1\times10^6$ peptide-pulsed DCs in the presence of cytokines in the GRex40 in 30 mls of medium. A harvest of cells, for example in the range 50 to $80\times10^7$ antigen-specific responder T cells after 9 to 14 days of culture. However this may be lower in patients with anergic T cells.

Medium (45% advanced RPMI, 45% EHAA, 10% FCs and 200 mM L-glutamine) will be changed only if indicated by a drop in glucose below 100 mg/dl (on glucometer).

Dendritic cells are often referred to, by those skilled in the art, as professional antigen presenting cells. The term refers to the fact that dendritic cells are optimal in delivery the two signal activation process to T cells, i.e., in addition to presenting antigen on the cell surface, dendritic cells also provide a strong co-stimulatory signal. Both signals, stimulation by antigen presentation and co-stimulation are required to achieve T cell activation.

Dendritic cells for use in the process of the present invention may be generated from a sample of the patients PBMCs by pulsing (or loading) with a peptide mixture the details of which are discussed below. Pulsing or loading as employed herein is intended to refer simply to exposing the relevant cells, such as PBMCs or dendritic cells, to the peptide mix in an appropriate medium.

Dendritic cells for use in the process may be prepared by taking PBMCs from a patient sample and adhering them to plastic. Generally the monocyte population sticks and all other cells can be washed off. The adherent population is then differentiated with IL-4 and GM-CSF to produce monocyte derived dendritic cells. These cells may be matured by the addition of IL-1β, IL-6, PGE-1 and TNF-α (which upregulates the important co-stimulatory molecules on the surface of the dendritic cell) and are then transduced with a peptide mixture as described herein to provide the required dendritic cells. Reference to generating and maturing DC in this way is found in Jonuleit H, Kuhn U, Muller G, et al. Pro-inflammatory cytokines and prostaglandins induce maturation of potent immunostimulatory dendritic cells under fetal calf serum-free conditions. Eur J Immunol. 1997; 27:3135-3142.

Peptides may be added at 1 to 100 ng peptide/$15\times10^6$ PBMCs or ATCs (see discussion below) or 1 to 100 ng peptide per $2\times10^6$ DCs for each peptide library/pepmix.

In one embodiment PBMCs are stimulation with IL-4 and GM-CSF for 3 to 5 days followed by 1 or 2 days of maturation with GM-CSF, IL-4, TNF-a, IL-Ib, PGE-1 or PGE-2 and IL-6 followed by pulsing with said peptides.

Thus in one embodiment the dendritic cells in step a) are autologous.

In one embodiment the dendritic cell response produced is balanced, CD4 and CD8 response.

Balanced CD4 and CD8 response as employed herein is intended to refer to the fact that the CD4 cells or CD8 are not depleted in the expansion process. However a balanced population as employed herein may still be skewed in that there may be more CD4 cells than CD8 cells or vice versa.

In one embodiment the ratio of PBMCs to dendritic cells in step a) in the range 10:1 to 50:1 respectively, for example 15:1, 16:1, 17:1, 18:1, 19:1, 20:1, 21:1, 22:1, 23:1, 24:1, 25:1, such as about 20:1.

Dendritic cells provide powerful activation of T cells and when the frequency of antigen-specific T cells in the culture is low (less than 1 in 100 T cells may be specific for the antigens of interest), for example in step a) it is efficient to employ dendritic cells. However, as the numbers and frequency of antigen specific T cells expand and the ratio of specific T cells to dendritic cells increases the efficiency of the activation of the dendritic cells decreases unless the number of dendritic cells can be increased. The antigen-specific T cells will frequently deliver a cytotoxic response to the dendritic cell following activation. The killing of the dendritic cells will then reduce the activation signal available to continue activating and expanding the target antigen-specific T cells.

Whilst dendritic cells are very effective in stimulating T cells to expand into populations specific to a target antigen it is difficult to generate large quantities of dendritic cells. Thus whilst step b) may employ dendritic cells in practice there are advantages to employing different antigen presenting cells and an artificial co-stimulator factor in step b). In some instances when the number of dendritic cells to T cells is too small no activation of the T cells is observed. This is discussed in more detail below. Advantageously, dendritic cells are thought to be capable of activating both memory T cells and naïve T cells. The presence of memory T cells in the cell populations according to the present invention may be important.

Minor population as employed herein is intended to refer to the fact that the absolute numbers of cells in the minor population is significantly lower than the number of cells in the desired population, for example 30 percent or less of the total population.

The peptide mixtures described below may be used for one or more purposes selected from pulsing of dendritic cells, pulsing of antigen presenting cells or may be employed directly with PBMCs in step a). The peptide mixes are from a relevant viral antigen, for example an EBV viral antigen. Epstein-Barr virus, frequently referred to as EBV, is a member of the herpes virus family and chronically infects over 95% of the world population.

In one embodiment the peptides are from an antigen of papilloma virus.

In one embodiment the peptides are from an antigen of hepatitis C virus.

In one embodiment the peptides are from an antigen of vaccinia virus (VV).

In one embodiment the peptides are from an antigen of varicella zoster virus (VZV).

In one embodiment the peptides are from an antigen of human immunodeficiency virus.

In one embodiment the peptides are from an antigen of Hepatitis B, HHV-8, CMV, HTLV-1, SV40 and/or merckel cell virus.

In one embodiment the peptides are from a combination of viruses, for example any two or more described herein, such as EBV and VZV, EBV and VV, VZV and VV or EBV, VZV and VV.

Instead of culturing the autologous T cells in the presence of cells that are infected with the relevant virus, such as EBV, or in the presence of adenovirus vectors encoding viral proteins the cells are cultured in the presence of antigen presenting cells that were pulsed with a peptide or a mixture of peptides. This reduces the risk of contamination of the final product with pathogens which is important because there is no method of sterilizing the T cell product that will be infused into the patient. In one embodiment the peptide mix or some of the peptides in the mix cover part or all of the sequence of the antigen LMP1 (Latent Membrane Protein 1 Uniprot number P03230).

In one embodiment the peptide mix or some of the peptides in the mix cover part or all of the sequence of the antigen LMP2 (Latent Membrane Protein 2 Uniprot number Q1HV.12).

In one embodiment the peptide mix or some of the peptides in the mix cover part or all of the sequence of the antigen EBNA 1, 2, 3, 4, 5 or 6 or a combination of the same, in particular EBNA 1.

Epstein-Barr nuclear antigen 1 (EBNA1) is a multifunctional, dimeric viral protein associated with Epstein-Barr virus. It is the only viral protein of EBV that is found in all EBV-related malignancies and therefore is a significant antigen to target. It is important in establishing and maintaining the altered state that cells take when infected with EBV. EBNA1 possesses a glycine-alanine repeat sequence that separates the protein into amino- and carboxy-terminal domains. This sequence also seems to stabilize the protein, preventing proteasomal breakdown, as well as impairing antigen processing and MHC class I-restricted antigen presentation. This thereby inhibits the CD8-restricted cytotoxic T cell response against virus-infected cells. The EBNA1 transcript area originates at the Qp promoter during latency phases I and II. It is the only viral protein expressed during the first latency phase. The EBNA1 pepmix activates HLA class II-restricted cytotoxic CD4 T cells.

In one embodiment the peptide mix or some of the peptides in the mix cover part or all of the sequence of the antigen BARF 1 (BamHI A rightward reading frame 1, Uniprot number Q777A5). BARF1 is a 221 amino acid protein encoded by the BARF 1 gene which is located in the BamHI-A fragment of the EBV genome. BARF1 is expressed in various EBV-associated epitheloid malignancies, for example in NK/T lymphomas and in Burkitt's lymphoma.

Other potential EBV antigens include LP and BHRF1.

The major virion/envelope proteins for vaccinia virus are described in PNAS January 7, 203 vol 100 no. 1 page 217-222 (Drexler et al). These include A1OL (major core protein p4a), H3L (heparin binding protein), C7L (host range protein 2), D8L (cell surface binding protein), B22R (unknown function) and G5R (unknown function).

Varicella zoster virus immunogens include gE, ORF10, 1E61, 1E62 and 1E63.

Peptides from each one of the specific target antigens listed supra may independently be employed in step a) and/or step b) of the process.

Generally some or all of the epitopes/antigens/peptides employed or expressed for the purpose of providing a primary signal for T activation in step a) and step b) will be common to both steps. The peptides may cover part or all of the target antigen, for example may be overlapping to increase the opportunity of presenting the amino acids of an epitope in an immunologically relevant way. Alternatively or additionally peptides of known epitopes may be included and if desired over-represented, that is to say may be a more significant percentage of the peptides presented.

Antigens in HIV include gag, pol, env, nef, gp180, gp120 and the like.

"Covers part or all of the sequence of the antigen" as employed herein is intended to refer to the fact that there is identity or significant similarity between the peptide and the relevant portion of the full length antigen, for example the peptide is substantially identical to a contiguous region of the antigen.

Selected to present epitopes as employed herein is intended to refer to the fact that the linear sequence of an epitope is known and included into a peptide mix (that is peptides are selected encoding known epitopes) or, for example where the antigen sequence has not been epitope mapped then the peptides are designed to cover part or all of the sequence in an overlapping manner to maximise the opportunity of presenting one or more appropriate epitopes. Of course a mixture of these two strategies can be employed if desired, for example known epitopes may be represented to a greater extent in a peptide mixture.

In one embodiment the peptides in the mix are from one or more relevant viral antigens, for example one, two, three, four or more.

In one embodiment the peptide mix comprises or consists of sequences from at least LMP1 and LMP2. In addition in one embodiment EBNA1 and/or BARF1 are added to the antigen mixture to reduce the chances of immune escape by mutation or down-regulation of viral antigens.

Peptide as employed herein intended to refer to short polymers of amino acids linked by peptide bonds, wherein the peptides contain at least 2 but generally not more than 50 amino acids.

The peptides employed are sufficiently long to present one or more linear epitopes, for example are on average 7, 8, 9, 10, 11, 12, 13, 14, 15, 16, 17, 18, 19 or 20 amino acids long.

In one embodiment some of the peptides of the mixture overlap (in relation to the sequence of a single antigen), that is to say that they are from a single antigen and are arranged such that portions of the fragments and certain sequence of amino acids from the parent sequence occur in more than one peptide fragment of the mix. The overlap of the peptides means that there is redundancy in the amino acid sequence. However, this method maximises the opportunity to present epitopes from the parent antigen in an appropriate manner, particularly when epitope mapping information is not available for the parent antigen.

In one embodiment 1, 2, 3, 4, 5, 6, 7, 8, 9, 10, 11, 12, 13, 14 or 15 amino acids overlap in each peptide. In one embodiment the peptides in the libraries for each protein are 15 amino acids long and overlap by 11 amino acids so that all potential HLA class I epitopes can be presented from a protein. The peptides can be longer, for example 20 amino acids overlapping by 15 or 30 amino acids overlapping by 25.

Examples of suitable peptides sequences include in the sequence listing filed herewith.

In one embodiment the peptide mix comprises or consists of 2-1000 peptides, more specifically 2-500, for example 2-400, 2-300, 2-200 or 2-100 such as 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200 or more peptides.

The peptides of step a) or the peptides employed to create antigen specific dendritic cells in step a) or b) or employed to prepare the antigen presenting cells of step b) of the process are independently, selected based on the criteria above. However, the process is most efficient where the some or all of the peptides employed or the materials such as dendritic cells and/or antigen presenting cells employed are pulsed with some or all of the same epitopes. In this situation step b) then reinforces and augments the responses generated in step a).

The peptide mixes described above may also be used to generate antigen presenting T cells (T-APCs) which are employed in some embodiments in step b) of the process. To prepare the antigen presenting T cells, they are generated form PBMCs as described below and are pulsed with a relevant peptide mix, for example peptides are added at 1 to 100 ng peptide/$15 \times 10^6$ T-APCs for each peptide library. Each library as employed herein may refer to the peptides made for each antigen.

In one embodiment the antigen presenting cells are autologous.

Activated T cells express HLA class I and upregulate class II antigens as well as CD80 and CD86 (transiently).

In one embodiment after pulsing with peptides to provide the specific T-APCs the latter are irradiated to ensure that they don't expand any further when they are employed in step b).

Irradiation may be effected employing a source of gamma radiation or a source of X-rays.

In one embodiment on day 9 to 14, about $5 \times 10^7$ responder T cells from step a) are stimulated with $5 \times 10^7$ irradiated T-APCs and $5 \times 10^7$ aK562s in a GRex 500 in 400 mls of medium containing IL-15 for up to 14 days.

US 2003/0147869 discloses that the aK562 cells described therein may be engineered to render them antigen presenting cells. These cells in theory could be expressed in significant numbers. One may think that these could be employed as an alternative to T-APCs of step b). However these aK562 antigen presenting cells do not express HLA and if they did the HLA phenotype would not match the effector T cell restriction pattern and they would activate alloantigen-specific T cells. The present inventors have found that in the absence of HLA-expressing cells there is poor activation of the relevant target T cell population. Whilst in theory these aK562 cells could be engineered to express HLA this would be need to be matched to the patient in each case thereby making the process unnecessarily complicated and expensive.

There are 7,196 HLA alleles. These can be divided into 6 HLA class I and 6 HLA class II alleles for each individual (on 2 chromosomes). They can be mixed and matched in any way and therefore introducing the appropriate combination of HLA alleles into aK562 cells to (1) reactivate all potential T cells and (b) induce no allo-reactivity would be impossible at this moment in time.

The T-APCs according to the present invention present on average at least one epitope from a target antigen and for example may present 2, 3, 4, 5, 6 or more epitopes.

In one embodiment the T-APCs present epitopes from more than one target antigen, for example 2, 3, 4 or more target antigens.

In one embodiment the ratio of cells (or CTLs) obtained from step a) to T-APCs is in the range 4:1 to 1:2, for example 1:1. A high proportion of T-APCs maximises the efficiency of the expansion. Usually it is difficult to generate dendritic cells is such high proportions, which means the time taken for expansion of the relevant T cell population may be longer with dendritic cells than the time taken for expansion with antigen presenting cells. In some instances where the numbers of the dendritic cells are very low the expansion may not occur at all. Thus the process employing antigen presenting cells in step b) may be advantageous in that the periods taken for expansion are shorter and thus provide a more efficient process.

Thus in one embodiment T-APCs are employed in step b) of the present method.

The use of T-APCs in the present process replaces the use LCLs in the prior art process. LCL cell lines are immortalised by infection with live EBV virus. Avoiding the use of LCLs in the present process is a huge advantage.

LCLs engineered to present other viral antigens through infection with adenovirus vectors, or pulsed with peptides can provide an effective second stimulation, but for weak antigens, both adenoviral and EBV proteins from the vector and the LCL respectively produce strong competition, so that the major component of the final CTL product is often specific for adenovirus or dominant EBV antigens expressed in LCLs but not expressed in type 2 latency tumors (lymphoma and NPC).

The use of simple peptides in step b) does not seem viable because the inventors' experience is that presenting peptide mixes to the CTLs resulting from step a) simply "confuses" the cells and results in them presenting peptides on their surface. This then results in the CTLs being targets for each other and they start to destroy themselves. This causes depletion of the cells which is clearly undesirable and contrary to the purpose of performing the process.

In one embodiment step b) is performed more than once, for example 2, 3, 4, 5 or more times until sufficient numbers of the relevant antigen specific T cell population are obtained.

Sufficient numbers may, for example be sufficient cells to continue expanding in vivo and stimulating the patient's immune response to the target virus infection and/or target associated cancer, such as 1 to $90 \times 10^3$, 1 to $90 \times 10^4$, 1 to $90 \times 10^5$, 1 to $90 \times 10^6$, 1 to $90 \times 10^7$, 1 to $90 \times 10^8$ or more cells, such as $80 \times 10^7$ cells.

In one embodiment there is provided a process wherein if cells do not expand sufficiently after step b) they may receive additional stimulation with:
(1) peptide-pulsed, irradiated autologous activated T cells and irradiated co-stimulatory aK562 cells,
(2) irradiated PBMCs from blood bank approved allogeneic donors and/or
(3) submitogenic doses of anti-CD3; 1 to 100 ng per mL for example 50 ng per ml.

T-APCs are not professional antigen presenting cells. Therefore, in addition to the antigen presentation provided by the T-APCs a co-stimulator factor is required to stimulate T cell expansion and differentiation.

An artificial co-stimulatory factor as employed herein is an exogenous factor which is added to the culture to provide a T cell activation signal to complement the T-APC antigen presentation signal, for example where together the co-stimulatory factor and the T-APC antigen presentation signal stimulates or facilitates the autologous T cells expanding in a specific manner i.e. that stimulates the target population of cells as they expand to be specific for the target antigen, wherein the specificity aspect is elicited by the T-APC. An exogenous factor is one that is not present in the culture of PBMCs without addition or where the naturally occurring amounts present in the cell culture are low and are augmented by addition of exogenous amounts of the factor.

Beads bearing CD80/86 may be employed as a co-factor. Beads with anti-CD28 (ligand for CD80/86) and anti-4-1BB are available but they also contain anti-CD3 which eliminates the desired antigen mediated specificity of the expansion. Thus beads with anti-CD28 (ligand for CD80/86) and anti-4-1BB in the absence of anti-CD3 form an aspect of the present disclosure.

In one embodiment the artificial co-stimulatory factor is a cell or cell-line engineered to express particular protein(s) on its surface or associated with its surface (see US 2003/0147869 for association of certain antibodies on the surface of the cell), for example a HLA negative cell line and which has been genetically modified to express co-stimulatory molecules, such as the aK562 cell-line as disclosed in U.S. Pat. No. 7,745,140. Cell lines such as the latter may be employed in the process of the invention to provide a prolonged co-stimulatory signal.

Thus in one embodiment the cell line such as aK562 does not express HLA.

Thus in one embodiment the cell line such as aK562 does not express antigen.

aK562 cell as employed herein may refer to the original cell line described in U.S. Pat. No. 7,745,140. However, for the purposes of the present process generally an anti-CD3 antibody will not usually be loaded onto the FcY receptor on the surface thereof. Preferably the aK562 cell as referred to herein is a derivative of the original aK562 cell line comprising at least one, such as one, two, three or four co-stimulatory factors on the surface thereof, in particular independently selected from the group comprising an anti-CD28 antibody, an anti-CD80 antibody, an anti-CD86 antibody and 4-1BBL.

One or more co-factors may have a role to play in reducing apoptosis of T cells and inducing a proliferative cycle of, for example about 7 to 10 cell divisions.

The cell is engineered to express co-stimulatory factors on its surface that provide signals that are important in the stimulation (activation or differentiation) or survival of T cells and complement the signal generated by the presentation of antigens on the surface of antigen presenting cells. Examples of the molecules that may be expressed on the cell line surface selected from the group comprising CD80, CD86, CD83, 4-1BB-ligand, and a combination thereof, for example 1, 2, 3, or 4 thereof. The four elements together provide a powerful co-stimulatory signal.

In one embodiment the aK562 cell further expresses OX-40 ligand on its surface.

These cells act together with the T-APCs, described above, to provide all the signals necessary for T cell activation.

CD80 and CD86 bind CD28, a surface glycoprotein present on about 80% of peripheral T cells in humans. In combination with the activation of the T cell receptor, this binding provides potent stimulation of T cells. What is more CD28 (on T cells) binding to its ligand in conjunction with T cell receptor engagement induces the production of IL-2.

In one embodiment the culture in step b) comprises only endogenous IL-2.

Alternatively the artificial co-stimulatory factory may be agonistic antibody for a relevant receptor such as antibodies that target for example CD28. These antibodies may be provided directly into the media, or attached to beads, or may be attached to the surface of the cell line (such as aK562). This is described in detail in US 2003/0147869, incorporated herein by reference.

Providing the co-factors on beads does not lead to the most efficient antigen specific expansion possible. Thus in one embodiment the co-factors are expressed on or associated with a cell such as aK562 cell.

This artificial co-stimulatory cell employed in step b) of the present invention (such as the aK562) cell seems to be acting by a new and surprising mechanism. The process of the present disclosure is evidence for the first time that antigen presentation can be provided on one cell and the co-stimulation can be provided by a different cell to stimulate and activate T cells. In the context of generating antigen specific T cells this is very surprising because in practice in the past generally aK562 cells have been engineered to express HLA molecules or an antibody that targets the T cell receptor and model the in vivo systems where the T cell receptor mediated signal and the co-stimulatory signal is provided by one cell (i.e. the contact is between two cells and for example CD28 ligation on T cells in conjunction with TCR engagement induces the production of IL-2 which triggers continued proliferation; June et al 1994, Jenkins et al 1993 and Schwartz 1992). Thus certain aK562 cell lines have been established which express MHC class 1 A2 and A3Britten, C. M.; Meyer, R. G.; Kreer, T.; Drexler, I.; Wolfel, T.; Herr, W. (2002), "The use of HLA-A*0201-transfected aK562 as standard antigen-presenting cells for CD8(+) T lymphocytes in IFN-gamma ELISPOT assays", *Journal of Immunological Methods* 259 (1-2): 95-110, and Clark, R. E.; Dodi, I. A.; Hill, S. C.; Lill, J. R.; Aubert, G.; Macintyre, A. R.; Rojas, J.; Bourdon, A. et al. (2001), "Direct evidence that leukemic cells present HLA-associated immunogenic peptides derived from the BCR-ABL b3a2 fusion protein", *Blood* 98 (10): 2887-93. Thus in certain embodiments the co-stimulatory cell such the aK562 cell is effectively an autonomous co-stimulatory factor (Third Party Co-stimulatory factor) which together with the T-APCs stimulates the antigen specific expansion of the target T cell population. Whilst in theory a aK562 cell that expresses the Fc receptor and that can be loaded with anti-CD3 antibody (such OKT3 antibody), to provide an antigen independent activation signal, may be employed in the present processes in at least one embodiment the aK562 (or engineered cell) is not loaded with an anti-CD3 antibody because generally the non-specific signal is not desirable. The present disclosure also extends to the use of an engineered cells line, such as aK562 cell, for providing an artificial co-stimulatory signal independent of antigen presentation in the expansion of T cells, such as autologous T cells.

Thus in one embodiment the process is characterised further in that the process of expanding the population of cells in step b) is surprising in the context of relying upon only (1) T-APCs (2) peptides to pulse/load the latter and (3) aK562 cells transduced to express only co-stimulatory molecules without antigen-specific presentation qualities. This process as described achieves expansion on an antigen-specific basis (as measured by an increasing percentage of antigen-specific T cells during the expansion process) despite the fact that the aK562 cells have not been engineered to present specific antigens. Without the addition of other APCs in this step (e.g. DCs), the expansion process is therefore relying upon T-APCs to achieve the first signal activation with respect to presentation of the target antigen. This is unusual since T-APCs are considered sub-optimal with respect to both antigen presentation and co-stimulation. The role of aK562 cells to provide co-stimulation and to enhance expansion has been described before, but the previous demonstration showed general CD3+ T cell expansion at the cost of reduced antigen specificity since the aK562 cell were not engineered to present specific antigens. In the present invention, the antigen-specificity is increased with expansion which indicates that the first signal antigen recognition step is being achieved by the T-APC which is acting synergistically with the second signal co-stimulation from the aK562 cell. This bifurcation of the antigen presentation and co-stimulation signals contravenes the currently embraced paradigm for antigen-specific T cell expansion wherein the first signal and second signal are delivered from the same APC.

In one embodiment the invention provides a method of stimulating and activating antigen specific T cell expansion employing antigen presentation on a first cell (or population of cells) and an artificial co-stimulatory factor which is a second distinct cell.

In one embodiment the engineered cell line, such as the aK562 cell line is irradiated before use in the method of the present disclosure, for example with a gamma radiation source of an X-ray source. The engineered cell line, such as the aK562 cell line may be provided in a frozen form in which case irradiation of the cells may be performed after freezing.

In one embodiment the ratio of CTLs to co-stimulatory factor (for example where the co-factor is a cell line) is in the ratio of 2:1 to 1:10 respectively, such as 1:5.

Suitable ratios of CTLs:antibody:co-stimulatory cells are in the range 1:1:0.2 to 1:1:10, such as 1:1:5. Advantageously, the method employing T-APCs and artificial co-stimulatory factors, such as engineered cells, may provide for improved levels of antigen specific T cell expansion in comparison to prior art methods.

The cytokine or cytokines employed in step a) and optionally step b) must be appropriate for stimulating and/or activating T cell growth or differentiation or perform some other useful function such as promotes T cell survival or the like.

Cytokines that may be employed in the process of the current disclosure include IL-1, IL-2, IL-4, IL-6 IL-7, IL-12 and IL-15.

In one embodiment the cytokines employed in the process according to the present disclosure are independently selected from IL-4, IL-7 and IL-15, such as a combination thereof.

In one embodiment in step a) the cytokines employed are IL-4 and/or IL-7. Whilst not wishing to be bound by theory the inventors believe that these cytokines have a role to play in regards to frequency, repertoire and expansion of viral antigen specific cells.

In one embodiment if IL-2 is employed in step a) then it is added at about day 3 or 4 of the culture and not at the outset.

The repertoire of T cells may be determined by ELISPOT analysis after stimulation with peptide libraries aliquotted into pools such that each peptide is uniquely represented in two pools (Kern, F., N. Faulhaber, C. Frommel, E. Khatamzas, S. Prosch, C. Schonemann, I. Kretzschmar, R. Volkmer-Engert, H. D. Volk, and P. Reinke. 2000. Analysis of CD8 T cell reactivity to cytomegalovirus using protein-spanning pools of overlapping pentadecapeptides. Eur J Immunol. 30:1676-1682 and Straathof, K. C., A. M. Leen, E. L. Buza, G. Taylor, M. H. Huls, H. E. Heslop, C. M. Rooney, and C. M. Bollard. 2005. Characterization of latent membrane protein 2 specificity in CTL lines from patients with EBV-positive nasopharyngeal carcinoma and lymphoma. J. Immunol. 175:4137-4147).

In one embodiment in step b) the cytokine employed is IL-15. Whilst not wishing to be bound by theory it is believed by the inventors that the IL-15 has a pro-survival effect on the relevant T cell population. In one embodiment the cytokine employed in step b) is IL-15.

Cytokines such as IL-15 may be replaced during culture e.g. twice weekly.

In one embodiment only the particular cytokines described in any one of the embodiments herein are employed.

IL-12 has a role in ThI focusing and exogenous IL-12 may be omitted if a balanced Th1/Th2 is desired. In one embodiment the process of the present disclosure does not employ exogenous IL-12. However, in the context of the present T cell product a ThI response in the CD4+ population is thought to be desirable.

The exogenous cytokines may be added at any stage of the process as appropriate, including concomitant addition when the cells are transferred into the culture system or at the start of the given step. The latter applies to step a) and/or step b).

The presence of exogenous cytokines in step a) and/or step b) may alternatively be added part way through the step, for example 1, 2 3, 4 days or more after the step is initiated.

In one embodiment the process of the present disclosure is employed to provide cell population comprising a CD4+ T cell population, for example a Th1 population. A Thi population as employed herein is intended to refer to a CD4+ population wherein 5% of the cells or more, such as 10, 20, 30, 40, 50, 60, 70, 80, 90% or more are classified as Th1.

Th1 cells, amongst other functions, generally maximize the killing efficacy of macrophages and the proliferation of cytotoxic CD8+ cells.

Memory T cells are a sub-category of Th1 cells.

In one embodiment the population of cells obtained from the process comprise a sub-population of memory T cells. Whilst not wishing to be bound by theory we believe that a substantial portion of the T cells obtained from the process will be derived from the memory portion of the starting population.

In one embodiment IL-2 is not employed in step (a) because the expansion promoted by this cytokine may be too non-specific and produce expansion of NK cells, T cells of unwanted function/specificity and T regulatory cells that may produce a certain amount of anergy in the cells. Thus in one embodiment the only IL-2 present in the culture is endogenous IL-2, i.e. it is secreted by the cells.

In one embodiment IL-2 is not employed in step (b) because it may promote a more differentiated phenotype than IL-15

Anergy as employed herein is intended to refer to a lack of responsiveness of the cells to antigen stimulation. Anergy can be measured using a functional assay, for example interferon gamma secretion by the relevant cell population. A lower level of interferon gamma secretion in comparison to full functional (non-anergic) cells may be indicative of a degree of anergy. Of course the greater the degree of anergy in the cells the lower the particular (marker) functionality will be.

As descried above anergy in the context of the expanded product is intended to be a generic term that refers to reduced cell function in one or more relevant ways. The term includes cell exhaustion, for example where the cells are no longer able to divide. The cell is then referred to as senescent. Cells stop dividing because the telomeres, protective bits of DNA on the end of a chromosome required for replication, shorten with each copy, eventually being consumed.

It is thought that that PD-1 (programmed cell death protein 1; Uniprot Q15116) which is expressed on the surface of cells, is a marker of anergy. In one embodiment less than 10%, for example 9, 8, 7, 6, 5, 4, 3, 2, 1, 0.5% or less of the relevant expanded T cell population express PD-1, such as about 1%. In patients with high levels of anergy in the T cells such as patient's with relapsed NPC the frequency of LMP/EBNAI-specific T cells may be increased in the presence of blocking antibodies to PD-L1 or PD-1, i.e. which block signaling from the ligand binding to the receptor.

This phenomenon was not found in healthy donors, suggesting that type 2 latency antigen specific T cells might be anergic in NPC patients.

Target antigen as employed herein is intended to refer to the antigen which is employed to generate specificity in the T cells to the therapeutic target, such as a particular virus, for example EBV. Thus the cells infected by target virus or cancer cells will usually express the target antigen and hence will themselves become a target for clearance by the immune system.

In one embodiment the population of T cells expanded are a balance CD4+ and CD8+ population, that is to say the cell population comprises both CD4+ and CD8+ cells but not necessarily in equal amounts. Balanced in the context of the present specification is employed to infer that one of the populations CD4+ or CD8+ is not depleted during expansion.

The cell populations expanded using the process of the present disclosure comprises the desired T cell population and generally will not consist only of the desired population. The final product administered to the patient may include a number of other cells that the process did not target the expansion of. In one embodiment the desired population of CD4+ and CD8+ cells comprises about 60% or less of the total population of cells. Frequency of the cell populations may be measured employing a gamma-IFN ELISPOT assay or employing Multimer (e.g. Tetramer) staining both of which are known to persons skilled in the art.

In one embodiment the T cells population obtained from the process are diverse when analyzed by spectratyping, but without the emergence of dominant clone. That is to say the T cell diversity in the starting sample is substantially represented in the expanded T cells, i.e. the expansion is not generally providing a monoclonal or oligo clonal target cell population.

A significant proportion for example 30% to 60% of the expanded cells will generally express effector memory markers including CD27, CD28, CD62L and/or CD45RO.

It is expected that 50% or more, such as, 60, 70, 80, 90 or 95% of the antigen specific T cells according to the present disclosure may be capable of killing target cells expressing antigens that were used in the expansion process.

We believe sufficient cells even for the highest cell doses required for the treatment of patients can be prepared employing two stimulations employing methods of the present disclosure taking in the range of 16 to 24 days of T cell culture compared to 28 to 63 days of LMP-T cell culture using Ad vectors and LCLs.

What is more the cells produced by the process of the present invention may be advantageous in that there are more specific, produce higher levels of gamma interferon and/or express lower levels of anergy markers compared to cells prepared by the prior art processes.

In one embodiment, anergic T cells from cancer patients may grow poorly and require three stimulations. The third stimulation might include additional stimulatory components. Since at this time the majority of cells should be specific, there is not a concern about expansion of unwanted cells. In one embodiment the third stimulation culture will comprise (1) peptide-pulsed, irradiated autologous activated T cells, (2) irradiated costimulatory cell line such as aK562 cells, (3) irradiated PBMCs from blood bank approved allogeneic donors and (4) submitogenic doses of anti-CD3; 1 to 100 ng per mL for example 50 ng per ml.

In one embodiment one or more tests are performed to establish the suitability of the cells for use in therapy, for example an interferon gamma ICS (intracellular cytokine staining) and/or an interferon gamma ELISPOT assay.

In one embodiment the suitability testing is combined in a single flow cytometry assay.

In one embodiment a $^{51}Cr$ release assay for non-specific killing is performed, but this will generally not form part of the suitability assays.

In one embodiment batch release testing is set out in Table 1:

| TEST | Specification |
|---|---|
| 1. Viability Dye exclusion or flow cytometry | >70% Viable |
| 2. Purity Flow cytometry | >80% CD3+ |
| 3. Safety | |
| 3.1 Endotoxin (LAL assay) | ≤5.0 EU/ml |
| 3.2 Bacterial sterility | |
| Aerobic Bacteria - Bactec | Negative |
| Anaerobic Bacteria - Bactec | Negative |
| Fungal contaminants - Bactec | Negative |
| 3.3 *Mycoplasma* PCR Assay | Negative |
| 3.4 Non-specific killing* | <10% killing target cells at 20:1 E:T ratio |
| 4. Identity | HLA class I antigen identical with patient/donor |
| 5. Potency | |
| 5.1 IFN- γ + cells | >3 standard deviations greater response to stimulation with specific peptides than to control stimulation |
| 6. Dosing | |
| CD3+ number | 1-10 × $10^7$ cells per $m^2$ or 2-20 × $10^5$ per kg BW |

The process of the present disclosure may be performed in a well or containers but most suitably is performed in a gas-permeable system. Vessel as employed herein is intended to refer to any type of container suitable for retaining the cells, media etc., for example a bag, such as an infusion type bag (provided with a gas permeable portion) or a rigid vessel, such as the GRex™ system. The gas permeable layer facilitates rapid expansion of cells and minimizes the number of media changes required.

In one embodiment step a) is performed in a GRex™ 10 system. The GRex™ 10 system is suitable for culturing up to 1×$10^5$ T cells.

In one embodiment step b) is performed in a GRex™ 100 system.

WO 2005/035728 incorporated herein by reference describes how to prepare a gas permeable vessel. In one embodiment silicone gas permeable material is employed.

In one embodiment the system employed is a GRex™ system from Wilson Woolf. In one embodiment the system is adapted to provide aseptic preparation as described in U.S. provisional application Ser. No. 61/550,246 incorporated herein by reference.

Generally the system is seeded with about 0.5 million cells per $cm^2$ of surface area. In a GRex-10 with a surface area of 10 $cm^2$, a minimum of 5 million and up to 20 million cells would be seeded.

In one embodiment in step (a) 20 million cells might be seeded in a GRex-10. Within PBMC, less than 1% of cells are specific for the peptides, so at most 0.2 million specific cells are seeded. The remaining PBMCs act as feeder cells.

In one embodiment in step (b) 50 million irradiated a K562 cells plus 10 million peptide-pulsed activated and irradiated T cells and 10 million effector T cells would be seeded into a GRex-100 (100 $cm^2$), In this case only the effector T cells will proliferate.

In one embodiment the present disclosure extends to the cell composition obtained directly from the process.

In one embodiment the process according to the present disclosure generates sufficient CD3+ cells to provide at least two individual doses for a patient.

The invention also extends to compositions with the same desirable characteristics of the cell populations prepared by the methods disclosed herein.

Thus in one aspect the present disclosure provides an autologous T cell population expanded in vitro to contain a population of T cells specific to a target antigen, such as a virus, wherein the population is substantially free of target virus contamination and responses to viral vectors.

The present process also relates to the preparation of dendritic cells pulsed with peptide mixes and the cell populations obtained therefrom, for use in the expansion of antigen specific T cell populations, particularly as described herein.

The present process also relates to the process of preparing T-APCs pulsed with peptide mixes and the cell populations obtained therefrom.

The present disclosure also relates to autologous T cell populations described herein, for example comprising a population of CD4+ and CD8+ antigen specific T cells, wherein the antigen is associated with virus infected cells or cancer cells.

In one or more embodiments the cell populations according to the present disclosure have one or more advantageous properties in comparison to cells prepared by the prior art method.

In one embodiment the average cell diameter of cells in the relevant T cell population is 10 to 14 μM. Advantageously the cells cultures of the present invention produce generally low toxicity after infusion, for example are associated with few toxicity intolerance responses, for example inflammatory responses, cell damage, flu like symptom, nausea, hair loss or the like.

The cell populations according to the present disclosure also provide advantageous properties, for example high levels of interferon gamma expression.

High levels of interferon gamma expression as employed herein is intended to refer to the fact that on average cell populations prepared by the current method may express higher levels of interferon gamma than cells prepared by prior art methods and certainly express higher levels of interferon gamma than the original anergic cells obtained from the patient.

In one embodiment the cells of the present disclosure show enhanced antigen specificity, for example in an assay disclosed herein, for example the cells of the present disclosure contain a higher frequency of cells that secrete cytokines in response to stimulation with the antigens in comparison to cells prepared by a prior art method. This figure will usually be a mean which is a per cell value derived from the values obtained for the population and divided by the number of cells present.

In one embodiment the cell populations of the present disclosure show comparable avidity (not significantly different) to cell populations prepared by a prior art method.

To determine avidity, autologous activated T cells may be pulsed with dilutions of peptide, labelled with $^{51}$chromium and used as targets in a standard cytotoxicity assay. The most avid T cells are those that kill target cells pulsed with the lowest concentration of peptide. Alternatively IFN gamma production can be measures using an ELISPOT assay with dilutions of peptide.

In one embodiment the cell populations of the present disclosure show increased ability to kill target cells in comparison to cell populations prepared by a prior art method.

In one embodiment the T cell populations provided by the present disclosure are effective in expanding in vivo to provide an appropriate immune response to cells infected by a target virus and/or cancer cells associated with a target virus.

The present invention also extends to compositions comprising the autologous T cell populations according to the invention. These compositions may comprise a diluent, carrier, stabilizer, surfactant, pH adjustment or any other pharmaceutically acceptable excipient added to the cell population after the main process steps. An excipient will generally have a function of stabilizing the formulation, prolonging half-life, rendering the composition more compatible with the in vivo system of the patient or the like.

In one embodiment a protein stabilizing agent is added to the cell culture after manufacturing, for example albumin, in particular human serum album, which may act as a stabilizing agent. The amounts albumin employed in the formulation may be 10 to 50% w/w, such as about 12.5%. w/w.

In one embodiment the formulation also contains a cryopreservative, such as DMSO. The quantity of DMSO is generally 20% or less such as about 12% in particular 10% w/w.

In embodiment the process of the present invention comprises the further step of preparing a pharmaceutical formulation by adding a pharmaceutically acceptable excipient, in particular an excipient as described herein, for example diluent, stabilizer and/or preservative.

Excipient as employed herein is a generic term to cover all ingredients added to the T cell population that do not have a biological or physiological function.

Once the final formulation has been prepared it will be filled into a suitable container, for example an infusion bag or cryovial.

In one embodiment the process according to the present disclosure comprises the further step of filling the T cell population or pharmaceutical formulation thereof into a suitable container, such as an infusion bag and sealing the same.

In one embodiment the container filled with the T cell population of the present disclosure or a pharmaceutical composition comprising the same is frozen for storage and transport, for example is store at about −135° C., for example in the vapor phase of liquid nitrogen.

In one embodiment the process of the present disclosure comprises the further step of freezing the T cell population of the present disclosure or a pharmaceutical composition comprising the same. In one embodiment the "product" is frozen by a controlled rate freezing process, for example reducing the temperature by 1° C. per minute to ensure the crystals formed are small and do not disrupt the cell structure. This process may be continued until the sample has reached about −100° C.

A product according to the present disclosure is intended to refer to a cultured cell population of the present disclosure or a pharmaceutical composition comprising the same.

In one embodiment the product is transferred, shipped, transported in a frozen form to the patient's location.

In one embodiment the product according to the present disclosure is provided in a form suitable for parenteral administration, for example infusion, slow injection or bolus injection. In one embodiment the formulation is provided in a form suitable for intravenous infusion.

In one aspect the present disclosure provides a method of transporting a product according to the present disclosure, from the place of manufacture, or a convenient collection point to the vicinity of the intended patient, for example where the T cell product is stored below 0° C., such as −135° C. during transit.

In one embodiment the temperature fluctuations of the T cell product are monitored during storage and/or transport.

In one embodiment there is provided a product of the present disclosure for use in treatment, for example in the treatment of a viral associated disease or malignancy, such as EBV infection, CMV infection, adenovirus infection, HIV infection, hepatitis C or B infection, parvovirus infection, influenza virus infection, or a cancer from viral origin, for example EBV-associated lymphoma or carcinoma, HHV8-associated sarcoma, papillomavirus-associated carcinoma or SV40-associated cancers.

Other viral morbidities include varicella zoster virus infection, vaccinia virus infection and complications of either of the same.

In one embodiment the treatment is of an immunosuppressed patient.

In one embodiment, the patient is not immune-compromised.

In one embodiment there is a provided a method of treating a patient with a product according to the present disclosure comprising the step of administering a therapeutically effective amount of product defined herein.

Therapeutically effective amount, does not necessarily mean an amount that is immediately therapeutically effective but includes a dose which is capable for expansion in vivo (after administration) to provide a therapeutic effect.

Thus there is provided a method of administering to a patient a therapeutically effective amount which is a subtherapeutic dose of expanded T cells which are capable for expansion in vivo to provide the desired therapeutic effect, for example.

In one embodiment the antigen specific T cell population produced is specific to EBV virus and prevents, ameliorates or eliminates cells infected with EBV and/or clinical pathologies associated therewith, for example EBV associated cancers.

Symptoms of infection include fever, sore throat, and swollen lymph glands. Sometimes, a swollen spleen or liver involvement may develop. Heart problems or involvement of the central nervous system occurs only rarely. EBV remains dormant or latent in a few cells in blood for the rest of the person's life and can be reactivated, for example in immunosuppressed patients when immune controls are reduced or absent. Whilst the infection is not fatal in individuals with a healthy immune system, the infection can lead to severe complications and death in immunosuppressed patients.

EBV is best known as the cause of infectious mononucleosis. It is also associated with particular forms of cancer, particularly Hodgkin's lymphoma, non-Hodgkin's lymphoma, Burkitt's lymphoma, nasopharyngeal carcinoma, gastric carcinoma and central nervous system lymphomas associated with HIV. Finally, there is evidence that infection with the virus is associated with a higher risk of certain autoimmune diseases, especially dermatomyositis, systemic lupus erythematosus, rheumatoid arthritis, Sjögren's syndrome, and multiple sclerosis.

In one embodiment the target patient population for treatment has nasopharyngeal carcinoma. In one embodiment the target patient population for treatment has gastric carcinoma.

Thus T cell populations specific to EBV according to the present disclosure can be employed in the treatment of prophylaxis of one or more of the above conditions.

In one embodiment there is provided a method of treatment or prophylaxis of a varicella zoster virus infection and/or complications associated therewith, including encephalitis, pneumonia, posthereptic neuralgia, shingles, zoster multiplex, myelitis, herpes opthalmicus and zoster sine herpete, comprising administering a therapeutically effective amount of a T cell population comprising T cells specific to VZV, according to the present disclosure.

In one embodiment there is provided a method of treatment or prophylaxis of a vaccinia virus infection and/or complications associated therewith.

In one embodiment a dose of at least $1\times10^7$ cells per m$^2$ or $2\times10^5$ per kg is employed.

In one embodiment a first dose of about $2\times10^7$ per m$^2$ and a second dose of $2\times10^7$ or $1\times10^8$ T cells per m$^2$ is employed.

In one embodiment the present disclosure provides use of a peptide mix covering a viral or cancer antigen(s) for generating autologous dendritic cells suitable for use in expansion of autologous antigen specific T cells.

In one embodiment the present disclosure provides use of a peptide mix covering a viral or cancer antigen(s) for generating autologous T-APCs suitable for use in the expansion of antigen specific T cells. In one embodiment the present disclosure provides use of aK562 cells or other artificial co-stimulatory factory for use as a co-stimulatory factor without concomitantly presenting antigen thereon in the expansion of antigen specific T cells (in particular autologous T cell expansion), for example employed in conjunction with T-APCs for expansion of antigen specific T cells, in particular antigen specific T cells, such as autologous antigen specific T cells.

In one embodiment there is provided a kit comprising a peptide mix covering a viral or cancer antigen(s) and an artificial co-stimulatory factor such as an aK562 cell, in particular for use in T cell expansion, such as autologous antigen specific T cell expansion. In one embodiment the kit further comprises IL-15.

In one embodiment the kit comprising a peptide mix covering a viral or cancer antigen(s) and IL-4 and IL-7 for use the expansion of antigen specific T cells, for example autologous antigen specific T cells.

PROTOCOLS AND EXAMPLES

Abbreviations

APCs Antigen presenting cells
ATC Activated T cell
CTLs Cytolytic T lymphocytes
DCs dendritic cells
EBV Epstein-Barr Virus (a virus from the Herpes family of viruses)
LCL lymphoblastoid cell line
EBV-LCL lymphoblastoid cell line infected with EBV
LMP1 Latent Membrane Protein 1 Uniprot number P03230
LMP2 Latent Membrane Protein 2 Uniprot number Q1HVJ2
BARF1 protein encoded by the BamHI rightward reading frame uniprot number
EBNA1 EBV nuclear antigen 1 Uniprot number P03211
PBMC peripheral blood mononuclear cell
CMV Cytomegalovirus Protocol 1: Processing of Sample to Obtain PBMCs The steps below should be performed in a certified biological safety cabinet, using aseptic techniques and following universal precautions.

A blood sample or an apheresis sample or a buffy coat sample (which is the fraction of an anti-coagulated blood sample after density gradient centrifugation that contains most of the white blood cells and platelets) is diluted with an equal volume of Dulbecco's Phosphate Buffered Saline or RPMI medium (for example RPMI 1640 available from Life Technologies), at ambient (room) temperature.

In a 50 ml centrifuge tube, 15 ml Lympho-prep is carefully overlaid with approximately 30 ml of diluted blood. This step can be adjusted to utilize all the available cells.

The material is centrifuged at 400×G for about 40 minutes at ambient temperature.

Aliquots, for example 3×1 ml plasma aliquots may be stored at −80° C.

The PBMCs interface is harvested into an equal volume of Dulbecco's Phosphate Buffered Saline or RPMI medium (for example RPMI 1640 available from Life Technologies). Centrifuge at about 450×G for about 10 minutes at room temperature and then aspirate supernatant. The pellet obtained should be loosened and re-suspended in about 20 ml Dulbecco's Phosphate Buffered Saline or RPMI medium (for example RPMI 1640 available from Life Technologies).

If the process is performed multiple times then the cells may be combined in a single centrifuge tube and thoroughly re-suspended. The cells will generally be counted by removing 20 µl of cells and adding 20 µl of 50% red cell lysis buffer and counted using a hemacytometer in accordance with the manufactures instructions.

The PBMCs may be used in the expansion antigen specific T cells, expansion of CD3 and CD28 activated T cells and in the preparation of dendritic cells.

NOTES: Since the PBMCs cells prepared are ultimately intended for infusion into patients it is essential to adhere to procedures for the identification and handling of patient samples. Only one patient's sample should be handled at a time. Generally the number of PBMCs recovered will be in the range 0.5 to $2.0\times10^6$ PBMCs per ml of blood. Up to $1\times10^9$ may be recovered from a buffy coat.

REFERENCES

Sili U et al Large-scale expansion of dendritic cell-primed polyclonal human cytotoxic T-lymphocyte lines using lymphoblastoid cells for adoptive immunotherapy. J. Immuother. 2003 May-June: 26(3): 241-56

Leen A M et al Contact-activated monocytes: efficient antigen presenting cells for the stimulation of antigen-specific T cells. J Immunother. 2007 January: 30(1): 96-107.

Bollard C M et al The generation and characterization of LMP2-specific CTL for use as adoptive transfer from patients with relapsed EBV-positive Hodgkin disease J. Immunother.

Protocol 2: Generation of Dendritic Cells

Dendritic cells can be differentiated from adherent of CD14-selected PB mononuclear cells (PBMC) by culture in GM-CSF and IL-4. The dendritic cells can then be matured using GM-CSF, IL-4, IL-1β, IL-6, TNF-α and PGE-1 or PGE-2 (PGE=Prostaglandin E). The dendritic cells loaded with peptides can present the peptides on HLA class I and class II molecules to antigen-specific T cells via the TCR.

Preparation of Adherent PBMCs—Dilute heparinized peripheral blood, for example 30 ml, in an equal volume of Dulbecco's Phosphate Buffered Saline or RPMI medium (for example RPMI 1640 available from Life Technologies), at ambient (room) temperature.

Alternatively thaw previously frozen PBMC, wash twice in CellGenix DC medium, and count the cells.

In a 50 ml centrifuge tube, 15 ml Lymphoprep is carefully overlayed with approximately 30 ml of diluted blood. This step can be adjusted to utilize all the available cells.

The material is centrifuged at 400×G for about 40 minutes at ambient temperature.

The PBMCs interface is harvested into an equal volume of Dulbecco's Phosphate Buffered Saline or RPMI medium (for example RPMI 1640 available from Life Technologies). Centrifuge at about 450×G for about 10 minutes at room temperature and then aspirate supernatant. The pellet obtained should be loosened and re-suspended in about 20 ml Dulbecco's Phosphate Buffered Solution.

The above steps are the same as Example and then the material is then centrifuged at 400×G for about 5 minutes at room temperature. The supernatant is then removed and the pellet is re-suspended in 20 ml of DC medium.

Count cells as defined in Example 1. If the concentration is greater than $5 \times 10^6$ per ml adjust to $5 \times 10^6$ per ml by adding CellGenix DC medium. If the concentration is less than $5 \times 10^6$ per ml the pellet and re-suspend at $5 \times 10^6$ per ml in CellGenix DC medium.

Transfer 10 ml of cells per 75 cm$^2$ flask or 2 ml of cells/well of a 6 well plate.

Transfer to 37° C. and 5% carbon dioxide for about 2 hours. Rinsing the flask three times 10 mls of Dulbecco's Phosphate Buffered Saline or RPMI medium combining the supernatants contain thing the PBMC non-adherent fraction.

For a T-75 culture flask (available from Falcon) add 10 ml of DC culture medium containing 1000 units per ml of IL-4 and 800 units per ml of GM-CSF to the adherent cells.

For a 6-well plate add 2 mls of DC culture medium containing 1000 units per ml of IL-4 and 800 units per ml of GM-CSF to the adherent cells.

Transfer the flasks or plated to an incubator at 37° C. and 5% carbon dioxide.

If not previously cryopreserved, non-adherent cells may be cryopreserved for future use in the preparation of responder T cells.

On day 3 or 4 add 1000 units per ml of IL-4 and 800 units per ml of GM-CSF.

A summary of the cytokines added are provided in Table 1:

| Cytokine | Final Concentration | Stock | Volume to be Added per ml |
|---|---|---|---|
| GM-CSF | 800 U/ml | 2,800 U/ml | 3.8 μl |
| IL-4 | 1000 U/ml | 4000/μl | 33 μl |
| TNF-α | 10 ng/ml | 1μl/ml Dilute 1:100 (10 ng/ml) | 13 μl Diluted solution |
| PGE-1 | 1 μg/ml | 0.5 g/ml | 2.7 μl |
| IL-1β | 10 ng/ml | 10 ng/μl | 10 μl |
| IL-6 | 100 ng/ml | 10 ng/μl | 10 μl |

The culture is then incubated for about 2 days at 37° C. and 5% carbon dioxide after which the dendritic cells are ready of preparation as stimulators for autologous PBMC.

The dendritic cells are harvested and counted. Note that cells are lost when washed several times, therefore the wash steps can be omitted when dendritic cell numbers are limiting. Dendritic cells do not divide and the omission of irradiation is not important.

If greater than $5 \times 10^5$ transduced dendritic cells are recovered send approximately $10^5$ for phenotyping along with non-transduced dendritic cells if the latter are available.

If less than $5 \times 10^5$ transduced dendritic cells are recovered then proceed to peptide loading.

The supernatant is aspirated after centrifugation and the 5 μl (5 ng) of each peptide library (i.e. for each antigen) per $1 \times 10^6$ dendritic cells is added. The mixture is then incubated for 30 to 60 minutes in 5% carbon dioxide incubator and then irradiated at 30 Grays.

The cells are re-suspended in 20 mls of medium and centrifuged for about 5 minutes at 400×G. Re-suspend the cells at $10^5$ per ml with CTL culture medium. The dendritic cells are now ready for use as stimulators for PBMCs.

As with Example 1 because these cells are to be infused into patients appropriate procedures must be followed.

Recovery of total dendritic cells should be 1 to 8% of the starting population.

REFERENCES

Gahn B et al Adenoviral Gene Transfer into Dendritic Cells Efficiently Amplifies the Immune Response to the LMP2A-Antigen; a potential treatment strategy for EBV virus-positive Hodgkin's lymphoma. Int. J. Cancer 2001 Sep. 1; 93(5): 706-13

Bollard C M et al The generation and characterization of LMP2-specific CTLs for use in adoptive transfer from patients with relapsed EBV-positive Hodgkin disease J. Immunother (1997). 2004 July-August; 27(4):317-327

Gottschalk S et al Generating CTLs against subdominant Epstein-Barr virus LMP1 antigen for the Blood 2003 Mar. 1; 101(5): 1905-12.

Protocol 3: Generation of T-APCs
1. Coat non tissue culture treated 24 well plates or T-75 non tissue culture treated flasks with CD3 and CD28 antibodies (Miltenyi)
1.1. Calculate the number of wells/flasks to be coated based on the PBMC number to be plated at 1×106 cells per well or 30-50×106 cells per T-75 flask
1.2. For wells, plate 0.5 ml of H$_2$O containing 1 ng CD3 (5 μl/ml of H$_2$O of 0.2 mg/ml stock) and 1 g CD28 (2 L/ml of H$_2$O of 0.5 mg/ml stock) per well.
1.3. For T-75 flasks, after prewashing with 18 ml of H$_2$O; use 90 C51 CD3 (stock 0.2 mg/ml) and 36 μl CD28 (stock 0.5 mg/ml) in 18 mls H$_2$O per flask.
1.4. Incubate for at least 3 hours in 37° C. incubator.
1.5. Optional: CD3-CD28 coated plate can be incubated overnight at 4° C.
2. Wash wells or flasks
2.1. Remove CD3/28 solution and rinse once with 1 mL of PBS or medium per well or 10 mls per T-75 flask
3. Re-suspend PBMCs at 2×10$^6$ in 30 mL of T cell medium (10% human AB serum, 45% RPMI 1640 (or advanced RPMI), 45% EHAA and 200 mM L-glutamine)
3.1. Aliquot 2 mls per CD3/28-coated well or 15 to 25 mls to a T-75 flask
3.2. Transfer to incubator for 2 days with flask lying flat.
4. On day 2 add 100 units per mL of IL-2.
5. On day 4 to 5 cells re-suspend cells and count.
6. Split cells according to the cell number obtained
6.1. 5×106 cells per GRex 10
6.2. 5×107 per GRex 100.
7. 3 to 4 days later, harvest cells and count
7.1. Either further expand as in step 4
7.2. Or cryopreserve 8. Cryopreservation
8.1. Centrifuge cells and aspirate supernatant
8.2. Flick pellet to re-suspend and transfer to ice for 10 to 30 minutes
8.3. Re-suspend at $5\times10^6$ to $10\times10^6$ cells per ml of ice cold cryopreservation medium (10% DMSO, 50% human AB serum, 40% RPMI 1640)
8.4. Transfer to cryocontainers (cryobags or cryovials)
8.5. Freeze in freezing containers at ~1° C. per minute for at least 90 minutes, then transfer to liquid nitrogen
9. Prior to use at antigen-presenting cells, T cells must be re-stimulated on CD3/28 antibody-coated plates as in step 3, for 2 to 4 days to upregulate co-stimulatory molecules
9.1. This step is critical as if T cells have a resting phenotype, they may induce T regulatory cells Protocol 4: Expansion of Autologous Antigen Specific T Cells Using a Preferred Embodiment of the Invention
1. Re-suspend PBMCs at $2\times10^6$ per mL of T cells medium containing IL-4 and IL-7.
T cell medium is 10% human AB serum, 45% Advanced RPMI, 45% EHAA and 200 mM L-glutamine. IL-4 is added at 20 ng per mL (10 ng/ml final dilution) and IL7 at 3332 units per mL (1666 U/ml final dilution)
2. Re-suspend peptide-coated dendritic cells at $1\times10^5$ to $2\times10^5$ per ml
3. Mix PBMCs and DCs at a 1:1 ratio
4. Transfer 20 mls per GRex-10 ($20\times10^6$ PBMCs) and add 10 mls additional medium containing IL-4 (1666 units per mL) and IL-7 (long per ml). Transfer to incubator for 7 days
5. On day 7 remove 20 mls medium
Re-suspend cells and count.
If >$50\times10^6$ cells, split between two GRex-10s. If <$50\times10^6$ leave in one GRex-10.
Add medium containing IL-4 and IL-7 to 30 mls in each GRex-10 (final concentration of IL-4 is 1666 units per mL and of IL-7 is 10 ng per ml)
Transfer to incubator for 2 to 3 more days
6. On Day 9 or 10 re-stimulate with peptide-coated T-APCs and aK562 cells
Harvest responder T cells from GRex and count
Re-suspend at $1\times10^6$ cells per ml
Transfer to Incubator
6.1 Prepare aK562-CS cells to provide a 5:1 aK562-CS to T cell ratio
6.1.1. Irradiate aK562-CS cells with 100 GY (Grays)
6.1.2. Centrifuge for 5 minutes and 400 G
6.1.3. Re-suspend in complete T cell medium
6.1.4. Count and estimate the number of aK562-CS cells required
6.1.4.1. The number of responder T cells×5
6.2. Prepare peptide-pulsed, irradiated, activated autologous T cells (T-APCs)
6.2.1. Autologous T cells (ATCs) should have been stimulated or re-stimulated with CD3/28 two to 4 days before use
6.2.2. Harvest sufficient number of ATCs for stimulation plus ~30% to account for loss during processing
6.2.3. Centrifuge cells at 400 G for 5 minutes and aspirate supernatant
6.2.4. Loosen cell pellet by finger-flicking
6.2.5. Add long of each peptide per $10\times10^6$ ATCs
6.2.6. Incubate at 37° C. in 5% $CO_2$ in air for 30 to 90 minutes
6.2.7. Re-suspend in ~20 mL medium
6.2.8. Irradiate 30 GY
6.2.9. Centrifuge 400 G for 5 minutes and aspirate supernatant
6.2.10. Re-suspend at $10^6$ cell per mL
6.3. Combine $1\times10^7$ responder T cells with $1\times10^7$ T-APCs and $5\times10^7$ irradiated aK562-CS cells per GRex-100
6.3.1. Add medium to 400 mL
6.3.2. Add 10 ng per mL IL-7 (2 mg) and $6.6\times10^6$ units of IL-4
6.3.3. Transfer to incubator for 3 to 4 days
7. Add IL-2 (50 to 100 units per mL) or IL-15 10 ng per mL
7.1. Return to culture for 3 to 4 days
7.2. Add cytokines every 3 to 4 days
8. Measure glucose from day 7
8.1. Remove 1 drop of medium and test on standard hand held glucometer
8.2. Glucose levels of less than 100 should trigger a change of medium/cytokines
8.3. Responder T cells should be cryopreserved when sufficient number have been obtained
9. A third stimulation (steps 7, 8 and 9) can be performed if insufficient cells are obtained Example 1: Generation of EBNA1, LMP1 & LMP2 Specific T Cells for Healthy Donors and Patients with Nasopharyngeal Carcinoma and Lymphoma Sub Experiment: Generation of EBNA1, LMP1 & LMP2 Specific T Cells for Lymphoma Patient 1.
D1 Coating OKT3/CD28 Plate
Prepared OKT3 and CD28 antibodies by adding 5 ug each of OKT3 and CD28 antibodies to 5 mL of sterile water. Added 0.5 mL of this mixture into each well of a non-tissue culture treated 24 well plate (24-w-p). Incubated at 4° C. overnight. Note: this is culture day (−)8.
D2 Generation of dendritic cells from frozen PBMCs by adherence & generation of OKT3 blasts from non-adherent PBMC population—culture day (−)7
Lymphoma patient 1 peripheral blood mononuclear cells (PBMCs) frozen stock taken out from GMP bank and follow up samples with permission of PI (Cath Bollard): 4 vials of PBMCs, all frozen between February and March 2010, 5 million each vial, total 20 million. PBMCs were thawed out in 2 vials of 40 mL warm CellGenix media and spun down. PBMC count of patient 1: 22.5 million Spun down patient 1 PBMCs and re-suspended in a total of 6 mL of warm CellGenix media, then plated PBMC out in 3 wells of a 24-w-p with 2 mL per well. After 3 hours the non-adherent portion was gently washed off with sterile PBS twice and media was replaced with CellGenix with IL4 and GM-CSF. Incubated at 37° C. The non-adherent portion was used to generate OKT3 blasts. OKT3 blast generation:
A plate with OKT3 and CD28 coated the day before and stored at 4° C. was washed once with 0.5 mL of T cell media per well. Non-adherent portion of PBMCs was plated out into ~10 wells. Incubated at 37° C.
D3 Fed OKT3 blasts with IL2 by replacing ½ of the media in the well with CTL Media with 100 units of IL2/mL to make final culture concentration of 50 units/mL
D4 Fed DCs with IL4 & GMP-CSF by replacing 1 mL of media per well with fresh media with IL4 & GMP-CSF
Moved OKT3 blasts into a new tissue culture treated 24-w-p. Incubated at 37° C.
D7 Transduced 1 well of each patient DC with Ad-LMP1-LMP2 by harvesting cells with scraping, counted, spun down then added Ad-LMP1-LMP2 at MOI of 5000.
Patient 1: 0.5 million DC, thus added 0.5 ul of virus at $5\times10^{12}$ vp/mL concentration Flicked tubes every ~15 minutes while incubating at 37[1*]° C. for 1.5 hrs. Resuspended cells back in media containing GM-CSF, IL4, IL1b, IL6, TNFa, and PGE2 and plated out back into 1 well each of a 24-2-p with 2 mL of media.

For the condition without Adenoviral vector, ½ media was taken off, and then CellGenix media with 2× of GMP-CSF, 1L4, IL1b, IL6, TNFa and PGE2 was added back into the wells. Incubated at 37° C.

Continued feeding OKT3 blasts by replacing media or splitting cells into extra well.

D9 D0 Setting up first stimulation.

Harvested and counted dendritic cells:

Patient 1: Non-transduced DCs: 0.2 million; transduced DC: 0.05 million

Removed a frozen vial of patient 1 PBMCs from GMP (cells frozen in 2009) to be stimulated, then thawed cells using warm CTL media with 30% FBS:

Patient 1: 1 vial of frozen PBMCs at 10 million per vial, recovered 8 million

Pulsing of DC and whole PBMCs with pepmixes:

Diluted EBNA1, LMP1 and LMP2 pepmixes by adding 1 ul of stock pepmix solution (in DMSO) each into 200 ul of sterile PBS.

Spun down all non-transduced DC from both donors and aspirated all but ~50 ul of media. Loosened pellets by flicking the tubes. Added ~10 ul of diluted pepmix to the pellets, incubated at 37[*]° C. for 30 min with occasional flicking.

3 million of PBMCs from donor 1 were taken to a new clean tube each, spun down, and all but ~50 ul of media aspirated. Added ~3 ul of diluted pepmix into the pellet. Incubated at 37[*]° C. for 30 min with occasional flicking.

Setting up T cell culture Day 0 for patient 1:

Current GMP condition: Spun down and re-suspended DCs into 0.5 mL of media after incubation; took out 1 million of PBMCs, spun down and re-suspended in 0.5 mL of complete CTL media (2 million per mL). Added both into a well of a 48-w-p. Added 5 ug of IL15 to make final concentration of 5 ng/ml. DC:PBMC ratio of this condition was 1:20. Incubated at 37° C. Condition DC(px): Washed DC pulsed with pepmixes with 20 mL of PBS. Re-suspended with 2 mL of complete CTL media, plated out 1 mL per well of a 24-w-p. Took out 4 million of PBMCs, spun down and re-suspended at 2 million per mL. Added 1L4 & IL7 at 2× concentration (20 ng/mL) to PBMCs. Added 1 mL into each well that already had DC to bring final concentration of IL4 and 117 down to 10 ng/mL. DC:PBMC ratio of this condition was 1:20. Incubated at 37° C.

Condition Px: Re-suspended PBMC pellet in 2 mL of complete CTL media, added ILA and 1L7 at 10 ng/mL, plated out into 1 well of a 24-w-p. Incubated at 37° C.

D10 Patient 1 OKT3 blasts expanded to 2 full 24-w-p. Count: 65 million. Frozen down in 4 vials with each vial at ~15 million cells.

D15 Coating OKT3/CD28 plate

Prepared OKT3 and CD28 antibodies by adding 5 ug each of OKT3 and CD28 antibodies to 5 mL of sterile water. Added 0.5 mL of this mixture into each well of a non-tissue culture treated 24 well plate (24-w-p). Incubated at 4° C. overnight.

D16 Transduced LCL with Ad-LMP1-LMP2

~3 million of LCL from donor 1 culture was taken out, spun down, then added 3 ul of virus at concentration of 5×10^12 vp/mL for MOI of 5000. Incubated at 37[*]° C. for 1.5 hr with interval flicking of tube. After incubation re-suspended cells in ~5 mL of complete RPMI. Incubated at 37° C.

Activated OKT3 blasts:

Thawed out a vial each of OKT3 blasts from donor 1 at 10 million per vial in warm CTL media with 30% FBS. Spun down cells and re-suspended in 20 mL of CTL media. Washed a plate of OKT3 & CD28 coated with CTL media, then plated cells out into 10 wells of a 24-w-p. Incubated at 37° C.

D18 Culture day 10

Harvested and counted day 10 T cells from patient 1:

Condition GMP: 2.13 million

Condition DC(px): 2.4 million

Condition Px: 3.04 million

Harvested patient 1 OKT3 blasts and irradiated at 30 Gy. Count: 13.4 million

Harvested aK562cs and irradiated at 100 Gy. Count: 4.4 million. Washed, spun down and re-suspended in 11 mL for a cell concentration of 0.4 million per mL Harvested patient 1 transduced LCL, irradiated at 40 Gy. Count: 5.7 million Because we didn't have enough cells for testing antigen specificity by ELISpot or phenotyping for lymphocyte subtypes, we only stimulated these cultures.

Second stimulation:

Pulsing of OKT3 blasts with pepmixes:

Diluted EBNA1, LM P1 and LMP2 pepmixes by adding 1 ul of stock pepmix solution (in DMSO) each into 200 ul of sterile PBS.

Spun down OKT3 blasts and aspirated all but ⁻50 ul of media. Loosened pellets by flicking the tubes. Added ⁻20 ul of diluted pepmix to the pellets, incubated at 37[*]° C. for 30 min with occasional flicking. Washed with 20 mL of PBS, spun down.

Re-suspended OKT3 blasts at concentration of 1 million per mL

Condition GMP:

Spun down LCL and re-suspended in 14.25 mL of CTL media for concentration of 0.4 million per mL. Plated out 0.5 mL or 0.2 million LCL into 4 wells of a 24-w-p.

Spun down D9 T cells for GMP condition, re-suspended in 4 mL for approximately 0.6 million of T cells per well and added 1 mL to each of the 4 wells with LCL. T cell to LCL ratio was about 3:1. Incubated at 37° C.

Condition DC(px):

Spun down DC(px) day 9 T cells, re-suspended in 4 mL of T cell media with 2×IL4 and IL7 concentration at 20 ng/mL. Plated out 1 mL per well of a 24-w-p. Added 0.5 mL of pepmix pulsed OKT3 blasts, then added 0.5 mL of aK562cs into each of the well to make a final volume of 2 mL per well, with T cell: OKT3 blasts:aK562cs ratio of 1:1:1 (low ratio of aK562cs due to low total aK562cs available). Incubated at 37° C.

Condition Px:

Spun down Px day 9 T cells, re-suspended in 6 mL of T cell media with 2×IL4 and IL7 concentration at 20 ng/mL. Plated out 1 mL per well of a 24-w-p. Added 0.5 mL of pepmix pulsed OKT3 blasts, then added 0.5 mL of aK562cs into each of the well to make a final volume of 2 mL per well, with T cell: OKT3 blasts:aK562cs ratio of 1:1:1 (low ratio of aK562cs due to low total aK562cs available). Incubated at 37° C.

D21 Added 1L2 to culture day 14 by replacing 1 mL of media in each well with 1 mL of media with 100 units of IL2 per mL to make final IL2 concentration 50 units/mL.

D22 Coating OKT3/CD28 plate

Prepared OKT3 and CD28 antibodies by adding 5 ug each of OKT3 and CD28 antibodies to 5 mL of sterile water.

Added 0.5 mL of this mixture into each well of a non-tissue culture treated 24 well plate (24-w-p). Incubated at 4° C. overnight.

D23 Activated patient 1 OKT3 blasts by thawing out a frozen vial with 20 million cells, then plated them on OKT3/CD28 coated plate.

Transduced patient 1 LCL by spinning down 2 million of LCL leaving ~50 ul of media left, then added 2 ul of Ad-LMP1-LMP2 at 5×10^12 vp/mL for MOI of 5000. Flicked tube every ~15 min, and after 1.5 hrs re-suspended in 5 mL of complete RPMI media.

D24 Culture day 16: replaced media with fresh media without any cytokines. Incubated at 37° C. Coated plate for ELISpot assay on D17:

Prewetted a 96-w immobilon-P membrane plate with 50 ul of 35% EtOH per well. Washed with PBS.

Made IFNy solution by adding 100 ug purified mouse anti-human IFNÅγ 1-D1K antibody to 10 mL of coating buffer. Added 100 ul per well to coat plate. Store at 4° C. overnight.

D25 Culture Day 17
Harvested and counted patient 1 day 17 T cells:
Condition GMP: 8.2 million
Condition DC(px): 5.5 million
Condition Px: 15.6 million
Harvested, irradiated at 30 Gy and counted OKT3 blasts: 13.6 million
Harvested, irradiated at 40 Gy and counted patient 1 LCL: 1.2 million
Harvested, irradiated at 100 Gy and counted aK562cs: 22.5 million.

Setting up ELISpot assay to detect IFNγ release:

Blocked a 96-w-plate (with membrane coated with IFNy primary antibody from the day before) with T cell media for 1 hr at 37[*]° C.

Prepared responder cells: Took out ~1.5 million of T cells from GMP condition, 0.8 million from DC(px) condition, and 0.8 million from Px condition, spun down, and re-suspended at 0.5 million per mL.

Prepared pepmix solution by adding 4 ul of pepmix stock in DMSO (0.2 ug/ul) into 800 ul of T cell media the following antigens: EBNA1, LMP1, LMP2, and added 1.5 ul of pepmix stock in DMSO into 300 ul of T cell media of the following antigens EBNA3a, EBNA3b, EBNA3c, Bzlf1, NY-ES01 (irrelevant antigen for negative control), staph aureus super-antigen (positive control). Prepared patient 1 LCL by taking out ⁻1 million of cells, spun down, resuspended in 1 million per mL. Added these antigens and targets to the responder T cells as following with each space represents 2 wells duplicates:

| GMP condition | EBNA1 Bzlf1 | LMP1 LCL | LMP2 (−)ve control | EBNA3a (+)ve control | EBNA3b | EBNA3c |
|---|---|---|---|---|---|---|
| DC(px) | EBNA1 | LMP1 | LMP2 | LCL | (−)ve control | (+)ve control |
| Px | EBNA1 | LMP1 | LMP2 | LCL | (−)ve control | (+)ve control |

Added 100 ul or 50,000 cells into each well, with GMP 24 wells, DC(px) and Px each with 12 wells.

Incubated overnight at 37° C.

Optional Steps
Third stimulation:
Pulsing of OKT3 blasts with pepmixes:

Diluted EBNA1, LMP1 and LMP2 pepmixes by adding 1 ul of stock pepmix solution (in DMSO) each into 200 ul of sterile PBS.

Spun down OKT3 blasts and aspirated all but ~50 ul of media. Loosened pellets by flicking the tubes. Added ~20 ul of diluted pepmix to the pellets, incubated at 37[*]° C. for 30 min with occasional flicking. Washed with 20 mL of PBS, spun down.

Re-suspended OKT3 blasts at concentration of million per mL, then further dilute out to 0.4 million per mL.

Condition GMP:
Spun down irradiated LCL and re-suspended in 10 mL of CTL media for concentration of 0.12 million per mL. Plated out 0.1 million or 1 mL each into 6 wells of a 24-w-p. Spun down 3 million of D17 T cells for GMP condition, re-suspended in 6 mL for and added 1 mL to each of the 6 wells with LCL. T cell to LCL ratio was about 4:1.

Incubated at 37° C. Froze down the rest of T cells

Condition DC(px):
Spun down 2 million of DC(px) day 17 T cells, re-suspended in 10 mL of T cell media with 2×1L4 and IL7 concentration at 20 ng/mL. Plated out 1 mL per well of a 24-w-p. Added 0.5 mL of pepmix pulsed OKT3 blasts, then added 0.5 mL of aK562cs into each of the well to make a final volume of 2 mL per well, with T cell: OKT3 blasts:aK562cs ratio of 2:2:5. Incubated at 37° C. (increased T cell and OKT3 blasts concentration since the growth after second stimulation was not great). Froze down the rest of T cells.

Condition Px:
Spun down 2 million of Px day 17 T cells, re-suspended in 10 mL of T cell media with 2×1L4 and 1L7 concentration at 20 ng/mL. Plated out 1 mL per well of a 24-w-p. Added 0.5 mL of pepmix pulsed OKT3 blasts, then added 0.5 mL of aK562cs into each of the well to make a final volume of 2 mL per well, with T cell: OKT3 blasts:aK562cs ratio of 2:2:5. Incubated at 37° C. (Increased T cell and OKT3 blasts concentration to match with DC(px) condition). Froze down the rest of T cells.

D29 Developed ELISpot IFNγ plate.

Prepared secondary IFNγ antibody (7B6-1 biotin) by adding 10 ul of antibody to 10 mL of PBS+0.5% BSA, then filtered through a 0.2 ul filter to get rid of clumps of conjugated antibodies to prevent non-specific binding. Washed plate 6× with 100 ul of PBS+0.05% Tween per well each time. Added 100 ul of this secondary antibody solution to each well. Incubated at 37° C. for 2 hours.

After 1.5 hours prepared 10 mL of Avidin-Peroxidase complex solution in PBS+0.05% Tween, mixed, and incubated at room temperature. At the end of the 2 hr, washed plate 6× with 100 ul PBS+0.05% Tween per well each time. Added 100 ul Avidin-Peroxidase complex solution to each well, incubated at room temperature for 1 hour.

At the end of the incubation, prepared AEC substrate by first dissolving AEC tablet into 2.5 mL Dimethylformamide, then added 47.5 mL acetate buffer (4.6 mL 0.1N acetic acid, 11 mL sodium acetate, 47 mL water), next added 25 ul 30% hydrogen peroxide, mixed & filtered with a 0.45 ul filter. Washed plates with PBS+0.05% Tween, repeated 3×, washed with PBS, repeated 3×, added AEC substrate and let develop for up to 4 minutes. Stopped reaction by rinsing with water. Peeled of the back and dry the membranes. Punch out results and sent for counting.

D31 Added IL2 to culture day 20 by replacing 1 mL of media in each well with 1 mL of media with 100 units of IL2 per mL to make final IL2 concentration 50 units/mL.

D32 Coating OKT3/CD28 plate
Prepared OKT3 and CD28 antibodies by adding 5 ug each of OKT3 and CD28 antibodies to 5 mL of sterile water.

Added 0.5 mL of this mixture into each well of a non-tissue culture treated 24 well plate (24-w-p). Incubated at 4° C. overnight.

D33 Activated patient 1 OKT3 blasts by plated on-going patient 1 OKT3 blast culture on OKT3/CD28 coated plate at ~1 million per well.

Transduced patient 1 LCL by spinning down 2 million of LCL leaving ~50 ul of media left, then adding 2 ul of Ad-LMP1-LMP2 at 5×10"12 vp/mL for MOI of 5000. Flicked tube every ~15 min, and after 1.5 hrs re-suspended in 5 mL of complete RPMI media.

D34 Culture day 23: replaced media with fresh media without any cytokines and split any wells that is over ~4 million cells. Incubated at 37° C.

Coated plate for ELISpot assay:
Prewetted a 96-w immobilon-P membrane plate with 50 ul of 35% EtOH per well. Washed with PBS.
Prepared IFNγ solution by adding 100 ug purified mouse anti-human IFNγ 1-D1K antibody to 10 mL of coating buffer. Added 100 ul per well to coat plate. Stored at 4° C. overnight.

D35 Culture day 24
Harvested patient 1 day 24 T cell culture and counted:
Condition GMP: 22.2 million
Condition DC(px): 39.8 million
Condition Px: 16.2 million
Harvested OKT3 blasts, irradiated at 30 Gy and counted: 9.8 million
Harvested patient 1 LCL, irradiated at 40 Gy and counted: 2.3 million
Harvested aK562cs, irradiated at 100 Gy and counted: 20 million Setting up ELISpot assay to detect IFNγ release:
Blocked a coated 96-w-plate with T cell media for 1 hr at 37° C.
Prepared responder cells: Took out ~2.5 million each of T cells from GMP condition, DC(px) condition, and Px condition, spun down, and re-suspended at 1 million per mL.
Prepared pepmix solution by adding 4 ul of pepmix stock in DMSO (0.2 ug/ul) into 800 ul of T cell media the following antigens: EBNA1, LMP1, LMP2, and adding 1.5 ul of pepmix stock in DMSO into 300 ul of T cell media of the following antigens: EBNA3a, EBNA3b, EBNA3c, Bzlf1, NY-ESO1 (irrelevant antigen for negative control), staph aureus super antigen (positive control). Prepared patient 1 LCL by taking out ~1 million of cells, spun down, re-suspended in 1 million per mL. Added these antigens and targets to the responder T cells as following with each space represents 2 wells (duplicates):

| GMP condition | EBNA1 Bzlf1 | LMP1 LCL | LMP2 (−)ve control | EBNA3a (+)ve control | EBNA3b | EBNA3c |
|---|---|---|---|---|---|---|
| DC(px) | EBNA1 | LMP1 | LMP2 | LCL | (−)ve control | (+)ve control |
| Px | EBNA1 | LMP1 | LMP2 | LCL | (−)ve control | (+)ve control |

Added 100 ul or 50,000 cells into each well, with GMP 24 wells, DC(px) and Px each with 12 wells.
Incubated overnight at 37° C.
Setting up co-culture of lymphoma patient 1 T cells and autologous LCL
For each condition, added T cell and LCL to a well of a 24-w-p to the ratios below:

| T cell to LCL ratio | 40:1 | 20:1 | 10:1 | 5:1 | 1:1 | 1:1 allo LCL |
|---|---|---|---|---|---|---|
| T cell count(million) | 0.5 | 0.5 | 0.5 | 0.5 | 0.5 | 0.5 |
| LCL cell count(million) | 0.0125 | 0.025 | 0.05 | 0.1 | 0.5 | 0.5 |

Added IL2 to the culture for final concentration of 50 u/mL and mixed gently with transfer pipet. Phenotyped day 0 by taking out 200 ul of each culture, washed with 3 mL of PBS+0.5% FBS, spun down, aspirated supernatant and added 5 ul each of the following antibodies: CD19-PE, CD56-FITC, and CD3-PerCP. Incubated at 4° C. for 1 hour. Washed with 3 mL PBS, spun down, aspirated supernatant and added 250 ul of cytofix per tube and 50 ul of Count-Bright beads. Analyzed with a flow cytometer.

Fourth stimulation:
Pulsing of OKT3 blasts with pepmixes:
Diluted EBNA1, LMP1 and LMP2 pepmixes by adding 1 ul of stock pepmix solution (in DMSO) each into 200 ul of sterile PBS.
Spun down OKT3 blasts and aspirated all but ~50 ul of media. Loosened pellets by flicking the tubes. Added ~20 ul of diluted pepmix to the pellets, incubated at 37° C. for 30 min with occasional flicking. Washed with 20 mL of PBS, spun down.
Re-suspended OKT3 blasts at concentration of million per mL, then further diluted out to 0.4 million per mL.
Re-suspended aK562cs at 2 million per mL.

Condition GMP:
Spun down irradiated LCL and re-suspended in 18.4 mL of CTL media for concentration of 0.12 million per mL. Plated out 0.12 million or 1 mL each into 10 wells of a 24-w-p. Spun down 5 million of D24 T cells for GMP condition, re-suspended in 10 mL for and added 1 mL to each of the 10 wells with LCL. T cell to LCL ratio was about 4:1. Incubated at 37° C. Froze down the rest of T cells.

Condition DC(px):
Spun down 2 million of DC(px) day 24 T cells, re-suspended in 10 mL of T cell media with 2×IL4 and IL7 concentration at 20 ng/mL. Plated out 1 mL per well of a 24-w-p. Added 0.5 mL of pepmix pulsed OKT3 blasts, then added 0.5 mL of aK562cs at 2 million per mL into each of the well to make a final volume of 2 mL per well, with T cell: OKT3 blasts:aK562cs ratio of 1:1:5. Incubated at 37° C. Froze down the rest of T cells Condition Px:
Spun down 2 million of Px day 24 T cells, re-suspended in 10 mL of T cell media with 2× IL4 and IL7 concentration at 20 ng/mL. Plated out 1 ml per well of a 24-w-p. Added 0.5 mL of pepmix pulsed OKT3 blasts, then added 0.5 mL of aK562cs into each of the well to make a final volume of 2 mL per well, with T cell: OKT3 blasts:aK562cs ratio of 1:1:5. Incubated at 37° C. Frozen down the rest of T cells.

D36 Developed ELISpot IFNγ plate.
Prepared secondary IFNγ antibody (7B6-1 biotin) by adding 10 ul of antibody to 10 mL of PBS+0.5% BSA, then filtered through a 0.2 ul filter to get rid of clumps of conjugated antibodies to prevent non-specific binding: Washed plate 6× with 100 ul of PBS+0.05% Tween per well each time. Added 100 ul of this secondary antibody solution to each well. Incubated at 37° C. for 2 hours.
After 1.5 hours prepared 10 mL of Avidin-Peroxidase complex solution in PBS+0.05% Tween, mixed, and incubated at room temperature. At the end of the 2 hr, washed plate 6× with 100 ul PBS+0.05% Tween per well each time. Added 100 ul Avidin-Peroxidase complex solution to each well, incubated at room temperature for 1 hour.

At the end of the incubation, prepared AEC substrate by first dissolving AEC tablet into 2.5 mL Dimethylformamide, then added 47.5 mL acetate buffer (4.6 mL 0.1N acetic acid, 11 mL sodium acetate, 47 mL water), next added 25 ul 30% hydrogen peroxide, mixed & filtered with a 0.45 ul filter. Washed plates with PBS+0.05% Tween, repeated 3×, washed with PBS, repeated 3×, added AEC substrate and let develop for up to 4 minutes. Stopped reaction by rinsing with water. Peeled of the back and dry the membranes. Punched out results and sent for counting. Co-culture day 2 phenotyping Replaced 1 mL of media with 1 mL of fresh t cell media with 100 units of IL2.

Phenotyped day 2 by taking out 200 ul of each condition, wash with 3 mL of PBS+0.5% FBS, spun down, aspirated supernatant and added 5 ul each of the following antibodies: CD19-PE, CD56-FITC, and CD3-PerCP. Incubated at 4° C. for 1 hour. Wash with 3 mL PBS, spun down, aspirated supernatant and added 250 ul of cytofix per tube and 50 ul of CountBright beads. Analyzed with a flow cytometer.

D38 Co-culture day 4 phenotyping

Took out 200 ul of each condition, washed with 3 mL of PBS+0.5% FBS, spun down, aspirated supernatant and added 10 ulj## each of the following antibodies: CD19-PE, CD56-FITC, and CD3-PerCP (increased antibody amount to match with increased cell counts), Incubated at 4° C. for 1 hour. Washed with 3 mL PBS, spun down, aspirated supernatant and added 250 ul of cytofix per tube and 50 ul of CountBright beads. Analyzed with a flow cytometer.

Added IL2 to culture day 20 by replacing 1 mL of media in each well with 1 mL of media with 100 units of 1L2 per mL to make final IL-2 concentration 50 units/mL. Spit confluent wells.

D39 Co-culture day 5 phenotyping

Took out 200 ul of each condition, washed with 3 mL of PBS+0.5% FBS, spun down, aspirated supernatant and added 10 ul each of the following antibodies: CD19-PE, CD56-FITC, and CD3-PerCP. Incubated at 4° C. for 1 hour. Washed with 3 mL PBS, spun down, aspirated supernatant and added 250 ul of cytofix per tube and 50 ul of CountBright beads. Analyzed with a flow cytometer.

D41 Culture day 30: replaced media with fresh media without any cytokines and split any wells that is over ⁻4 million cells. Incubated at 37° C.

Coated plate for ELISpot assay:

Prewetede a 96-w immobilon-P membrane plate with 50 ul of 35% EtOH per well. Washed with PBS.

Prepared IFNy solution by adding 100 ug purified mouse anti-human IFNy 1-D1K antibody to 10 mL of coating buffer. Added 100 ul per well to coat plate. Stored at 4° C. overnight.

D42 Culture day 31

Harvested patient 1 day 31 T cell culture and counted:

Condition GMP: 17.2 million; Condition DC(px): 20.6 million; Condition Px: 26.8 million Results Table 2: Whole culture expansion: Compared to current standard protocol (GMP), cultures set up with KATpx expanded just as well, if not better, by the end of the 4th stimulation.

TABLE 2

| | Growth in million of cells: | | | | |
|---|---|---|---|---|---|
| | D0 | D 9 | D 16 | D 23 | D 30 |
| Ad-DC | 1 | 2.13 | 8.317143 | 61.54686 | 211.7212 |
| DC | 1 | 0.6 | 1.375 | 27.3625 | 281.8338 |
| Px | 1 | 1.01333 | 5.269333 | 42.6816 | 571.9334 |

We have optimized a novel antigen presentation complex, KATpx, which produced equally good or better expansion and higher T cell antigen specific frequencies against EBNA1, LMP1 and LMP2 in a lymphoma patient. These cells efficiently eliminate tumor cells in co-culture and this killing was HLA specific. Moreover, using this approach we eliminated the need for LCL and Adenoviral vector, thus reducing generation time as well as activation of T cells specific for bystander antigens expressed by LCL and Adenoviral vector.

It is envisaged that more than one embodiment described herein may be combined, as technically appropriate. In the context of this specification "comprising" is to be interpreted as "including". Aspects of the disclosure comprising certain elements are also intended to extend to alternative embodiments "consisting" or "consisting essentially" of the relevant elements. All references referred to herein are specifically incorporated by reference.

The invention claimed is:

1. A process for in vitro expansion of antigen specific T cells, comprising steps of:
   a) culturing a population of peripheral blood mononuclear cells (PMBCs) in the presence of:
      i) a peptide or a peptide mix relevant to one or more target antigens OR dendritic cells which have been pulsed with the peptide or the peptide mix, and
      ii) at least one cytokine, thereby obtaining a population of T cells; and
   b) culturing the population of T cells in the presence of:
      antigen presenting cells (APCs) which have been pulsed with the peptide or the peptide mix, wherein the APCs are selected from the group consisting of:
         (1) dendritic cells; and
         (2) antigen presenting T cells autologous to the PMBCs; and
      an artificial co-stimulatory factor,
   characterized in that the process does not employ a live virus; a viral vector; or DNA or RNA encoding the target antigen(s).

2. The process according to claim 1, further comprising repeating step b) until a desired quantity of antigen-specific T cells is obtained.

3. The process according to claim 1 wherein the population of PBMCs is cultured for 12 or fewer days.

4. The process according to claim 1, wherein the population of T cells is cultured for 12 or fewer days.

5. The process according to claim 1, which is performed in a vessel comprising a gas permeable culture surface.

6. The process according to claim 1, wherein the one or more target antigens are selected from the group consisting of antigens of an Epstein-Barr Virus, a Vaccinia Virus, and a Varicella Zoster Virus.

7. The process according to claim 1, wherein the peptide mix comprises between 2 and 1000 peptides.

8. The process according to claim 1, wherein the peptides are about 10, 11, 12, 13, 14, 15, 16, 17, 18, 19 or 20 amino acids in length.

9. The process according to claim 1, wherein the antigen is LMP1.

10. The process according to claim 1, wherein the antigen is LMP2.

11. The process according to claim 1, wherein the antigen is EBNAI.

12. The process according to claim 1, wherein the antigen is BARFI.

13. The process according to claim 1, wherein the at least one cytokine present in step a) is IL-4.

14. The process according to claim 1, wherein the at least one cytokine present in step a) is IL-7.

15. The process according to claim 1, wherein step b) further comprises at least one cytokine, wherein the at least one cytokine present in step b) is IL-15.

16. The process according to claim 1, wherein the artificial co-stimulatory factor is a cell engineered to express one or more co-stimulatory molecules on its surface.

17. The process according to claim 16, wherein the one or more co-stimulatory molecules are independently selected from CD80, CD86, CD83, OX-40 ligand and 41BB-ligand or a fragment thereof.

18. The process according to claim 1, wherein the cell comprises CD80, CD86, CD83, OX-40 ligand and 41BB-ligand.

19. The process according to claim 1, wherein the process is performed in a GRex™ system.

20. The process according to claim 8, wherein peptides in the peptide mix overlap by 2, 3, 45, 6, 7, 8, 9, 10, 11, 12, 13, 14, or 15 or more amino acids.

21. The process according to claim 1, wherein the antigen specific T cells are allogeneic.

* * * * *

UNITED STATES PATENT AND TRADEMARK OFFICE
CERTIFICATE OF CORRECTION

| | |
|---|---|
| PATENT NO. | : 11,155,784 B2 |
| APPLICATION NO. | : 16/116023 |
| DATED | : October 26, 2021 |
| INVENTOR(S) | : Cliona M. Rooney et al. |

It is certified that error appears in the above-identified patent and that said Letters Patent is hereby corrected as shown below:

In the Claims

At Column 140, Claim number 20, Line number 21, delete "45" and replace with 4, 5

Signed and Sealed this
Third Day of May, 2022

Katherine Kelly Vidal
*Director of the United States Patent and Trademark Office*